(12) United States Patent
O'Brien

(10) Patent No.: US 11,579,225 B2
(45) Date of Patent: Feb. 14, 2023

(54) METHOD AND SYSTEM FOR IN-VIVO, AND NON-INVASIVE MEASUREMENT OF METABOLITE LEVELS

(71) Applicant: 10250929 Canada Inc., Toronto (CA)

(72) Inventor: David O'Brien, Toronto (CA)

(73) Assignee: 10250929 Canada Inc., Toronto (CA)

( * ) Notice: Subject to any disclaimer, the term of this patent is extended or adjusted under 35 U.S.C. 154(b) by 0 days.

(21) Appl. No.: 17/200,791

(22) Filed: Mar. 13, 2021

(65) Prior Publication Data

US 2021/0199736 A1 Jul. 1, 2021

Related U.S. Application Data

(63) Continuation of application No. PCT/CA2019/051305, filed on Sep. 13, 2019.

(Continued)

(51) Int. Cl.
  *G01R 33/465* (2006.01)
  *A61B 5/055* (2006.01)
  (Continued)

(52) U.S. Cl.
  CPC ........... *G01R 33/465* (2013.01); *A61B 5/055* (2013.01); *A61B 5/7203* (2013.01); *A61B 5/725* (2013.01);
  (Continued)

(58) Field of Classification Search
  CPC .......................... G01R 33/465; G01R 33/302; G01R 33/3678; A61B 5/055; A61B 5/702; A61B 5/7203; A61B 5/725; A61B 2560/0431
  See application file for complete search history.

(56) References Cited

U.S. PATENT DOCUMENTS 3,488,561 A   1/1970 Anderson
4,875,486 A   10/1989 Rapoport et al.
(Continued)

FOREIGN PATENT DOCUMENTS

CA   3112592 A1   3/2020
WO   WO-2007066244 A1 *  6/2007   ......... G01R 33/3635
WO   2020/051716 A1   3/2020

OTHER PUBLICATIONS

Ginsberg, "Factors Affecting Blood Glucose Monitoring: Sources of Errors in Measurement", Journal of Diabetes Science and Technology, Jul. 1, 2009, 3(4): 903-913.
(Continued)

*Primary Examiner* — Dixomara Vargas
(74) *Attorney, Agent, or Firm* — Tony Orsi; Bereskin & Parr LLP / S.E.N.C.R.L,s.r.l.

(57) ABSTRACT

Embodiments of a compact portable nuclear magnetic resonance (NMR) device are described which generally include a housing that provides a magnetic shield; an axisymmetric permanent magnet assembly in the housing and having a bore, a plurality of magnetic elements that together provide a well confined axisymmetric magnetization for generating a near-homogenous magnetic dipole field $B_0$ directed along a longitudinal axis and providing a sample cavity for receiving a sample, and high magnetic permeability soft steel poles to improve field uniformity: a shimming assembly with coils disposed at the longitudinal axis for spatially correcting the near homogenous magnetic field $B_0$; and a spectrometer having a control unit for measuring a metabolite in the sample by applying magnetic stimulus pulses to the sample, measuring free induction delay signals generated by an ensemble of hydrogen protons within the sample; and suppressing a water signal by using a dephasing gradient with frequency selective suppression.

30 Claims, 23 Drawing Sheets

Related U.S. Application Data

(60) Provisional application No. 62/731,576, filed on Sep. 14, 2018.

(51) Int. Cl.

| | |
|---|---|
| *A61B 5/00* | (2006.01) |
| *G01R 33/30* | (2006.01) |
| *G01R 33/36* | (2006.01) |
| *A61B 5/145* | (2006.01) |
| *G01N 33/49* | (2006.01) |
| *G01R 33/3875* | (2006.01) |
| *G01N 24/08* | (2006.01) |
| *G01R 33/383* | (2006.01) |
| *H01F 1/057* | (2006.01) |
| *H01F 7/02* | (2006.01) |

(52) U.S. Cl.
CPC ....... *G01R 33/302* (2013.01); *G01R 33/3678* (2013.01); *A61B 5/14532* (2013.01); *A61B 5/702* (2013.01); *A61B 5/7257* (2013.01); *A61B 5/7278* (2013.01); *A61B 2560/0431* (2013.01); *G01N 24/08* (2013.01); *G01N 33/49* (2013.01); *G01R 33/383* (2013.01); *G01R 33/3875* (2013.01); *H01F 1/057* (2013.01); *H01F 7/021* (2013.01)

(56) References Cited

U.S. PATENT DOCUMENTS

| | | | |
|---|---|---|---|
| 5,072,732 | A | 12/1991 | Rapoport et al. |
| 5,172,060 | A | 12/1992 | Knüttel |
| 5,320,103 | A | 6/1994 | Rapoport et al. |
| 5,433,196 | A | 7/1995 | Fiat |
| 5,635,889 | A | 6/1997 | Stelter |
| 5,685,300 | A | 11/1997 | Kuenstner |
| 5,886,609 | A | 3/1999 | Stelter |
| 6,163,154 | A | 12/2000 | Anderson et al. |
| 6,404,197 | B1 | 6/2002 | Anderson et al. |
| 7,635,331 | B2 | 12/2009 | Kim et al. |
| 8,712,706 | B2 | 4/2014 | Leskowitz et al. |
| 8,860,539 | B2 | 10/2014 | Sakellariou et al. |
| 8,902,030 | B2 | 12/2014 | Aubert |
| 9,361,429 | B2 | 6/2016 | Otvos et al. |
| 10,416,264 | B2 * | 9/2019 | Sofka .................. G01R 33/445 |
| 2006/0103386 | A1 * | 5/2006 | Buchwald .......... G01R 33/3621 324/309 |
| 2006/0273942 | A1 * | 12/2006 | Koste ................. H03M 1/1033 341/118 |
| 2009/0105785 | A1 * | 4/2009 | Wei .................... A61N 1/36132 600/301 |
| 2009/0264789 | A1 * | 10/2009 | Molnar .............. A61N 1/36135 600/595 |
| 2010/0072994 | A1 | 3/2010 | Lee et al. |
| 2010/0225314 | A1 | 9/2010 | Kuge et al. |
| 2011/0101979 | A1 * | 5/2011 | Wiesinger .......... G01R 33/5602 324/309 |
| 2011/0144573 | A1 * | 6/2011 | Rofougaran ......... A61B 5/0022 604/66 |
| 2011/0160802 | A1 * | 6/2011 | Rofougaran ........... G16H 10/65 607/60 |
| 2012/0081119 | A1 | 4/2012 | Murphree, Jr. et al. |
| 2013/0207655 | A1 * | 8/2013 | Biber ................. G01R 33/3875 324/321 |
| 2014/0276187 | A1 * | 9/2014 | Iasemidis ............... A61B 5/369 600/544 |
| 2015/0005243 | A1 | 1/2015 | O'Day et al. |
| 2015/0018638 | A1 | 1/2015 | Shames et al. |
| 2016/0011290 | A1 | 1/2016 | Iannello |
| 2016/0069975 | A1 * | 3/2016 | Rothberg ........... G01R 33/3852 324/322 |
| 2016/0116554 | A1 | 4/2016 | Sakellariou et al. |
| 2016/0128592 | A1 * | 5/2016 | Rosen .................... A61B 5/389 600/411 |
| 2017/0254866 | A1 | 9/2017 | Haenichen et al. |
| 2017/0299678 | A1 | 10/2017 | Bastiaansen |
| 2017/0325710 | A1 * | 11/2017 | Ryan ...................... A61B 5/055 |
| 2018/0109411 | A1 * | 4/2018 | Sen .................... G01R 33/3607 |
| 2018/0143280 | A1 * | 5/2018 | Dyvorne .............. G01R 33/389 |
| 2021/0121108 | A1 | 4/2021 | Nashman et al. |
| 2021/0231760 | A1 * | 7/2021 | Raynal ............... G01R 33/3875 |

OTHER PUBLICATIONS

Ekhlaspour et al., "Comparative Accuracy of 17 Point-of-Care Glucose Meters", Journal of Diabetes Science and Technology, 2017 (first published Oct. 3, 2016), 11(3): 558-566.

Boyd et al., "Quality Specifications for Glucose Meters: Assessment by Simulation Modeling of Errors in Insulin Dose", Clinical Chemistry, 2001, 47(2): 209-214.

Smith, "The Pursuit of Noninvasive Glucose: 'Hunting the Deceitful Turkey'", 5th ed., 2017, pp. 1-203.

De Graaf, Chapter 2 (pp. 47, 51, 59 & 78), in "In Vivo NMR Spectroscopy: Principles and Techniques", 2nd Edition, John Wiley & Sons Ltd., Oct. 26, 2007.

Gruetter et al., "Observation of Resolved Glucose Signals in 1H NMR Spectra of the Human Brain at 4 Tesla", Magnetic Resonance in Medicine, 1996, 36(1): 1-6.

The Human Metabolome Database website, screen captured on Jun. 26, 2018 <https://web.archive.org/web/20180626031849/http://www.hmdb.ca> (3 pages).

Wishart et al., "HMDB 3.0—The Human Metabolome Database in 2013", Nucleic Acids Research, 2013 (published online Nov. 17, 2012), 41(D1): D801-D807.

Hoult et al., "The Signal-to-Noise Ratio of the Nuclear Magnetic Resonance Experiment", Journal of Magnetic Resonance, 1976, 24(1): 71-85.

Hoult et al., "The Sensitivity of the Zeugmatographic Experiment Involving Human Samples", Journal of Magnetic Resonance, 1979, 34(2): 425-433.

Nishimura, Chapter 6, in "Principles of Magnetic Resonance Imaging", 1.2 ed., Palo Alto, California: www.lulu.com, 2016, p. 102.

Handwerker et al., "An Active TX/RX NMR Probe for Real-Time Monitoring of MRI Field Imperfections", 2013 IEEE Biomedical Circuits and Systems Conference (BioCAS) (Oct. 31-Nov. 2, 2013), Rotterdam, Netherlands, Dec. 12, 2013, pp. 194-197.

Chen et al., "Biomedical Magnetic Resonance Technology", Bristol, England: Adam Hilger imprint by IOP Publishing Ltd., Jan. 1, 1989, pp. 122, 123, 128 & 129.

International Commission on Non-Ionizing Radiation Protection, "ICNIRP Guidelines on Limits of Exposure to Static Magnetic Fields", Health Physics, Apr. 2009, 96(4): 504-514.

Mallinson, "One-Sided Fluxes—A Magnetic Curiosity?", IEEE Transactions on Magnetics, Dec. 1973, MAG-9 (4): 678-682.

Shute et al., "One-sided Fluxes in Planar, Cylindrical, and Spherical Magnetized Structures", IEEE Transactions on Magnetics, 2000, 36(2): 440-451.

Halbach, "Design of Permanent Multipole Magnets with Oriented Rare Earth Cobalt Materials", Nuclear Instruments and Methods, Feb. 1, 1980, 169(1): 1-10 (12 pages).

Zijlstra, "Permanent Magnet Systems for NMR Tomography", Philips Journal of Research, 1985, 40(5): 259-288.

Küstler, "Computation of NdFeB-Halbach Cylinders with Circular and Elliptical Cross Sections in Three Dimensions", IEEE Transactions on Magnetics, Sep. 2010, 46(9): 3601-3607.

Elkins et al., "Magnetic resonance velocimetry: applications of magnetic resonance imaging in the measurement of fluid motion", Experimental Fluids, Oct. 23, 2007, 43: 823-858.

Piro et al., "Fluid flow investigations within a 37 element CANDU fuel bundle supported by magnetic resonance velocimetry and computational fluid dynamics", International Journal of Heat and Fluid Flow, Aug. 2017, 66: 27-42.

(56) References Cited

OTHER PUBLICATIONS

Wasserman et al., "Magnetic Resonance Velocimetry Measurements of the Flow through a Fuel Bundle", Computational Fluid Dynamics for Nuclear Reactor Safety Applications, Zurich, Switzerland, Nov. 2017 (13 pages).

Klarhöfer et al., "High-Resolution Blood Flow Velocity Measurements in the Human Finger", Magnetic Resonance in Medicine, 2001, 45(4): 716-719.

Humphries, "Cosine coils in Magnum calculations", Field Precision software Tips, Jan. 5, 2009 <http://fieldp.com/myblog/2009/cosine-coils-in-magnum-calculations> (3 pages).

AD Elster, Elster LLC, "Birdcage Coils", Questions and Answers in MRI, screen captured on Sep. 4, 2018 <https://web.archive.org/web/20180904114117/http://mriquestions.com/birdcage-coil.html>.

Smythe, Chapter 7, in "Static and Dynamic Electricity", 2nd ed., McGraw Hill, 1950, p. 275.

Van Zijl et al., "Optimized Shimming for High-Resolution NMR Using Three-Dimensional Image-Based Field Mapping", Journal of Magnetic Resonance, 1994, 111(2): 203-207.

Centers for Disease Control and Prevention, "Infection Prevention during Blood Glucose Monitoring and Insulin Administration", Mar. 2, 2011 <https://www.cdc.gov/injectionsafety/blood-glucose-monitoring.html> (6 pages).

Dall et al., "The Economic Burden of Elevated Blood Glucose Levels in 2017: Diagnosed and Undiagnosed Diabetes, Gestational Diabetes Mellitus, and Prediabetes", Diabetes Care, Apr. 2019, 42:1661-1668.

International Search Report and Written Opinion dated Jan. 2, 2020 in International Patent Application No. PCT/CA2019/051305 (15 pages).

Luaibi et al., "Noninvasive Blood Glucose Level Measurement Using Nuclear Magnetic Resonance", Proceedings of the 8th IEEE GCC Conference and Exhibition, Muscat, Oman, Feb. 1-4, 2015 (4 pages).

Sun et al., "Small NMR biomolecular sensors", Solid-State Electronics, 2013, 84: 13-21.

Crouch et al., "Easy, Precise, and Accurate Quantitative NMR—Application Note", Agilent Technologies, 2011, pp. 1-7.

Non-final Office Action and Notice of References Cited dated May 12, 2021 in U.S. Appl. No. 17/200,788 (20 pages).

Non-final Office Action and Notice of References Cited dated May 6, 2022 in U.S. Appl. No. 17/200,795 (8 pages).

Extended European Search Report dated Sep. 12, 2022 in EP Patent Application No. 19860113.0 (15 pages).

Xin et al., "A practical guide to in vivo proton magnetic resonance spectroscopy at high magnetic fields", Anal Biochem., 2017 (epub 2016), 529: 30-39.

Moonen et al., "Highly Effective Waer Suppression for in vivo proton NMR Spectroscopy (DRYSTEAM)", Journal of Magnetic Resonance, 1990, 88(1): 28-41.

\* cited by examiner

METHOD AND SYSTEM FOR IN-VIVO, AND NON-INVASIVE MEASUREMENT OF METABOLITE LEVELS

CROSS-REFERENCE

This application is a continuation of International Patent Application No. PCT/CA2019/051305, filed Sep. 13, 2019, which claims the benefit of U.S. Provisional Patent Application No. 62/731,576, filed Sep. 14, 2018, and the entire contents of each of which are hereby incorporated by reference.

FIELD

Various embodiments are described herein that generally relate to measurement of metabolite levels and, in particular, to a portable nuclear magnetic resonance (NMR) device for in-vivo, and non-invasive measurement of metabolite levels.

BACKGROUND

Conventional techniques for measuring metabolite levels in blood samples are often invasive, in-accurate, and non-repeatable. For example, current blood glucose measurement technology requires puncturing a subject's skin with a lance to deposit a small sample of blood on a biochemically reactive, disposable, and single-purpose test strip. Each blood sample requires a new deposit. The inconvenience of repeatedly puncturing the skin, as well as the cost burden associated with purchasing new test strips for each batch of samples, often becomes an impediment to frequent glucose testing. This is particularly concerning for individuals who suffer from Type 1 diabetes, or advanced stages of Type 2 diabetes, and who require frequent and accurate testing to insure proper insulin dosing decisions.

SUMMARY OF VARIOUS EMBODIMENTS

In accordance with a broad aspect of the teachings herein, there is provided at least one embodiment of a method for in-vivo and non-invasive quantitation of glucose concentration in a sample using a portable nuclear magnetic resonance (NMR) device, the method comprising: applying a uniform static magnetic field ($B_0$) to induce magnetization of the sample; suppressing a water signal generated by the magnetization of water located in the sample using frequency selective suppression; applying a first RF stimulus pulse ($B_1$) to excite an ensemble of glucose hydrogen protons; and detecting a free induction delay (FID) signal generated by the relaxation of the ensemble of glucose hydrogen protons.

In at least one of these embodiments, suppressing the water signal further comprises: applying a second RF stimulus pulse ($B_1$) to rotate the water magnetization onto a transverse plane; and applying a dephasing pulse gradient to the water signal to de-phase the coherence of its spin precession, wherein water suppression is performed in order to reduce modulation sidebands of the water signal.

In at least one of these embodiments, the static magnetic field ($B_0$) has a magnitude of between about 1.5 Tesla to about 2 Tesla.

In at least one of these embodiments, the static magnetic field ($B_0$) has a field uniformity of between about 0.01 ppm to less than about 0.1 ppm.

In at least one of these embodiments, the method comprises generating the second RF stimulus pulse ($B_1$) to have an excitation profile defined by the expression $|\sin c^2(\pi\Delta f\tau)|$, and wherein $2\tau$ is the duration of the pulse.

In at least one of these embodiments, the method comprises generating the second RF stimulus pulse ($B_1$) to have an excitation profile defined by the expression $|\sin c(\pi\Delta f\tau)|$, and wherein $\tau$ is the duration of the pulse.

In at least one of these embodiments, the method comprises generating the second RF stimulus pulse ($B_1$) to be centered at the resonance frequency of water ($f_{H2O}$) where $\tau$ is defined as $\tau=(f_{H2O}-f_{\beta\text{-}glc})^{-1}$, and $f_{\beta\text{-}glc}$ is the resonant frequency of beta-Glucose anomer $^1CH$ hydrogen group protons.

In at least one of these embodiments, the method comprises generating a static magnetic field ($B_0$) of about 1.68 Tesla, and the resonance frequency of water ($f_{H2O}$) is about 71.5 MHz, and $\tau$ is about 163 milliseconds.

In at least one of these embodiments, the method comprises providing the second RF stimulus pulse ($B_1$) by generating an envelope modulated pulse train with a low duty cycle.

In at least one of these embodiments, the method comprises generating the second RF stimulus pulse ($B_1$) using a Delays Alternating with Nutation for Tailored Excitation (DANTE) technique.

In at least one of these embodiments, the second RF stimulus pulse ($B_1$) is implemented as a hyperbolic secant pulse.

In at least one of these embodiments, the method comprises increasing the suppression of the water signal by generating a large magnitude second stimulus RF pulse ($B_1$).

In at least one of these embodiments, the dephasing pulse gradient is generated by a set of DC coupled shim coils.

In at least one of these embodiments, the ensemble of glucose hydrogen protons comprises alpha-Glucose anomer $^1CH$ hydrogen group protons and beta-Glucose anomer $^1CH$ hydrogen group protons.

In at least one of these embodiments, the method comprises generating the first RF stimulus pulse ($B_1$) so that a net magnetic moment of the ensemble of glucose hydrogen protons is rotated into a transverse plane.

In at least one of these embodiments, the method comprises generating the first RF stimulus pulse ($B_1$) in a frequency range that includes the Larmor frequencies of the alpha-Glucose anomer $^1CH$ hydrogen group protons and the beta-Glucose anomer $^1CH$ hydrogen group protons.

In at least one of these embodiments, the Larmor frequency of the alpha-Glucose anomer $^1CH$ hydrogen group protons is 5.223 ppm, and the Larmor frequencies of the eta-Glucose anomer $^1CH$ hydrogen group protons is 4.634 ppm.

In at least one of these embodiments, the method comprises generating the first stimulus field ($B_1$) to be left-hand circularly polarized.

In at least one of these embodiments, the method comprises applying the first stimulus field ($B_1$) for less than about 1.5 ms to mitigate transverse relaxation decay of the ensemble of glucose hydrogen protons at an exponential rate $T2^*$.

In at least one of these embodiments, the method comprises generating the first stimulus field ($B_1$) and the second stimulus field ($B_1$) by using canted cosine coils which are positioned co-axially with respect to each other and are tilted in opposite directions with respect to a common axis.

In at least one of these embodiments, the method further comprises applying homonuclear decoupling to the ensemble of glucose hydrogen protons and wherein applying homonuclear decoupling comprises: applying a low continuous wave irradiation pulse at the alpha anomer $^2$CH group hydrogen protons and the beta anomer $^2$CH group hydrogen protons resonance frequencies.

In at least one of these embodiments, the alpha and beta anomer $^2$CH group hydrogen protons resonance frequencies are 3.519 ppm and 3.23 ppm, respectively.

In at least one of these embodiments, the homonuclear decoupling at least partly overlaps with the applying the first RF stimulus pulse ($B_1$) to excite the ensemble of glucose hydrogen protons.

In at least one of these embodiments, the method further comprises applying a Discrete Fourier Transform (DFT) to the FID signal to convert the FID signal into a magnetic resonance frequency spectrum.

In at least one of these embodiments, the method further comprises determining a concentration of glucose in the sample based on a one-to-one mapping of an amplitude of the resonance peaks for the alpha-Glucose anomer $^1$CH hydrogen group protons and the beta-Glucose anomer $^1$CH hydrogen group protons in the resonance frequency spectrum.

In at least one of these embodiments, the determining the concentration of glucose in the sample comprises correlating an amplitude of the resonance peaks for the alpha-Glucose anomer $^1$CH hydrogen group protons and the beta-Glucose anomer $^1$CH hydrogen group protons to known glucose concentration reference standards.

In at least one of these embodiments, the determining the concentration of glucose in the sample comprises determining an anomeric ratio of the alpha-Glucose anomer $^1$CH hydrogen group protons and the beta-Glucose anomer $^1$CH hydrogen group protons resonance peaks.

In at least one of these embodiments, the method further comprises using non-selective inversion recovery sequence prior to applying the first RF stimulus pulse ($B_1$) in order to null a macromolecule response.

In at least one of these embodiments, the method further comprises using a selective inversion recovery sequence prior to applying the first RF stimulus pulse ($B_1$) in order to null a response of the ensemble of glucose hydrogen protons and measure a macromolecule response.

In at least one of these embodiments, a magnetic resonance velocimetry (MRV) technique is used to distinguish glucose molecules flowing in blood from stationary glucose molecules.

In at least one of these embodiments, the concentration of glucose is determined to an error less than +/−2% at 0.95 statistical confidence.

In accordance with another broad aspect of the teachings herein, there is provided at least one embodiment of a portable spectrometer for use in performing nuclear magnetic resonance (NMR) spectroscopy on a sample, the portable spectrometer comprising: a radiofrequency (RF) source configured to generate a pulsed RF signal having an in-phase component and a quadrature component; a transmitting unit being configured to receive the pulsed RF signal and generate a pulsed RF stimulus field ($B_1$), the transmission unit comprising: a first transmission pathway having a first transmitting bandpass filter with at least one first transmitting inductor coil which receives the in-phase component of the RF signal and generates the in-phase component of the RF stimulus field; and a second transmission pathway having a second transmitting bandpass filter with at least one second transmitting inductor coil which receives the quadrature component of the RF signal and generates the quadrature component of the RF stimulus field; a receiving unit configured to receive a resonance signal generated by the sample in response to the pulsed RF stimulus field ($B_1$), the receiving unit comprising: a first receiving pathway having a first receiving bandpass filter with at least one first receiving inductor coil which receives an in-phase component of the resonance signal; and a second receiving pathway having a second receiving bandpass filter with at least one second receiving inductor coil which receives a quadrature component of the resonance signal; and a processor unit that is coupled to the RF source, the transmitting unit, and the receiving unit, the processor unit being configured to control the operation of the portable spectrometer by sending a control signal to the RF source to generate the pulsed RF signal and send the pulsed RF signal to the transmitting unit for generating the pulsed RF stimulus field ($B_1$), and the processor unit being configured to receive the in-phase and quadrature components of the resonance signal from the receiving unit and wherein the processor performs at least one of: (a) storing the in-phase and quadrature components of the resonance signal in a memory unit of the processor unit for post-analysis; and (b) conduct an analysis on the in-phase and quadrature components of the resonance signal to determine the concentration of a metabolite in the sample.

In at least one of these embodiments, the first and second transmitting band pass filters and the first and second receiving band pass filters, are each differential band pass filters synthesized from a tee topology low pass filter.

In at least one of these embodiments, the at least one first transmitting inductor coil of the first transmitting band pass filter, the at least one second transmitting inductor coil of the second transmitting band pass filter, the at least one first receiving inductor coil of the first receiving band pass filter, and the at least one second receiving inductor coil of the second receiving band pass filter, are volume coils.

In at least one of these embodiments, the first and second transmitting band pass filters each include an outbound transmitting inductor coil, and a return transmitting coil, and the first and second receiving band pass filter each include an outbound receiving inductor coil, and a return receiving inductor coil.

In at least one of these embodiments, the transmitting and receiving band pass filters are at least $3^{rd}$ order band pass filters.

In at least one of these embodiments, the at least one first transmitting inductor coil of the first transmitting band pass filter, and the at least one second transmitting inductor coil of the second transmitting band pass filter, are each canted cosine coils which are positioned co-axially with respect to each other and are tilted in opposite directions with respect to a common axis in order to generate an RF stimulus field ($B_1$) which is at least one of circularly and elliptically polarized.

In at least one of these embodiments, the at least one first receiving inductor coil of the first receiving band pass filter, and the at least one second receiving inductor coil of the second receiving band pass filter, are each canted cosine coils which are positioned co-axially with respect to each other and are tilted in opposite directions with respect to a common axis.

In at least one of these embodiments, the common axis is orthogonal to an axis of a magnetic static field ($B_0$).

In at least one of these embodiments, the resonance signal is a free induction delay (FID) signal generated by a decay of a magnetization in a transverse plane.

In at least one of these embodiments, the receiving unit uses a sum and a difference of the FID signals received by the two canted cosine coils to discriminate a projection of the magnetization onto two transverse spatial axes.

In at least one of these embodiments, the first and second receiving pathways each comprise: a transformer comprising a primary winding coupled to an output of the receiving band pass filter, wherein the transformer is configured to provide galvanic isolation, impedance matching, and common-mode noise rejection; a low noise amplifier (LNA) coupled to a first node of a secondary winding of the transformer, wherein the LNA is configured to achieve a low noise figure in the filtered resonance signal and provide a uniform spectral noise distribution; a variable gain amplifier (VGA) coupled to an output of the low noise amplifier, wherein the VGA is configured to boost the filtered resonance signal and minimize the overall receiver noise; a local oscillator (LO) coupled to an output of the variable gain amplifier, wherein the LO is configured to generate an intermediate frequency; and an analog to digital converter (ADC) coupled to the output of the LO.

In at least one of these embodiments, a second node of the secondary winding of the transformer is center-tapped for local ground referencing, and wherein the turn ratio of the transformer is selected for optimal impedance matching.

In at least one of these embodiments, the transformer comprises a wideband transformer balun.

In at least one of these embodiments, the LNA is formed of GaAs E-pHEMT technology and is configured to provide a noise figure below 1 dB.

In at least one of these embodiments, the VGA includes an automatic gain controller (AGC) which is configured to automatically reduce a gain of the VGA to prevent overload.

In at least one of these embodiments, the local oscillator is configured for a frequency offset of at least 100 kHz.

In at least one of these embodiments, the noise generated by the receiving unit is less than 1.1 nV/√Hz as referred to input (RTI).

In at least one of these embodiments, the processor unit comprises at least one of a digital signal processor (DSP) and a field-programmable gate array (FPGA).

In at least one of these embodiments, the first and second transmitting band pass filters are configured to pass a first passband range of frequencies which include at least one isotope Larmor frequency.

In at least one of these embodiments, the first passband range of frequencies includes two isotope Larmor frequencies, and the transmitting band pass filter is configured to support heteronuclear measurements.

In at least one of these embodiments, the two isotope Larmor frequencies are in respect of the Larmor frequencies of fluorine ($^{19}F$) and hydrogen ($^{1}H$).

In at least one of these embodiments, the first passband range of frequencies is between 60 MHz and 80 MHz.

In at least one of these embodiments, the first and second receiving band pass filters are configured to pass a second passband range of frequencies which include at least one isotope Larmor frequency.

In accordance with another broad aspect of the teachings herein, there is provided at least one embodiment of a method for performing nuclear magnetic resonance (NMR) spectroscopy on a sample using a portable spectrometer, the method comprising: applying a static magnetic field ($B_0$) to the sample; generating, using a radiofrequency (RF) source, a pulsed RF signal having an in-phase component and a quadrature component; sending the in-phase component of the pulsed RF signal to a first transmitting band pass filter of a transmitting unit to generate a filtered in-phase RF component; sending the quadrature component of the pulsed RF signal through a second transmitting band pass filter of the transmitting unit to generate a filtered quadrature RF component, wherein the first and second transmitting band pass filters have a first band pass range that includes at least one Larmor frequency of a metabolite to be measured; generating a pulsed RF stimulus field ($B_1$) by applying the filtered in-phase RF component to at least one first transmitting inductor coil of the first transmitting band pass filter, and applying the filtered quadrature RF component to at least one second transmitting inductor coil of the second transmitting band pass filter; applying the pulsed RF stimulus field ($B_1$) to the sample; receiving an in-phase component of a resonance signal generated by the sample using at least one first receiving inductor coil of a first receiving band pass filter of a receiving unit; receiving a quadrature component of the resonance signal generated by the sample using at least one second receiving inductor coil of a second receiving band pass filter of the receiving unit, wherein the first and second receiving band pass filters have a second pass band range that includes the at least one Larmor frequency of the metabolite to be measured; and passing the in-phase component of the resonance signal through the first receiving band pass filter to generate a filtered in-phase component of the resonance signal, and passing the quadrature component of the resonance signal through the second receiving band pass filter to generate a filtered quadrature component of the resonance signal.

In at least one of these embodiments, the resonance signal is a free induction delay (FID) signal generated by a decay of a magnetization in a transverse plane.

In at least one of these embodiments, the method further comprises passing each of the in-phase component and the quadrature component of the resonance signal through a low noise amplifier, a variable gain amplifier, a local oscillator, and an analog to digital converter (ADC).

In accordance with another broad aspect of the teachings herein, there is provided at least one embodiment of a compact magnet assembly for generating a uniform static magnetic field ($B_0$) across of a bore of a portable nuclear magnetic resonance (NMR) device, the compact magnet assembly comprising: an axisymmetric segment permanent magnet assembly rotated around an axis of symmetry (z-axis), the permanent magnet configured to generate a near spatially-uniform static magnetic field ($B_0$) across of the bore, wherein the permanent magnet assembly comprises: a top disk-cone magnet segment stacked above the bore in a +z direction, and having a magnetization in the +z direction; a bottom disk-cone magnet segment stacked below the bore in a z direction, and having a magnetization in the +z direction; a central ring magnet segment located radially (r) outwardly from the bore in a +r direction and having a magnetization in the z direction, wherein the central ring magnet at least partially surrounds the bore while leaving unobstructed an access opening to the bore; a top ring magnet segment stacked over the central ring segment in the +z direction and disposed radially outwardly from the top disk-cone magnet segment in the +r direction, wherein the top ring magnet segment has a magnetization in the +r direction, and a bottom ring magnet segment stacked below the central ring segment in the −z direction and disposed radially outwardly from the bottom disk-cone magnet segment in the +r direction, wherein the top ring magnet segment has a magnetization in the −r direction, wherein the superimposition of the magnetic fields generated by each magnet segment generates the near spatially-uniform static magnetic field ($B_0$) across the bore along the axis of symmetry; and a shimming apparatus configured to provide a spatial magnetic field correction to the near spatially-uniform static magnetic field.

In at least one of these embodiments, the uniform static magnetic field ($B_0$) generated across the magnet bore is greater than about 1.5 Tesla.

In at least one of these embodiments, the uniform static magnetic field ($B_0$) generated across the bore is between about 1.5 Tesla and about 2 Tesla.

In at least one of these embodiments, the uniform static magnetic field ($B_0$) has a field uniformity of less than about 0.1 ppm.

In at least one of these embodiments, the static magnetic field ($B_0$) has a field uniformity of substantially 0.01 ppm.

In at least one of these embodiments, the permanent magnet is characterized by three-dimensional confinement of the 5 Gauss field line.

In at least one of these embodiments, each magnet segment of the permanent magnet assembly is formed of a hard-permanent magnetic alloy which allows the superimposition of the magnetic field generated each magnet segment in the permanent magnet assembly.

In at least one of these embodiments, the hard permanent magnetic allow is neodymium (NdFeB).

In at least one of these embodiments, the central ring magnet segment is formed of N40 grade NdFeB to counteract a high reverse coercive field, and wherein the top and bottom top ring magnet segments are formed of N40 grade NdFeB to provide optimal field confinement.

In at least one of these embodiments, an inner surface of the central ring magnet segment facing the bore includes a corrective magnet segment which is curved radially inwardly and which is configured to improve the uniformity of the a near spatially-uniform static magnetic field ($B_0$) generated across of the bore.

In at least one of these embodiments, the corrective magnet segment is a pole piece formed from high permeability soft steel.

In at least one of these embodiments, the shimming apparatus is powered by an lithium ion (Li-Ion) battery.

In at least one of these embodiments, the portable nuclear magnetic resonance (NMR) device is provided in a compact and portable form adapted for a household environment and is adapted to encourage diabetic patients, as well as other patients suffering from other metabolite disorders, to use the device more frequently, thereby facilitating frequent glucose or other metabolite testing.

In accordance with another broad aspect of the teachings herein, there is provided at least one embodiment of a shimming apparatus configured to provide a spatial magnetic field correction to the near spatially-uniform static magnetic field, wherein the shimming apparatus comprises: a plurality of linear current carrying conductors arranged in a circular configuration and wherein the plurality of linear current carrying conductors are uniformly spaced around a circumference of the circular configuration.

In at least one of these embodiments, each of the plurality of linear current carrying conductors is driven by a respective DC current, and wherein each of the plurality of linear current carrying conductors has a uniform density.

In at least one of these embodiments, a current distribution of the respective DC currents of the plurality of linear current carrying conductors is a sinusoidal distribution of DC currents which varies according to an angular position of the linear current carrying conductor around the circumference of the circular configuration, and wherein the shimming apparatus is configured to generate high order shim modes.

In at least one of these embodiments, the near spatially-uniform static magnetic field is expressible as a first $n^{th}$ order polynomial having n first coefficients, the plurality of linear carrying conductors contains m linear current carrying conductors, wherein each linear current carrying conductor of the m linear current carrying conductors carries a current having an amplitude that is a superposition of n current modes, where each current mode primarily corresponds to a term in the first $n^{th}$ order polynomial.

In at least one of these embodiments, the spatial magnetic field correction generated by the shimming apparatus is expressed as a second $n^{th}$ order polynomial having n second coefficients which correspond to the amplitudes of the modal currents required to produce a desired compensatory nth order $B_0$ field polynomial, wherein there is a linear relationship between the n first coefficients and the n second coefficients.

In accordance with another broad aspect of the teachings herein, there is provided a shimming apparatus configured to provide spatial magnetic field correction for a static magnetic field having a near spatially-uniform profile, wherein the shimming apparatus comprises first and second sets of concentric current carrying conductors, wherein: each concentric carrying conductor, of the first set of concentric current carrying conductors, is spaced from and arranged opposite to, along an axis of the static magnetic field, a corresponding concentric current carrying conductor, of the second set of current carrying conductors, to form a plurality of current carrying conductor pairs wherein each current carrying conductor generates a compensatory magnetic field for correcting the near spatially-uniform profile of the static magnetic field.

In at least one of these embodiments, each of the plurality of current carrying conductors is driven by a respective DC current.

In at least one of these embodiments, at least one current carrying conductor pair is configured such that a coil radius, of each coil in the current carrying conductor pair, is substantially equal to the spacing between the coils of the conductor pair, and thereby satisfies a Helmholtz condition and the conductor pair generates a linear field gradient between coils of the conductor pair.

In at least one of these embodiments, the plurality of current carrying conductors are coupled to a DC-DC converter, the DC-DC converter being configured to step-up current from a DC power source to boost current to each of the plurality of current conductors, whereby the DC-DC converter allows for varying the shimming capability of each current carrying conductor in order for the shimming apparatus to provide greater spatial magnetic field correction to the static magnetic field.

In at least one of these embodiments, the current carrying conductors, within each of the first and second sets, are offset from each other, and the offset is in a range between approximately 10 degree and 45 degree offset.

In at least one of these embodiments, each of the first and second sets of concentric current carrying conductors are arranged in a disk configuration, and the disk configuration has a disk radius, and wherein each current carrying conductor has a diameter that is less than the disk radius.

In at least one of these embodiments, each of the first and second sets of concentric current carrying conductors are arranged in a disk configuration, and the disk configuration has a disk radius, and wherein each current carrying conductor has a diameter that is approximately equal to the disk radius.

In at least one of these embodiments, the shimming apparatus is configured to produce spatial magnetic field correction for a static magnetic field that varies with azimuthal angle.

In at least one of these embodiments, each of the first and second sets of current carrying conductors comprise a plurality of nested current carrying conductors, each current carrying conductor having a center point that is collinear with the axis of the static magnetic field ($B_0$).

In at least one of these embodiments, the magnetic field generated by each current carrying conductor is expressed using a polynomial expansion in spherical harmonics, and wherein each current carrying conductor generates both even and odd polynomial terms.

In at least one of these embodiments, current carrying conductors having different radii generate polynomial coefficient vectors that are linearly independent allowing any desired compensatory field with azimuthal symmetry to be produced within a volume of a magnet bore of an axisymmetric permanent magnet assembly which generates the static magnetic field in the magnet bore.

In accordance with another broad aspect of the teachings herein, there is provided at least one embodiment of a method for in-vivo and non-invasive quantitation of the concentration of a small molecule metabolite in a sample using a portable nuclear magnetic resonance (NMR) device, the method comprising: selecting, from a plurality of resonance features associated with the metabolite, a sub-set of high resolution resonance features; applying a uniform static magnetic field ($B_0$) to induce magnetization of the sample; applying a first RF stimulus pulse ($B_1$) to the sample, wherein the first RF stimulus pulse ($B_1$) is applied at a frequency range that includes at least one Larmor frequency associated with a resonance feature of the sub-set of high resolution resonance features; and detecting a free induction delay (FID) signal generated by the sample.

In at least one of these embodiments, the small molecule metabolite comprises at least one of: glucose, glycogen, BHB, and ketoacidosis markers.

In at least one of these embodiments, a magnetic resonance velocimetry (MRV) technique is used to distinguish small molecule metabolites flowing in blood from stationary small molecule metabolites.

In at least one of these embodiments, the sub-set of high resolution resonance features are characterized by high signal-to-noise ratio (SNR).

In at least one of these embodiments, the plurality of resonance features associated comprise a plurality of chemical shift resonances associated with the metabolite.

In accordance with another broad aspect of the teachings herein, there is provided at least one embodiment of a compact portable NMR device comprising: a housing that provides a magnetic shield; a permanent magnet assembly disposed within the housing and having a bore along a portion of a longitudinal axis of the permanent magnet assembly, the permanent magnet assembly having a plurality of magnetic elements that together provide an axisymmetric magnetization for generating a near-homogenous magnetic field $B_0$ directed along the longitudinal axis and one of the magnet elements having a sample cavity that is sized to receive a sample; a hollow frame disposed between the permanent magnet assembly and the housing and provides an internal space; a shimming assembly with coils disposed at the longitudinal axis for providing a spatial magnetic field correction to the near homogenous magnetic field $B_0$; and a spectrometer disposed within the hollow space of the frame and coupled to the magnetic bore, the spectrometer having a control unit for applying magnetic stimulus pulses to the sample and measuring free induction delay signals generated by the an ensemble of hydrogen protons within the sample.

In at least one of these embodiments, the housing is sized to be held in a table-top cradle, and the sample cavity is sized to receive a sample insert that holds the sample.

In at least one of these embodiments, the housing is sized to be gripped by a subject's hand, the sample is provided by the subject's finger or thumb and the sample cavity is sized to receive a finger of the subject.

In at least one of these embodiments, the device further comprises a sliding door to selectively allow access to the sample cavity during measurement.

In at least one of these embodiments, the device further comprises a touch sensor that can be touched to activate the device.

In at least one of these embodiments, the device further comprises a display to provide a user interface and to display measurement results.

In at least one of these embodiments, the device further comprises a communication module for allowing the control unit to communicate and receive control data and measurement results with a remote device.

In at least one of these embodiments, the control unit is configured to perform one of the methods described in accordance with the teachings herein including, but not limited to, one of a method for in-vivo and non-invasive quantitation of glucose concentration in a sample using a portable NMR device, a method for in-vivo and non-invasive quantitation of the concentration of a small molecule metabolite in a sample using a portable NMR device or a method for performing NMR spectroscopy on a sample using a portable spectrometer.

In at least one of these embodiments, the spectrometer, the permanent magnet assembly and the shimming apparatus is defined in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1A:
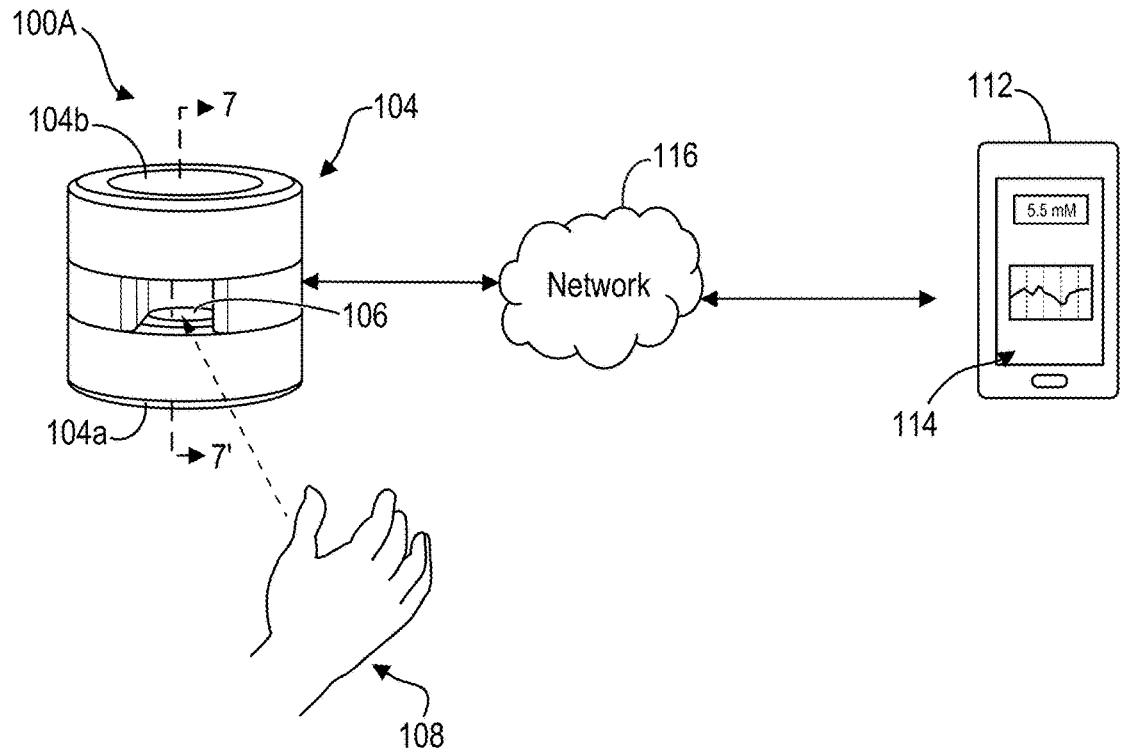
FIG. 1A shows an example embodiment of an in-vivo, and non-invasive metabolite testing system which includes a portable nuclear magnetic resonance (NMR) device.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the example embodiments described herein.

It should also be noted that the terms "coupled" or "coupling" as used herein can have several different meanings depending in the context in which these terms are used. For example, the terms coupled or coupling can have a mechanical, fluidic or electrical connotation. For example, as used herein, the terms coupled or coupling can indicate that two elements or devices can be directly connected to one another or connected to one another through one or more intermediate elements or devices via an electrical or magnetic signal, electrical connection, an electrical element or a mechanical element depending on the particular context. Furthermore, coupled electrical elements may send and/or receive data.

Unless the context requires otherwise, throughout the specification and claims which follow, the word "comprise" and variations thereof, such as, "comprises" and "comprising" are to be construed in an open, inclusive sense, that is, as "including, but not limited to".

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

The headings and Abstract of the Disclosure provided herein are for convenience only and do not interpret the scope or meaning of the embodiments.

Similarly, throughout this specification and the appended claims the term "communicative" as in "communicative pathway," "communicative coupling," and in variants such as "communicatively coupled," is generally used to refer to any engineered arrangement for transferring and/or exchanging information. Examples of communicative pathways include, but are not limited to, electrically conductive pathways (e.g., electrically conductive wires, electrically conductive traces), magnetic pathways (e.g., magnetic media), optical pathways (e.g., optical fiber), electromagnetically radiative pathways (e.g., radio waves), or any combination thereof. Examples of communicative couplings include, but are not limited to, electrical couplings, magnetic couplings, optical couplings, radio couplings, or any combination thereof.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

The example embodiments of the systems and methods described herein may be implemented as a combination of hardware or software. In some cases, the example embodiments described herein may be implemented, at least in part, by using one or more computer programs, executing on one or more programmable devices comprising at least one processing element, and a data storage element (including volatile memory, non-volatile memory, storage elements, or any combination thereof). These devices may also have at least one input device (e.g. a keyboard, mouse, touchscreen, or the like), and at least one output device (e.g. a display screen, a printer, a wireless radio, or the like) depending on the nature of the device.

As mentioned in the background section, conventional techniques for measuring metabolite levels in blood samples are often invasive, in-accurate, and non-repeatable. Current blood glucose measurement technology, for example, requires puncturing a subject's skin with a lance to deposit a small sample of blood on a biochemically reactive, disposable, and single-purpose test strip. Each blood sample requires a new deposit. The inconvenience of repeatedly puncturing the skin, as well as the cost burden associated with purchasing new test strips for each batch of samples, often becomes an impediment to frequent glucose testing. This is particularly concerning for individuals who suffer from Type 1 diabetes, or advanced stages of Type 2 diabetes, and who require frequent testing to insure proper insulin dosing decisions.

Current glucose testing technology also suffers from measurement inaccuracy. On average, glucose measuring test strips have an error range of between 5% and 20%, at a 0.95 statistical confidence. This inaccuracy often results from manufacturing tolerances, as well as external influences which affect the test strip's electrochemical reaction (e.g. temperature, humidity, altitude, hematocrit levels, and the presence of common drugs). It is believed that a glucose meter measurement error of less than +/−2% at a 0.95 statistical confidence is required to adequately minimize insulin dosing decision errors, and in turn, avoid diabetic disease progression and increased risk of diabetes related diseases (e.g. heart disease, kidney disease, and other diabetes related diseases) (see e.g. J. C. Boyd and D. E. Bruns [1]).

The sharing between users of blood glucose test lances for puncturing the skin has also been linked to infections. Outbreaks of Hepatitis B in healthcare facilities have been traced back to the sharing of test lances, an unsafe practice also reported at public health fairs where glucose test services are provided.

Attempts at developing an alternative non-invasive glucose meter have been largely unsuccessful, and have otherwise been clinically unviable. By way of example, some attempts have used optical measurements, including Raman or near-infrared spectroscopy, to detect the concentration of glucose in circulating blood. However, these attempts have been largely ineffective because of the inability of light to penetrate the skin deeply. Further, the reflected or transmitted light (i.e., used to measure glucose concentration) often lacks enough spectral resolution to differentiate glucose from the many glucose-like molecules in the body, such as glycated proteins. Other attempts, which have relied on microwave and thermal spectroscopy, have also been ineffective for similar reason.

In embodiments described herein, there is provided a nuclear magnetic resonance (NMR) device (also referred to as a magnetic resonance spectroscopy (MRS) device) which may be used for repeated, non-invasive, and non-destructive testing of various common metabolites in a subject or a test sample. The ability of the NMR device to measure and quantitate a wide range of metabolites allows the device to find broad application in management of various metabolic disorders (e.g. diabetes), as well in clinical research.

In various embodiments, the NMR device may be provided as a portable device which is available in a convenient, compact, and easily transportable form and is adapted for every-day consumer application. The portable device may perform repeated in-vivo or in-vitro metabolite measurements by scanning a subject's finger, or a test blood sample, received inside a side bore (or cavity) of the device. In particular, by scanning a subject's finger (rather than puncturing the skin), as well as disposing with the requirement to purchase new single-purpose test strips with each measurement, patients are encouraged to frequently use the portable NMR device for metabolite level monitoring.

In one example application, the portable NMR device is configured to perform glucose testing and return glucose concentration results with measurement uncertainty of less than +/−2% at a 0.95 statistical confidence. This level of accuracy ensures insulin dosing decision errors are minimized and glycemic control in diabetic patients is improved.

In at least some embodiments, the NMR device is configured to provide metabolite level measurements at high accuracies using only one or two scans of a subject's finger, or a test sample, and to provide results within a competitive time frame of between 5 to 12 seconds.

In particular, and as described in further detail herein, the portable NMR device is operable to provide high measurement accuracy by employing a novel and compact axisymmetric segmented permanent magnet assembly that applies a strong and near-spatially uniform static magnetic field across the bore (or cavity) which receives the subject's finger or test sample. The high field strength generated by the compact permanent magnet assembly allows the device to generate metabolite level measurements with high signal-to-noise ratio (SNR). In at least one embodiment, the permanent magnet assembly can generate static magnetic field strengths of greater than 1.5 Tesla, but less than 2 Tesla (in order to comply with various consumer safety regulations). In at least some embodiments, the strength of the static field generated by the permanent magnet assembly is at least 1.68 Tesla, which represents an improvement over current compact permanent magnet assemblies used in NMR applications.

In embodiments described herein, the near-uniform static field generated by the permanent magnet assembly is corrected by a shimming assembly that corrects uniformity of the static field to less than 0.1 ppm (parts per million). In at least some cases, the shimming assembly may correct the uniformity of the static field to approximately 0.01 ppm. This level of field uniformity provides for high spectral resolution and allows for quantification of a wide array of metabolites with a high degree of statistical confidence. In various embodiments described herein, the shimming assembly requires precisely generated currents to effect the correction of the spatial non-uniformity of the static field to the target uniformity of approximately 0.01 ppm. The axisymmetric segmented permanent magnet design requires less shim current than traditional Halbach magnet designs with similar working volumes in the magnet bore because of its higher inherent $B_0$ field uniformity. In at least some cases, the lower current requirements for the shimming assembly allow the shimming assembly to be driven by a small power source which may be disposed inside of the portable NMR device.

The proposed axisymmetric permanent magnet assembly also demonstrates improved three-dimensional field confinement properties. More particularly, the permanent magnet is characterized by confinement of the 5 Gauss field line and is otherwise compatible for every-day consumer application.

Previous attempts at developing portable NMR devices have faced challenges in developing a permanent magnet architecture which similarly generates sufficient static field strength and field uniformity to produce measurements having sufficient accuracy, while satisfying field confinement regulations. For example, large and complex magnet designs have often been used to generate strong magnetic fields, but are otherwise incompatible for local and clinical use. Where smaller and more compact permanent magnet assemblies have been employed (e.g. Halbach cylinder magnet designs), these magnet assemblies have generated static fields with poor field uniformity which require strong shimming assemblies with current demands that cannot be provided by a small and portable power source.

In various embodiments also described herein, the portable NMR device uses transmission and receiver coils to generate and receive RF stimulus fields ($B_1$). These coils are incorporated into passive band pass filters. The passive band filters are devoid of tunable circuit elements which generate noise and otherwise comprise measurement accuracy. The band pass filters also allow for simplified control and filtering of transmitted and received frequency signals.

In accordance with teachings provided herein, the portable NMR device also uses a spectrometer receiving unit which generates signals with low signal-to-noise (SNR) ratio. In various cases, the receiving unit has a low noise design characterized by noise of less than 1.1 nV/√Hz as referred to input (RTI). The receiver unit is able to generate low noise and high SNR output signals by employing a combination of a low noise amplifier, a local oscillator, an automatic gain controller, and a high resolution analog-to-digital converter. The low noise design of the receiving unit contributes to the portable NMR device generating measurements with high statistical confidence.

In an example application, the portable NMR device may be used to detect blood glucose concentration by measuring the resonance peaks generated by the alpha and beta anomer $^1CH$ hydrogen group protons in a subject's circulating blood or in a test blood sample. In at least some embodiments, measuring the alpha and beta anomer resonance peaks is achieved by using a novel method which combines water signal suppression, homo-nuclear decoupling, and one-to-one mapping of the alpha and beta anomers concentrations to spectral peaks generated in an NMR frequency spectrum plot. In some cases, the method may also include a magnetic resonance velocimetry (MRV) technique to distinguish between resonance peaks generated by glucose molecules located in circulating blood and resonance peaks generated by glucose molecules located in a subject's tissue.

Referring now to FIG. 1A, there is shown an example embodiment of an in-vivo and non-invasive metabolite testing system 100A. The metabolite testing system 100A includes a portable NMR device 104 for conducting metabolite level measurements. In particular, the portable NMR device 104 provides for a convenient, compact, low-cost and higher accuracy alternative to conventional instruments which measure metabolite levels. As such, the portable NMR device 104 may find application in every-day consumer use (e.g. in a household environment) instead of just institutional or laboratory settings.

In at least one example application, the NMR device 104 may be used to measure vital metabolite levels for diabetic patients, including glucose, glycogen, beta-hydroxybutyrate (BHB), and ketoacidosis markers. As previously mentioned, by providing the NMR device 104 in a compact and portable form adapted for a household environment, so that diabetic patients, as well as other patients suffering from other metabolite disorders, may be encouraged to use the device more frequently, thereby facilitating frequent glucose or other metabolite testing.

In other example applications, the portable NMR device 104 may be used, inter alia, for performing at least one of drug dosing measurements, blood alcohol level measurements, opioid detection and quantification, glucose monitoring in severe burn intensive care units, metabolite level monitoring for management of metabolic disorders (e.g. PKU, IBS). Measurements of these metabolites may be made, in various cases, separately or simultaneously with measurements of glucose concentration levels.

Still referring to FIG. 1A, the portable NMR device 104 includes a magnet assembly having a magnet bore 106 (otherwise referred to as a bore, a cavity, a bore cavity, or a magnet cavity) which receives a subject's finger (e.g. thumb), or a blood test sample. As illustrated, the bore 106 is generally located on a lateral side of the portable NMR device 104. In at least some embodiments, the portable NMR device 104 may be designed with a cylindrical shape and a vertical axis of symmetry to allow a subject to position their thumb inside of the bore 106 while wrapping their fingers around the outer-surface of the device. To this end, the device 104 may be designed with symmetry in order to accommodate users who are either right-handed or left-handed. In at least some cases, the portable NMR device 104 may also have a flat bottom surface 104a, or a flat top surface 104b, such that the device is easily situated over a flat or planar surface (e.g. a household counter-top). In other embodiments, the outer housing of the portable NMR device 104 may be non-circular.

With the subject's finger, or test sample, received inside of the magnet bore 106, the portable NMR device 104 may conduct in-vivo (or in-vitro) and non-invasive metabolite testing in accordance with the teachings herein. The results of the testing may be transmitted by the portable NMR device 104 to a remote device 112 over a network 116. The remote device 112 may be associated with the user (or subject) who is using the NMR device 104, or alternatively, with a third party which is monitoring the metabolite levels of the subject or user (e.g. a medical practitioner). The remote device 112 may be, by way of non-limiting examples, a laptop, a computer terminal, a mobile device, a PDA, a tablet device, or a smart phone. The network 116 may be, for example, a wireless personal area network such as a Bluetooth™ network, a wireless local area network such as the IEEE 802.11 family of networks or, in some cases, a wired network or communication link such as a Universal Serial Bus (USB) interface or IEEE 802.3 (Ethernet) network, or others. Where the connection is a USB interface, the interface may be a USB-C interface which supports high speed data transfer and may also provide power to the portable NMR device 104.

In at least some cases, the portable NMR device 104 may communicate with the remote device 112 in real-time, or near real-time. In other cases, the NMR device 104 may store collected data in a memory device for later transmission to the remote device 112.

Upon receiving data from the portable NMR device 104, the remote device 112 may be configured to display the received results to a user on a display screen 114 of the remote device 112. In at least some example cases, an application may be installed on the remote device 112 which is configured to present (or display) the data received from the portable NMR device 104 to the user. The application may be, for example, an NMR spectral processing software program that is configured to both analyze the received data, as well as display one or both of the raw data and the analyzed or processed data to the user. In various cases, the application may also include a graphical user interface (GUI) which displays the results in a user-friendly manner.

Figure 1B:
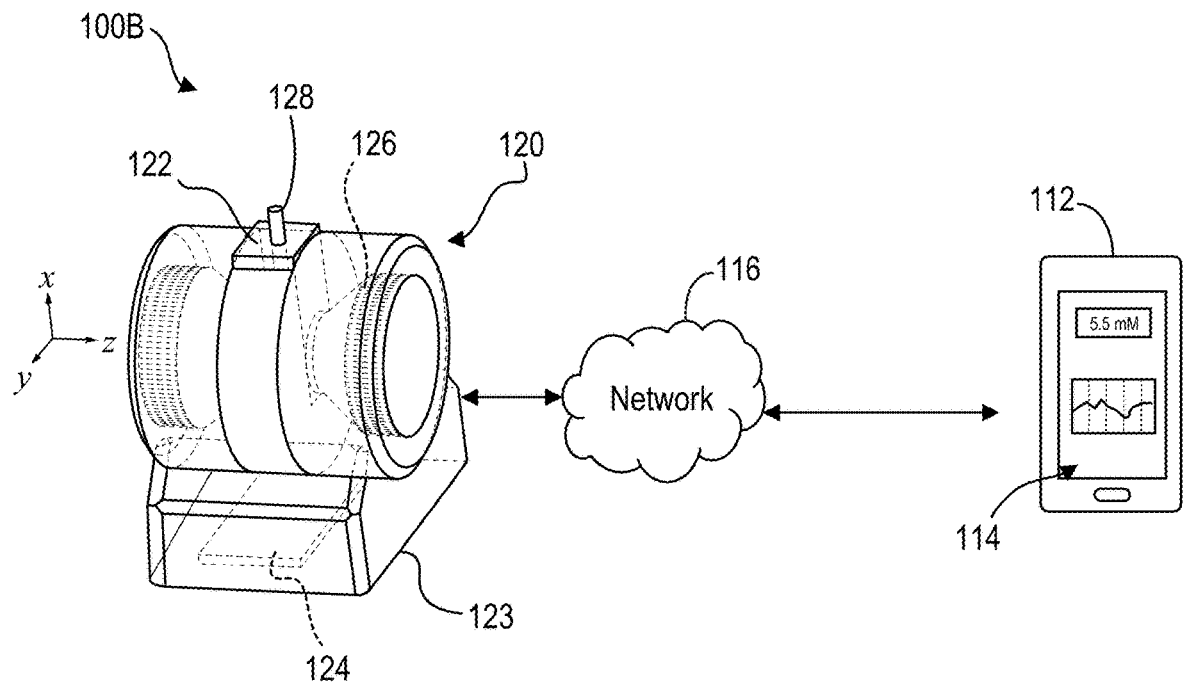
FIG. 1B shows an example embodiment of an in-vitro metabolite testing system which includes an NMR device which is adapted for a laboratory or institutional setting.

Referring now to FIG. 1B, there is shown an example embodiment of an in-vitro metabolite testing system 100B. The system 100B is analogous to the system 100A but is modified for laboratory or institutional application.

The system 100B includes an NMR device 120 in placement of the portable NMR device 104. In particular, the NMR device 120 has an upwardly facing magnet cavity 122 that is surrounded by a permanent magnet assembly 126. In various embodiments, the permanent magnet assembly 126 may have a horizontal axis of symmetry. The magnet cavity 122 receives a test sample 128 for in vitro laboratory testing. The test sample 128 may be, for example, a standard 5 mm diameter and 70 mm NMR test tube. A mechanical sample support may be located within the cavity 122 to support the test tube into the proper position for measurement by the NMR device 120. The NMR device 120 can also include a spectrometer 124 for receiving and processing NMR signals. In at least some cases, the spectrometer 124 can be located in a cradle base 123 of the NMR device 120. In other cases, the spectrometer can be a card inserted into a peripheral slot of a laboratory workstation and may require an extended connection (e.g. Ethernet cable) to connect to probes located in the NMR device. In various embodiments, the cradle base 123 has an upper surface that has a complimentary shape to the outer surface of the NMR device 120 to hold the NMR device 120 in a stable position. In at least some cases, a display screen (e.g., LCD screen) may be located on, or otherwise attached to, the cradle base 123. The display screen may be used, for example, to display raw or processed data obtained by the NMR device 120, or to otherwise enable a user to control the operation of the NMR device 120.

Referring now to FIGS. 2A to 2D, the general principles underlying the operation of the portable NMR device 104 of FIG. 1A will now be described herein by way of example. While the remainder of the discussion will focus on the portable NMR device 104 of FIG. 1A, it will be understood that the discussion applies equally to the NMR device 120 of FIG. 1B.

Figure 2A:
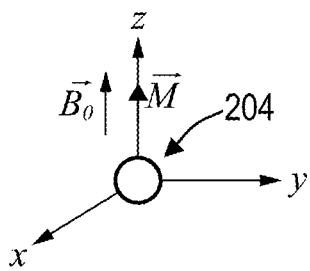
FIG. 2A shows an example hydrogen $^1$H proton after being exposed to a static magnetic field ($B_0$).

Referring first to FIG. 2A, there is shown an example $^1$H hydrogen proton (or nuclei) 204. The $^1$H hydrogen proton 204 may be located, for example, in a metabolite which is the subject of testing (e.g. measurement) by the portable NMR device 104. For instance, the $^1$H hydrogen proton may be located in a glucose compound disposed in a blood sample, within blood circulating within a subject's finger or within interstitial fluid of an ex-vivo or in-vivo sample.

The portable NMR device 104 operates by first applying a homogenous static magnetic field ($B_0$) across the magnet bore 106 such that the magnetic field direction is perpendicular to the longitudinal axis of the magnetic bore 106. The static magnetic field, as explained in further detail herein, is generated by a combination of a permanent magnet assembly and a shimming apparatus located within the portable NMR device 104.

In a simplified model, the static field ($B_0$) generated by the NMR device 104 polarizes the $^1$H hydrogen proton ensemble and causes a macroscopic vector magnetic moment to align with direction of the static field ($B_0$), which is conventionally defined along the z-axis.

A sample will include an ensemble of protons (or nuclei), each characterized by a separate magnetic moment. The vector sum of the magnetic moments, generated by each proton in the ensemble of protons, is expressed as a net magnetic moment ($M_0$). Accordingly, when the static field ($B_0$) is applied, the net magnetic moment ($M_0$) aligns with the direction of the static field ($B_0$). The net magnetic moment ($M_0$) of an ensemble of protons, under the influence of the static field ($B_0$), may be expressed according to Equation (1).

$$M_0 = \frac{N\gamma^2 \hbar^2}{4kT} B_0 \qquad (1)$$

In an example application where the static magnetic field ($B_0$) is applied to a sample containing glucose molecules, N defines the number of resonant hydrogen glucose protons in the sample (e.g., the number of alpha glucose hydrogen protons in a sample), γ is the gyromagnetic ratio for the magnetized $^1$H proton (2.68E+08 radians/(sec*Tesla), or 42.58 Hz/T), k is the Boltzman's constant (1.38e-23 Joules/Kelvin), and h is the reduced Plank's constant (1.05E-34 Joules*sec). If N is normalized per unit volume, then $M_0$ represents net magnetic moment per unit volume, or magnetization, in units of amperes per meter or A*m$^2$/L. If N is approximated to be 4.2E+18 protons within a sample received in the magnet bore 106 of the portable NMR device 104, and the static magnetic field ($B_0$) is approximately 1.68 T in accordance with embodiments described herein, then the net magnetic moment ($M_0$) is approximated to be 9.49E-08 A*m$^2$/L.

Once polarization is induced by the static field ($B_0$), the portable NMR device 104 applies a radiofrequency (RF) stimulus field ($B_1$) in a direction orthogonal to the static field ($B_0$) (e.g. in the XY plane). As explained in further detail herein, the RF stimulus field ($B_1$) may be generated by a set of transmission coils located within the portable NMR device 104.

In various embodiments, the RF stimulus field ($B_1$) is a circularly or elliptically polarized signal which is applied at an angular frequency configured to excite, or induce resonance, in specific types of protons (or nuclei) located within the sample. The specific angular frequency, at which the stimulus field ($B_1$) is applied, is also known as the "Larmor", or resonance angular frequency. As each type of proton (or nucleus) is generally excitable at a different Larmor frequency, an RF stimulus field ($B_1$) applied at one Larmor frequency may excite certain protons (or nuclei) while leaving other unperturbed. In particular, and as demonstrated by Equation (2), the Larmor angular frequency ($\omega_0$) is a function of both the gyromagnetic ratio of the proton and the strength of the static magnetic field ($B_0$).

$$\omega_0 = \gamma B_0 \qquad (2)$$

The Larmor frequency is also affected by a principle known as "chemical shifting". "Chemical shifting" results from localized shielding of the static field ($B_0$) at the proton by its molecular bonding environment and results in small frequency shifts in the Larmor frequency of that proton. For example, the Larmor frequency of a $^1$H hydrogen proton bonded to a glucose carbon atom is different from the Larmor frequency of a $^1$H hydrogen bonded to Lactate or water. Chemical shifts (δ) are reported in units of parts-per-million (ppm) and are expressed according to Equation (3):

$$\delta = \frac{f - f_{REF}}{f_{REF}} \cdot 10^6 \qquad (3)$$

where (f) is the resonant (or Larmor) frequency of the target proton, and $f_{REF}$ is the resonant (or Larmor frequency) of a standard reference ($f_{REF}$). The standard reference may be DSS (2,2-dimethyl-2-silapentane-5-sulfonate), while in other cases it may be water or another metabolite such as N-acetylaspartate (NAA).

As explained in further detail herein, the principle of chemical shifting is important to an application of the portable NMR device 104 in glucose concentration measurements. More specifically, chemical shifting allows the NMR device 104 to distinguish between $^1$H hydrogen protons bonded to known glucose carbon atoms, from $^1$H hydrogen protons bonded to other compounds (e.g. lactate, or water). Accordingly, the portable NMR device 104 may apply an RF stimulus field ($B_1$) at the Larmor frequency of the $^1$H hydrogen protons bonded to known glucose carbon atoms.

The effect of the RF stimulus field ($B_1$) applied at the resonance or Larmor frequency is to excite the proton, and in turn, off-set the angular alignment of its magnetic moment from the axis of the static magnetic field ($B_0$) (e.g. the z-axis) at an angular off-set known as a "nutation" or "tilt" angle. Longer and larger amplitude RF stimulus field ($B_1$) will result in larger misalignments of the magnetic moment (or net magnetization moment ($M_0$)) relative to the axis of the static magnetic field ($B_0$) (i.e., larger nutation or tilt angles). In particular, the nutation or tilt angle (a) generated by the RF stimulus field ($B_1$) may be expressed according to Equation (4):

$$\alpha = \gamma B_1 \tau \qquad (4)$$

wherein $\gamma$ is the gyromagnetic ratio, $B_1$ is the magnitude of the RF stimulus field ($B_1$), and $\tau$ is the duration of the stimulus field ($B_1$).

The off-setting of the magnetic moment also causes the magnetic moment to rotate around the axis of the static field ($B_0$) in a motion known as "precession", which occurs at the Larmor angular frequency. Generally, the precession of the magnetic moment can be decomposed into two vector components: (1) a longitudinal vector component ($M_z$), along the z-axis (or the axis of the static magnetic field ($B_0$)); and (2) a transverse vector component, in the XY plane ($M_{xy}$) (or the plane orthogonal to the axis of the static field). The transverse component ($M_{xy}$) rotates around the axis of the static field ($B_0$) sinusoidally at the Larmor angular frequency.

Figure 2B:
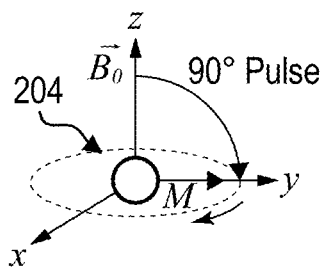
FIG. 2B shows the example hydrogen $^1$H proton of FIG. 2A after being exposed to a radiofrequency (RF) stimulus magnetic field ($B_1$) which rotates the magnetization of the hydrogen $^1$H proton onto the transverse plane.

Referring now to FIG. 2B, the vector magnetic moment of the $^1$H hydrogen proton has been offset by a 90 degree angle, into the transverse XY plane, as a result of the stimulus field ($B_1$). In this position, the magnetic moment has no longitudinal component ($M_z$), and the transverse component ($M_{xy}$) is precessing around the z-axis at the Larmor angular frequency.

Figure 2C:
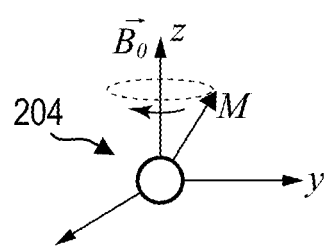
FIGS. 2C and 2D show the example hydrogen $^1$H proton of FIG. 2A relaxing back to equilibrium after the RF stimulus magnetic field ($B_1$) is removed.
Figure 2D:
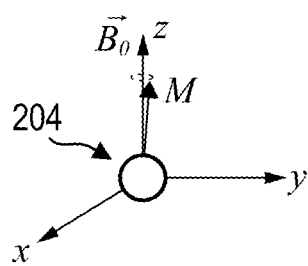

Referring now to FIGS. 2C and 2D, once the RF stimulus field ($B_1$) is removed, the magnetization moment gradually returns to equilibrium and re-aligns with the axis of the static magnetic field ($B_0$) in an energy-releasing process known as "relaxation".

Similar to the decomposition of the magnetic moment ($M_0$) during precession, relaxation also decomposes into two components: (1) a Spin-lattice relaxation (also referred to as longitudinal relaxation, or T1 relaxation); and (2) a Spin-spin relaxation (also referred to as transverse relaxation, or T2 relaxation).

Spin-lattice relaxation (T1) describes the gradual re-growth of the longitudinal magnetic component ($M_z$) during re-alignment with the axis of the static field ($B_0$). Conversely, Spin-spin relaxation (T2) describes the decay of the transverse magnetic component ($M_{xy}$) during re-alignment with the axis of the static field ($B_0$).

In particular, the energy released during T2 relaxation generates a Free Induction Delay (FID) signal, or a magnetic resonance signal. The FID signal is a sinusoidal signal, oscillating at the Larmor frequency, and at the decay rate of the transverse magnetic component ($M_{xy}$). To this end, the FID signal is generally characterized by a decaying exponential envelope which decays at a T2 time constant. In various cases, the T2 relaxation may also incorporate T2* relaxation. T2* denotes the real (or effective) relaxation that results from external factors, such as the non-uniformity of the static magnetic field ($B_0$). T2* relaxation shortens (or dampens) the free induction decay signal.

Figure 2E:
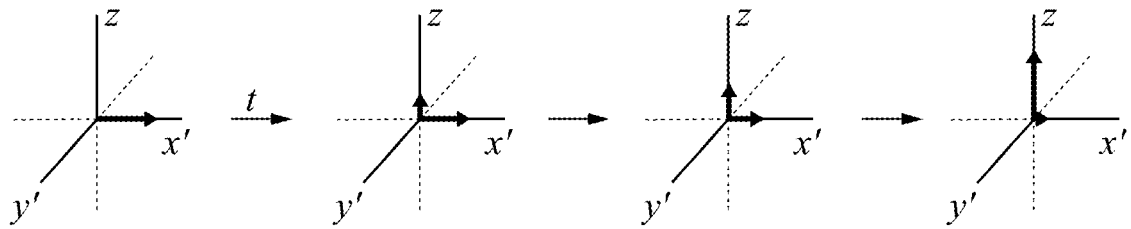
FIG. 2E shows a simplified illustrative model of T1 and T2 relaxations.

Referring now briefly to FIG. 2E, there is shown a largely simplified model of T1 and T2 relaxations. As shown, the net magnetic moment begins entirely in the transverse plane after the proton is excited at a 90° degree angle. As the magnetic moment returns to equilibrium, the vector component along the z-axis ($M_z$) gradually increases (i.e., T1 relaxation), and the vector component in the XY plane ($M_{xy}$) gradually decays to zero (i.e., T2 relaxation). The growth of the longitudinal component ($M_z$), and the decay of the transverse components ($M_x$) and ($M_y$) may be expressed according to Equations (5), (6), and (7):

$$M_z(t) = M_o\left(1 - e^{\frac{-t}{T_1}}\right) \qquad (5)$$

$$M_x(t) = M_o\cos(\Omega t)e^{\frac{-t}{T_2}} \qquad (6)$$

$$M_y(t) = M_o\sin(\Omega t)e^{\frac{-t}{T_2}} \qquad (7)$$

wherein $\Omega = \omega_0 - \omega$ is the angular rotation offset frequency, T1 is a time constant for the growth of the longitudinal component ($M_z$), and T2 is a time constant for the decay of the transverse component ($M_{xy}$).

As indicated at least by Equations (6) and (7), the $M_x(t)$ and $M_y(t)$ components of the FID signal are 90 degrees out of phase. Accordingly, the combined vector components of $M_x(t)$ and $M_y(t)$ (e.g., $M_{xy}$) resolve as a circularly polarized FID signal.

Figure 2F:
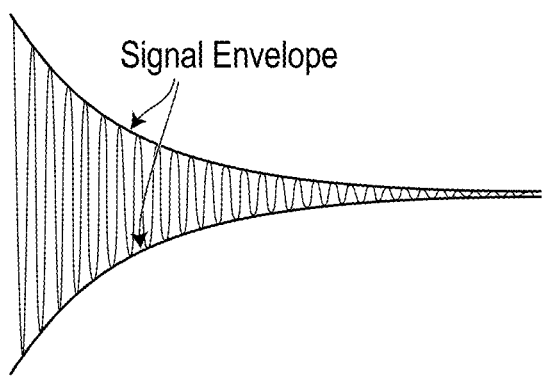
FIG. 2F shows a plot of an example decaying free induction delay (FID) signal which is generated as a result of T2 relaxation.

Referring now briefly to FIG. 2F, there is shown an example plot 200F showing an example FID signal which is generated as a result of T2 relaxation. As shown, the FID signal is expressed by a decaying envelope at the T2 time constant.

In the embodiments described herein, metabolite levels are generally measured by measuring the FID signal as an induced alternating-current voltage across a set of receiver coils located within the magnet bore 106 of the portable NMR device 104. In particular, the voltage amplitude of the magnetic resonance or FID signal $S_{emf}$ may be expressed according to Equation (8):

$$S_{emf} = \omega_0\left(\frac{n\mu_0}{2\sqrt{r^2 + l^2}}\right)M_0 V_s \qquad (8)$$

wherein n is the number of turns in the receiving coil solenoid, r is the radius of the turns in the receiving coil solenoid, l is one-half length of the receiving coil, $M_0$ is the spin angular magnetic moment per unit volume or magnetization in units of amperes per meter (as calculated above), $V_s$ is the sample volume, and $\mu_0$ is a constant for the permeability of free space (1.26E-06 T*m/A=H/m). In at least some embodiments described herein, the portable NMR device 104 is configured to generate a magnetic static field of 1.68 T, receive a sample volume ($V_s$) of about $3.5 \times 10^{-6}$ m$^3$ in the magnet bore 106, and employ a receiver coil having 10 turns, a 0.012 meter radius, and a coil half-length of 0.0150 meters. Under these parameters, the received voltage amplitude of the resonant signal will have an approximately 50 nV peak amplitude.

Equation (8) also indicates that the voltage of the magnetic resonance signal $S_{emf}$ is proportional to the square of the static magnetic field ($B_0$). This is because the Larmor angular frequency ($\omega_0$) and the magnetic moment ($M_0$), which are both included in Equation (8), are proportionally related to the static field ($B_0$) (see e.g., Equations (1) and (2)). Accordingly, a stronger static field ($B_0$) will generate a larger amplitude magnetic resonance signal $S_{emf}$, and by extension, a signal with a higher signal-to-noise ratio (SNR). In accordance with the teachings provided herein, the ability of the portable NMR device 104 to generate a static magnetic field greater than 1.5 T contributes to the ability of the device to generate high accuracy measurements with low SNR and using only one or two scans of a subject's finger or a test sample.

Figure 3A:
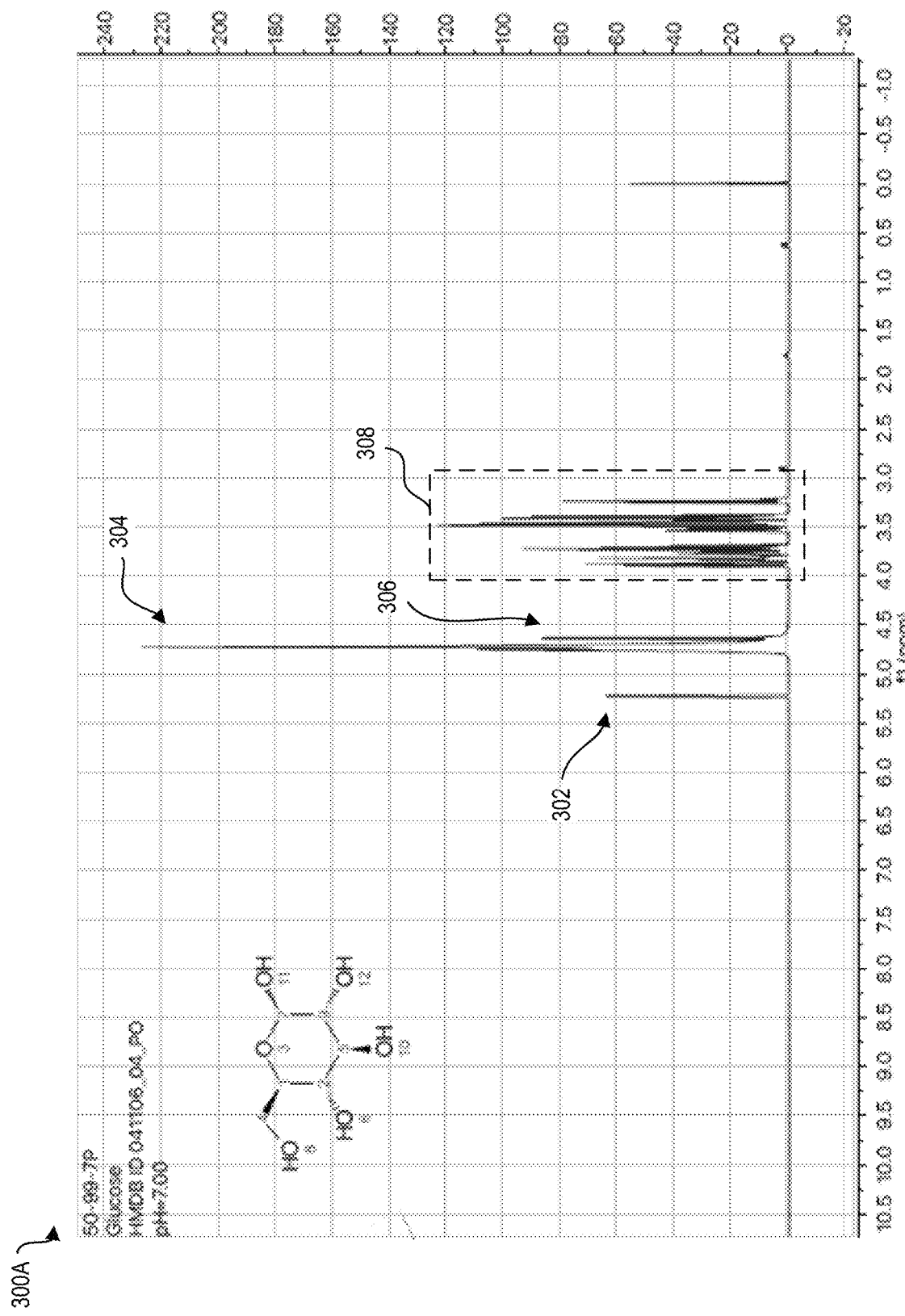
FIG. 3A shows an example nuclear magnetic resonance (NMR) plot which illustrates the Larmor frequencies of various $^1$H hydrogen protons located in a glucose molecule while taking into account each $^1$H hydrogen proton's chemical shift properties.

Referring now to FIG. 3A, there is shown an NMR spectrum plot 300A showing the Larmor frequencies of various $^1$H hydrogen protons located in (or bonded within) a glucose molecule, taking into account each proton's chemical shift properties. As explained in further detail herein, NMR spectrum plot 300A may be generated by measuring FID signals, produced by the T2 relaxation of each of the individual $^1$H hydrogen protons, and then converting the FID signals into the frequency domain.

As illustrated, a glucose molecule has twelve $^1$H hydrogen protons, each one having a different bonding environment. Of the twelve $^1$H hydrogen protons in a glucose molecule, only seven are directly visible to NMR (i.e., the RF transmit frequency in the FID signal is observable during relaxation) because the other five protons are in hydroxyl groups which are so-called "water exchangeable" and resonate at the same frequency as hydrogen protons in water molecules. Each of the seven visible glucose $^1$H hydrogen protons resonates at a distinct frequency. One component, the alpha-Glucose (α-Glc) anomer $^1$CH hydrogen group proton, is observed at 5.22 ppm at 302, distinct from water and other metabolite resonances by about 0.5 ppm. The resonance peak 304 at 4.72 ppm corresponds to the hydrogen protons located in water, while the reference signal at 0 ppm corresponds to DDS (2,2-dimethyl-2-silapentane-5-sulfonate). The peak 306 at 4.634 ppm corresponds to the beta-Glucose (β-Glc) anomer $^1$CH hydrogen group proton resonance, which is closely proximate to the water signal peak. In region 308, between 3 ppm and 4 ppm, the remaining glucose $^1$H hydrogen protons resonate with overlap with other metabolite protons.

Although the NMR spectrum plot 300A illustrates a one-to-one mapping of spectral lines to glucose hydrogen protons, in practice, a one-to-one mapping may not be possible due to a phenomena known as "homonuclear spin coupling", or "spin-spin coupling". Spin-spin coupling causes a single spectral line, associated with a single glucose hydrogen proton, to resolve into two or more spectral lines. More particularly, spin-spin coupling is generated by the magnetic interference generated from the spinning of nearby, or neighboring, hydrogen protons in a glucose molecule. As described in further detail herein, mitigating the effects of spin-spin coupling requires the application of spin-spin decoupling techniques.

In at least some embodiments, the portable NMR device 104 may determine blood glucose concentration by applying a one-to-one mapping of the seven visible hydrogen protons located in the glucose molecule to the corresponding resonance signal peaks in an NMR spectrum plot. The method applies a broadband spin-spin de-coupling technique which resolves multiple spectral lines, associated with one hydrogen proton, into a single spectral line. More particularly, to resolve glucose spectral lines between 3 ppm to 4 ppm from other metabolites (region 308), the portable NMR device 104 is configured for high spectral resolution and applies a static magnetic field having a uniformity of 0.01 ppm.

In other embodiments described in further detail herein, the portable NMR device 104 may also determine blood glucose concentration using only a one-to-one mapping of the alpha and beta anomer $^1$CH hydrogen group protons to the corresponding resonance signal peaks generated by these protons in an NMR spectrum plot. This method avoids the complexity of resolving many tightly proximate spectral lines, resulting from spin-spin coupling, in region 308. The portable NMR device 104 measures the resonance signal amplitudes of the alpha and beta anomers by applying a method of spin-spin decoupling which resolves doublet spectral lines (i.e., two peak spectral lines), of the alpha and beta anomers, into single spectral lines. As the beta anomer is closely proximate to the water signal, a method of water suppression is employed prior to exciting the alpha and beta anomer hydrogen protons to attenuate interference of the water signal in the measurement of the alpha and beta anomers in the spectral domain.

Measuring the resonance peaks of both the alpha and beta anomer hydrogen protons allows the NMR device 104 to generate measurements with a high statistical confidence of 0.95, and an accuracy (c) of +/−2% of the true level of blood glucose concentration (assuming a nominal mean blood glucose concentration of 5.5 mM (millimoles per liter)). A statistical confidence of 0.95 at an accuracy (ε) of +/−2% allows for accurate insulin dosing decisions, and represents an improvement over conventional finger stick glucose meters which achieve a 5% to 20% accuracy at a 0.95 confidence level. In particular, the portable NMR device is capable of generating measurements with this high level accuracy using only one or two scans of the subject's finger, or test sample, by the NMR device 104, and in a competitive time frame of under 12 seconds. In various embodiments, higher measurement accuracy and/or statistical confidence level is attainable where the blood glucose concentration is greater than 5.5 mM.

In accordance with the teachings herein, the statistical confidence (CL) of 0.95 is determined according to the error function expressed in Equation (9):

$$CL = \text{erf}\left(\frac{\varepsilon S_{emf}}{\sqrt{2\sigma_n^2 \Delta f}}\right) \tag{9}$$

where Δf is the measurement bandwidth used for metabolite quantitation $\sigma_n$ is the noise in the received signal, £ is the desired accuracy of the system (e.g., 0.02), and $S_{emf}$ is the voltage amplitude of the received magnetic resonance signal. (e.g., 60 nV).

Noise in the received signal ($\sigma_n$) in Equation (9) results primarily from the receiver electronics, which are the dominant source of noise. As explained in further detail herein, in order to achieve a confidence level of 0.95, the portable NMR device 104 uses receiver electronics which are configured to have a noise level ($\sigma_n$) equal to or less than 1.1 nV/√Hz, as referred to input (RTI). The noise in the received electronics is assumed to be spectrally uniform with a Gaussian-like amplitude distribution.

The measurement bandwidth Δf in Equation (9) is a function of the FID (or T2 relaxation) signal. An approximation for Δf in terms of the transient decay of the transverse T2 magnetization is expressed according to Equation (10):

$$\Delta f \cong \frac{1}{\pi T_2^*} \cong \frac{1}{\pi}\left(\frac{1}{T_2} + \gamma \Delta B_0\right) \quad (10)$$

wherein $\Delta B_0$ represents the root mean squared average of static field $B_0$ spatial inhomogeneity across the sample or the subject's finger. In order to achieve a statistical confidence of 0.95, the measurement bandwidth is minimized by using the method of homonuclear decoupling which reduces doublet spectral lines into single spectral lines which occupy a minimal frequency band.

The confidence level is also positively correlated with the voltage of the magnetic resonance signal ($S_{emf}$), which as stated previously, is proportional to the square of the static magnetic field ($B_0$). Accordingly, increasing the magnitude of the static magnetic field ($B_0$) generates measurements having higher statistical confidence. In various embodiments described herein, a static magnetic field ($B_0$) between 1.5 T and 2 T is employed in order to generate measurements having 0.95 confidence level.

It will be appreciated that measuring only the resonance peak of the alpha anomer is insufficient to achieving a statistical confidence level of 0.95 at an error of +/-2%.

Figure 3B:
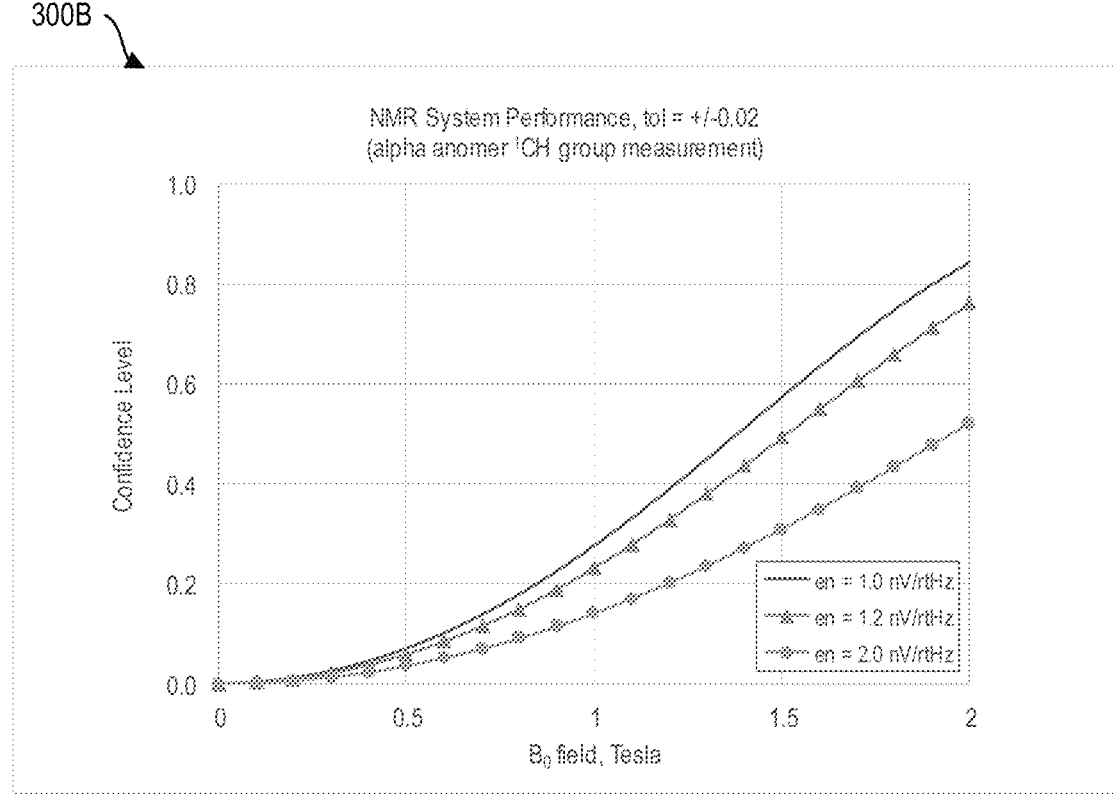
FIG. 3B shows a plot of the statistical confidence level of glucose concentration measurements using only the resonance peak generated by the alpha anomer glucose $^1$CH hydrogen group proton.

Referring now to FIG. 3B, there is shown a plot 300B of the statistical confidence level based on glucose concentration measurements of only the alpha anomer $^1$H hydrogen proton resonance. In particular, plot 300B shows the confidence level as a function of the strength of the static magnetic field and the measurement noise, as referred to the receiver input (RTI). The plot 300B assumes a nominal blood glucose concentration level of 5.5 mM.

As shown, at an error of +/-2%, only a 0.65 confidence level is achievable where the static magnetic field ($B_0$) strength is set at 1.68 T (e.g., under 2 T in order to comply with various consumer safety regulations) and the receiver noise is at a low value of 1 nV/√Hz (RTI). Even where the static magnetic field ($B_0$) strength is increased to a maximum of 2 T, the confidence level does not otherwise reach 0.95 statistical confidence (i.e., the confidence level is just over 0.8). Further, and in accordance with expectations, the confidence level decreases with higher receiver noise. For example, where the receiver noise is 1.1 nV/√Hz (RTI), and the static magnetic field ($B_0$) strength is set to a maximum of 2 T, the highest achieved confidence level is just under 0.8.

Accordingly, achieving a 0.95 confidence level at an error of +/-2% using only the alpha anomer is not otherwise feasible unless multiple measurements of the alpha anomer $^1$H resonance are obtained and averaged. In particular, averaging N measurements of the alpha anomer $^1$H resonance can improve measurement accuracy and signal-to-noise ratio (SNR) by a factor \IN. As each alpha anomer $^1$H measurement takes between 5 to 7 seconds (i.e., the $T_1$ relaxation time of the alpha anomer $^1$H), achieving the required error rate and confidence level within a competitive time frame of 12 seconds (i.e., the time required for current finger prick glucose testing to complete measurement) is not possible with only one or two measurements of the alpha anomer $^1$H resonance.

In addition, multiple consecutive measurements of the alpha anomer $^1$H resonance signal is effected by rotating the net magnetic moment of the alpha anomer $^1$H at the appropriate Ernst angle in order to ensure optimal SNR performance. The Ernst angle ($\alpha_E$) is generally expressed by Equation (11):

$$\alpha_E = \arccos\left(e^{-\frac{T_R}{T_1}}\right) \quad (11)$$

wherein $T_R$ is the scan repetition time, and T1 is the longitudinal relaxation time for the alpha anomer $^1$H. Where the scan repetition time TR is equal to T1 (i.e., in order to increase the number of measurements of the resonance signal within a given time interval), the optimal Ernst angle is approximately 68.4°, which improves measurement SNR by up to 10 decibels relative to where TR≥5T1 and at a 90° nutation angle. However, generating multiple consecutive measurements of the alpha anomer $^1$H resonance signal by rotating the net magnetic moment at the Ernest angle may also degrade the quantitation accuracy because a dependency is introduced between the measured free induction decay amplitude and the T1 relaxation time of the alpha anomer $^1$H proton.

Figure 3C:
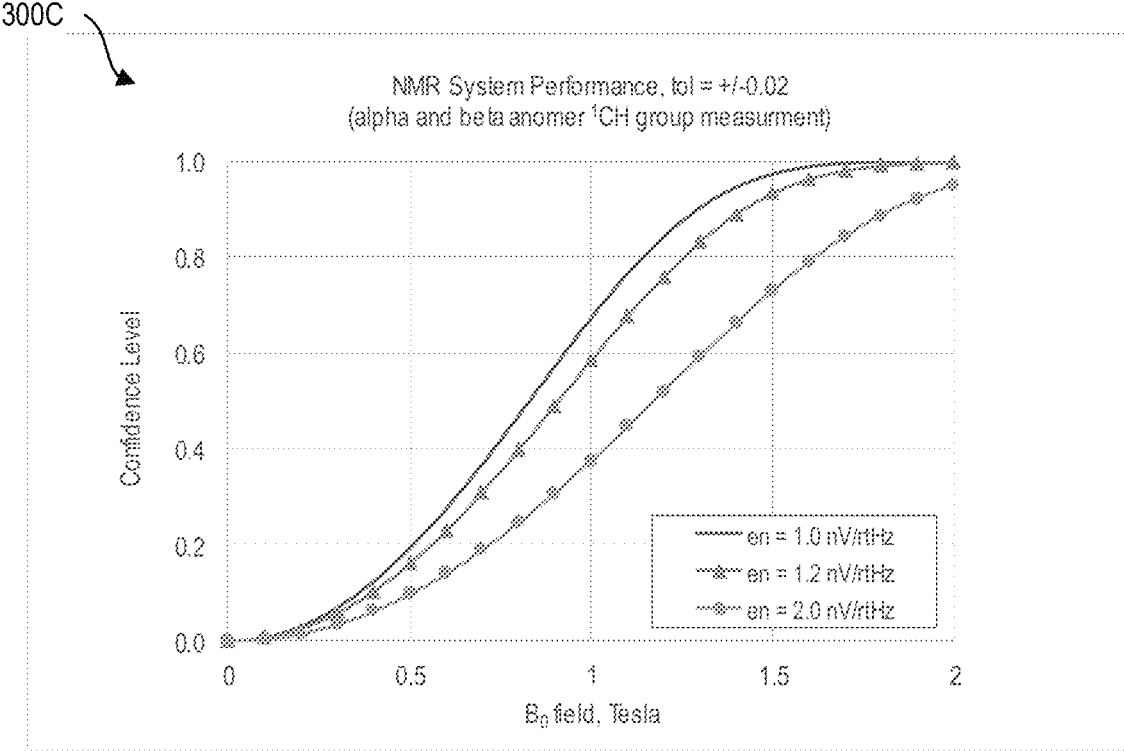
FIG. 3C shows a plot of the statistical confidence level of glucose concentration measurements using the resonance peaks generated by both the alpha and beta anomer glucose $^1$CH hydrogen group protons.

Referring now to FIG. 3C, there is shown a plot 300C of the statistical confidence level based on glucose concentration measurements of both the alpha and beta anomer $^1$H hydrogen proton resonances. In particular, plot 300C shows the confidence level as a function of the strength of the static magnetic field and the measurement noise, as referred to the receiver input (RTI). The plot 300C also assumes a nominal blood glucose concentration level of 5.5 mM.

As shown, at an error of +/-2%, a 0.95 confidence level is achievable where the receiver noise is below 1.2 nV/√Hz (RTI) and the static magnetic field ($B_0$) strength is set to at least 1.68 T. Accordingly, and in contrast to measurements relying only on the alpha proton resonance, measuring both the alpha and beta resonances allows for high accuracy measurements with high statistical confidence. In particular, these measurements may be obtained in a competitive time frame and using only one or two scans of a subject's finger or a test blood sample.

Figure 10:
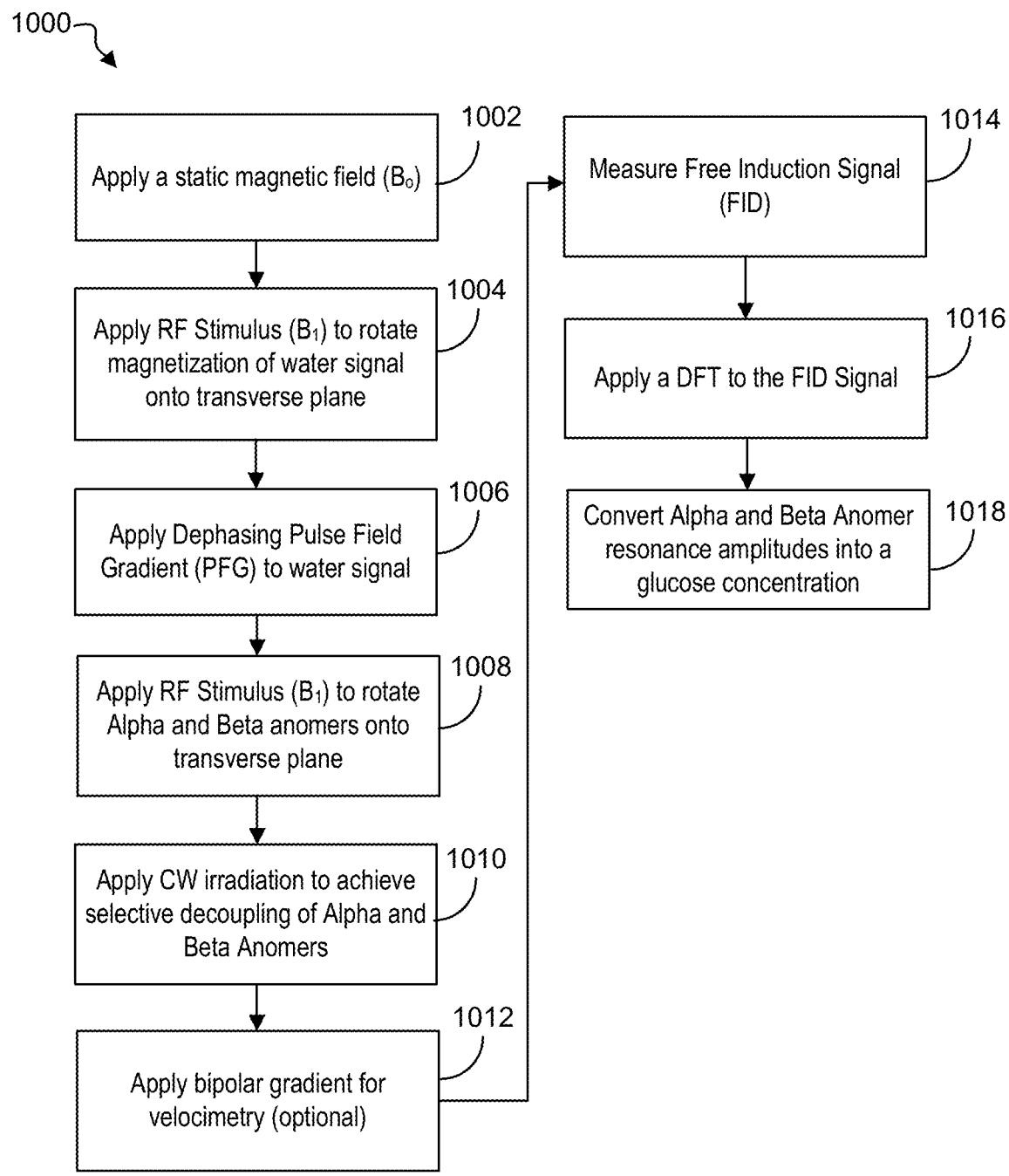
FIG. 10 is a flow chart of an example embodiment of a method for measuring blood glucose concentration based on the alpha and beta glucose anomer $^1$CH hydrogen group proton resonances.

Referring now to FIG. 10, there is shown an example process flow 1000 for a method for measuring blood glucose concentration based on the resonance peaks of the alpha and beta glucose anomer $^1$H resonances.

At act 1002, a static magnetic field ($B_0$) is applied to the subject's finger or test sample to induce polarization of the ensemble of nuclei located there within.

At act 1004 and act 1006, a method for suppressing the water signal is applied. In particular, as the beta anomer $^1$CH hydrogen proton resonance (δ=4.634 ppm) is proximate the spectral modulation sidebands generated by the water signal resonance peak (δ=4.72 ppm), exciting the beta anomer hydrogen proton risks also exciting the water hydrogen protons. This may cause the FID signal generated by the water signal to interfere with measuring the FID signal generated by the beta anomer hydrogen proton.

Accordingly, at act 1004, the method of water suppression includes first applying an RF stimulus pulse ($B_1$) to the subject's finger, or test sample, which rotates the magnetization of the hydrogen protons located in water onto the transverse plane. This is analogous to the process shown in FIG. 2B on a micro-scale. In various embodiments, rotating the magnetization of the water compound onto the transverse plane is effected by applying a long frequency selective pulse ($B_1$) at the water resonance frequency $f_{H2O}$ for a sufficient duration of time and magnitude.

In at least some embodiments, the long frequency selective pulse ($B_1$) is a continuous wave RF signal gated with a rectangular pulse, and centered at the water resonance frequency $f_{H2O}$. This RF stimulus pulse has a frequent domain excitation profile expressed by Equation (12):

$$|\sin c(\pi \Delta f \tau)| \qquad (12)$$

wherein $\Delta f$ is the offset frequency from the water resonance center frequency, and $\tau$ is the duration of the rectangular pulse calculated according to Equation (13):

$$\tau = (f_{H2O} - f_{\beta-glc})^{-1} \qquad (13)$$

wherein $f_{H2O}$ is the resonant frequency of the water protons and $f_{\beta-glc}$ is the resonant frequency of the beta anomer. Accordingly, by centering the pulse at the water resonant frequency, and defining the pulse duration ($\tau$) in relation to Equation (13), the beta anomer should be unperturbed (or unexcited) by the pulse.

Figure 3D:
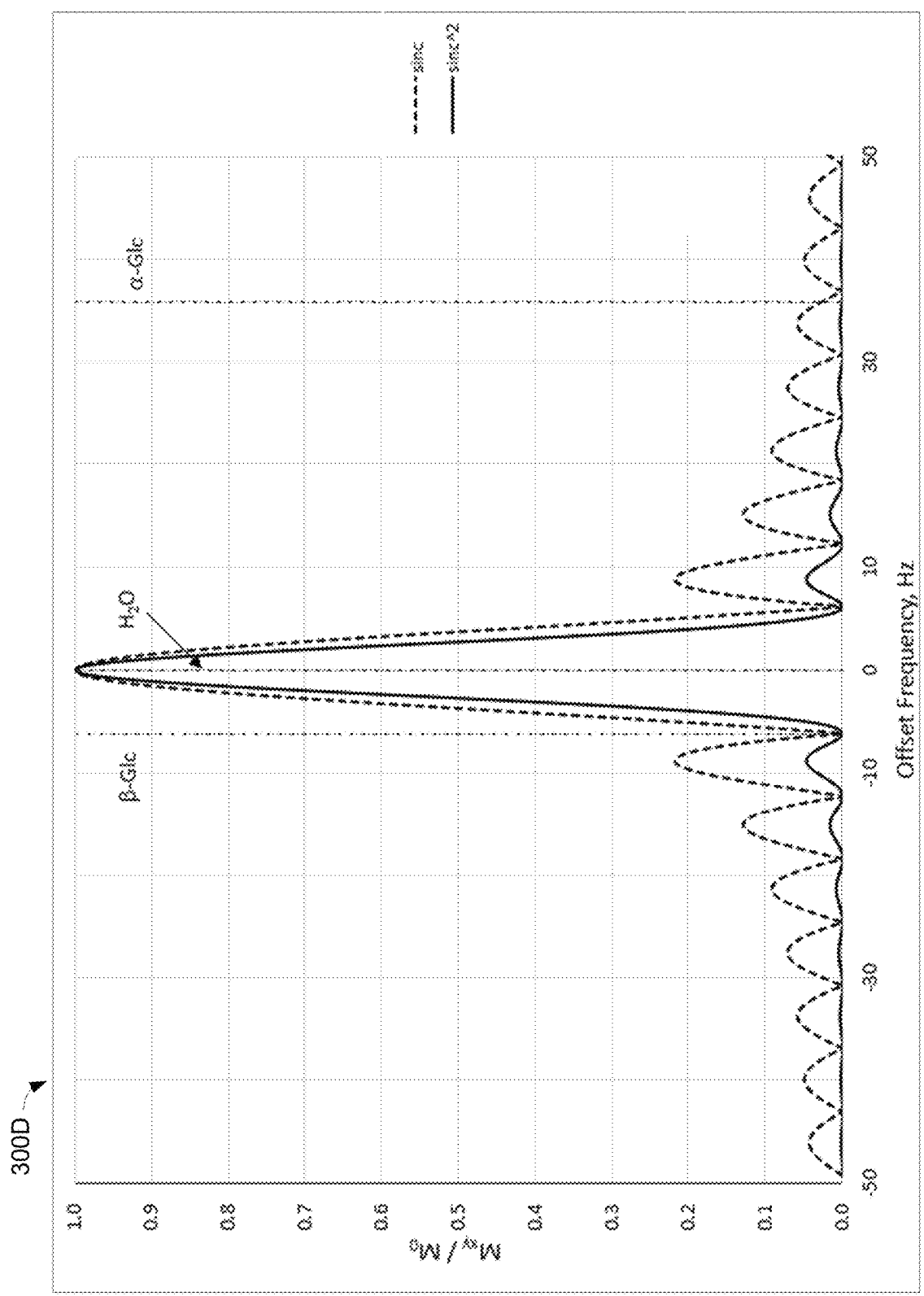
FIG. 3D shows a plot of an example magnitude frequency response after applying a frequency selective pulse for water signal suppression.

Referring now briefly to FIG. 3D, there is shown a plot 300D of the expected magnitude frequency response of the transverse magnetization ($M_{xy}$) normalized to the original longitudinal magnetization ($M_0$) after applying the frequency selective pulse ($B_1$).

As shown, the $|\sin c(\pi \Delta f \tau)|$ pulse, shown as a solid plot line, excites the water signal, while the chemical shift, for the beta glucose anomer $^1$CH group hydrogen proton, is located at a sin c null and is otherwise unperturbed. The chemical shift for the alpha anomer $^1$CH group hydrogen proton, while being close to a sin c null point, experiences a resonance excitation of about 4% magnitude given its position on the sin c lobe.

To ensure that both the alpha and beta anomer hydrogen protons are located at frequency null points, in some embodiments, the RF stimulus pulse ($B_1$) may be a continuous wave RF signal at the water resonance frequency $f_{H2O}$ gated with a triangular pulse of duration ($2\tau$). This RF stimulus pulse has a frequency domain excitation profile expressed by Equation (14):

$$|\sin c^2(\pi \Delta f \tau)| \qquad (14)$$

wherein $\Delta f$ is the offset frequency from the water resonance center frequency, and the pulse duration $\tau$ is defined according to Equation (13).

Still referring to FIG. 3D, the triangular excitation generated by Equation (14) is illustrated by the dotted line. As shown, both the alpha and beta anomer hydrogen proton resonance peaks are now located at frequency null points. Accordingly, the triangular pulse response ensures that metabolite magnetizations are not perturbed, even with small errors in the null frequency positioning.

The amplitude of the long frequency selective pulse ($B_1$), which excites rotation of the water signal onto the transverse plane, is expressed according to Equation (15):

$$B_1 = \frac{\pi}{2\gamma \tau} \qquad (15)$$

where $\tau$ is the pulse duration, and $\gamma$ is the gyromagnetic ratio of the target nuclei. For a pulse duration ($\tau$) of 163 ms (e.g., as determined according to Equation (13)), at the gyromagnetic ratio of hydrogen, the required RF stimulus field ($B_1$) is approximately 40 nanovolts. A single pulse having an amplitude of 40 nanovolts may be, however, too small to achieve practically.

Accordingly, in various embodiments, the RF stimulus signal ($B_1$) may be segmented into a series of high-powered short pulses which approximate the magnitude expressed in Equation (15). For example, the stimulus signal may be implemented using a Delays Alternating with Nutation for Tailored Excitation (DANTE) technique.

The DANTE technique segments the single rectangular pulse, which effects a 90° shift into the transverse plane, into a series of n short pulses of duration ($t_p$), where consecutive pulses are separated by a time duration ($\Delta t$). Each pulse, in the train of n pulses, effects a 90°/n rotation of the water signal. The amplitudes of the n short pulses increase by a factor of $\Delta t/t_p$ relative to the original single pulse, provided $\Delta t \gg t_p$. The duration ($\tau$) of the DANTE pulse sequence may be expressed according to Equation (16):

$$\tau = n t_p + (n-1) \Delta t \qquad (16)$$

The DANTE sequence results in a series of frequency pulses which are separated by $(t_p + \Delta t)^{-1}$ Hertz. Accordingly, $\Delta t$ is adjusted to ensure that the excitation frequency of a DANTE pulse does not eventually overlap with the excitation pulse of the alpha or beta anomer. In various embodiments, extending the DANTE technique to a triangular excitation pulse (as described above) requires application of envelope modulation.

Referring now back to FIG. 10, at act 1006, a de-phasing pulse field gradient (PFG) is applied to the water signal. In particular, the PFG attenuates the FID signal generated by the water signal and allows measuring the alpha and beta anomer resonances without interference from the water signal.

Figure 3E:
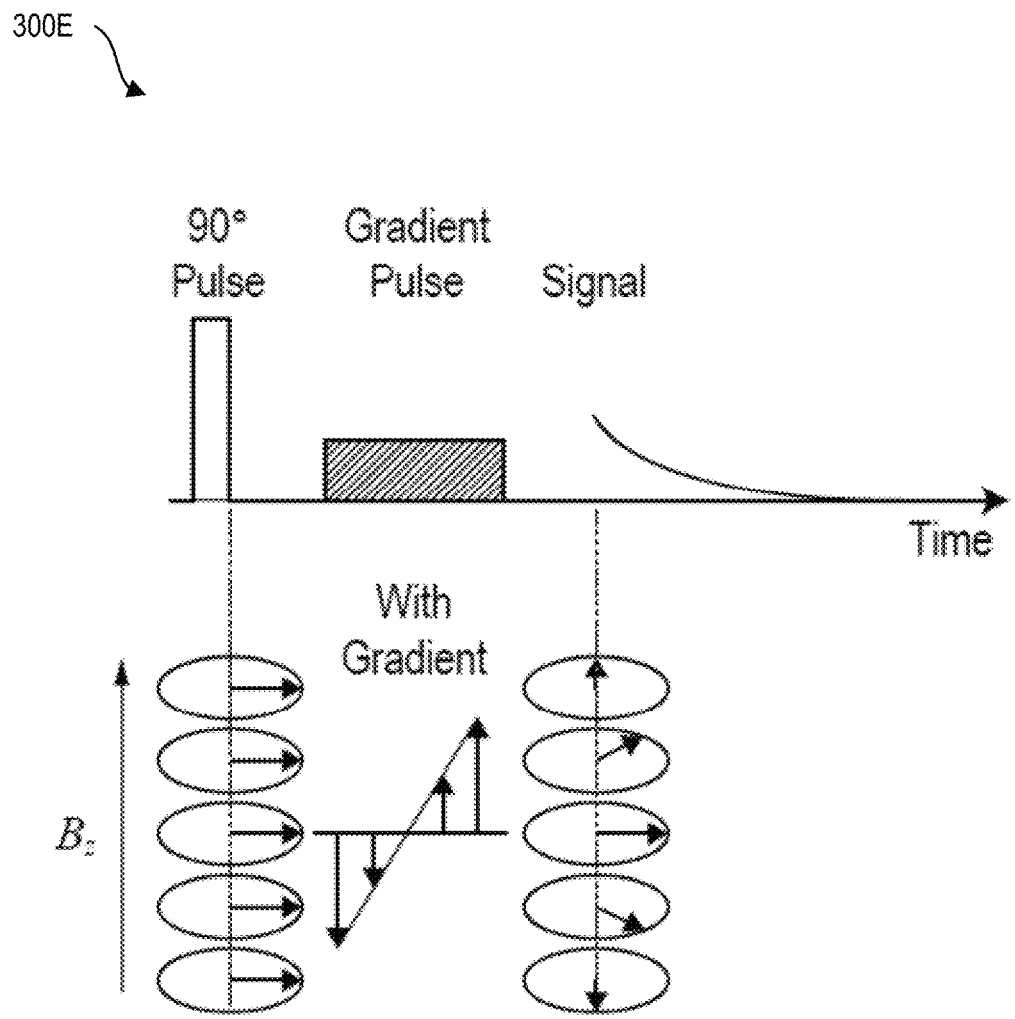
FIG. 3E shows an illustration of the effect of an example pulse field gradient.

Referring now briefly to FIG. 3E, there is shown an example illustration of the effect of a pulse field gradient (PFG) on a water signal. As shown, after a 90° pulse is applied to the water signal, the net magnetic moment, of the water signal, is rotated onto the transverse plane. The spins are coherent after the 90° pulse, and consequently, precess around the z-axis at the same rate to generate the net magnetic moment.

A PFG is a gradient magnetic field applied along the axis as the static magnetic field ($B_0$) and has a variable gradient field strength across the XY plane. More specifically, the PFG exposes different spins to different fields depending on their spatial position, and causes the spins to lose coherency (e.g. spins precess around the z-axis at different rates). Accordingly, the averaged sum of the individual spins no longer add up coherently to generate a strong net magnetic moment in the transverse plane. As such, the net magnetic moment of the water signal is "weakened", and the resonance signal generated by the water molecule is "attenuated" or "suppressed". The magnetic moment of the alpha and beta anomer hydrogen protons are now separately excitable without interference from the water resonance signal. In various embodiments, the combination of acts 1004 and 1006 causes attenuation of the water signal to between 12 dB and 20 dB.

As explained previously, relaxation back to the z-axis occurs at the T1 exponential rate (see Equation (5)). The T1 relaxation of water molecules in blood is approximately 1.4 seconds. Accordingly, the PFG should have a pulse duration of significantly less than 1.4 seconds. In at least some embodiments, water suppression may also be effected by using hyperbolic secant pulses, such as an adiabatic RF pulse. However, hyperbolic secant pulses yield magnetization excitation over a limited frequency band, and accordingly, their time domain pulses are infinite and must be truncated, a process that increases transition band width and introduces frequency domain variations in the magnetization. This is in contrast to the use of the above described technique which only constrains the frequency domain magnetization profile at points of interest and results in an RF pulse of finite temporal extent that obviates truncation.

At act 1008, a second RF stimulus pulse ($B_1$) is applied to rotate the alpha and beta anomers 90° on to the transverse plane. In at least some embodiments, the second RF stimulus pulse is applied at a maximum RF amplitude and minimal duration. This allows mitigation of the transverse relaxation decay at the exponential rate T2* that occurs prior to free induction decay (FID) measurements. In at least some embodiments, the RF stimulus pulse is applied for a duration of less than 1.5 ms.

At act 1010, a lower power continuous wave (CW) irradiation is applied to achieve homonuclear de-coupling. Act 1010 may be performed at least partially concomitantly with act 1008.

CW irradiation resolves the doublet spectral lines of the alpha and beta anomers $^1$H proton into single spectral lines. For example, the CW irradiation resolves the two spectral lines of the alpha anomer $^1$H proton, which are centered at the 5.223 ppm chemical shift point, and are spaced 3.8 Hz apart, into a single spectral line at the chemical shift point. As explained previously, homonuclear decoupling allows for one-to-one mapping of spectral lines in a received FID signal. As also previously described with reference to Equations (9) and (10), homonuclear decoupling minimizes the required frequency measurement bandwidth, and in turn, increases the statistical confidence level of measurements acquired by the portable NMR device.

As the alpha and beta anomers in the $^1$CH group are coupled to the alpha and beta anomers of the glucose $^2$CH group, the CW irradiation is applied at the two anomer $^2$CH group hydrogen proton resonant frequencies (δ=3.519 ppm and δ=3.23 ppm) to achieve highly selective decoupling.

In at least some embodiments, the CW irradiation is applied at a power of below 12 mW per gram of tissue.

At act 1012, and in at least some embodiments, a magnetic resonance velocimetry (MRV) technique is applied in order to distinguish between the resonance signals generated by glucose molecules located in blood plasma and which are otherwise subject to arterial or venous flow from glucose molecules which may be located, for example, in human tissue and are otherwise stationary. In particular, MRV may find specific application where blood glucose concentration levels are being measured in a subject's finger which is received inside of the bore 106 of the NMR device 104 (i.e. rather than in a test blood sample). In these cases, MRV ensures that the measured blood glucose concentration level is limited to only the concentration of glucose located in blood circulating in the subject's finger and does not otherwise include glucose concentration levels for glucose located in the subject's tissue.

More specifically, MRV is used to distinguish between stationary proton spins and spins that are part of fluid flow. As arterial blood flow velocity is between 4.9 cm/s and 19 cm/s, and venous blood travel velocity is between 1.5 cm/sec and 7.1 cm/s, MRV may be used to distinguish glucose which is subject to arterial or venous flow versus glucose which is otherwise stationary (i.e., located in tissue).

Figure 3F:
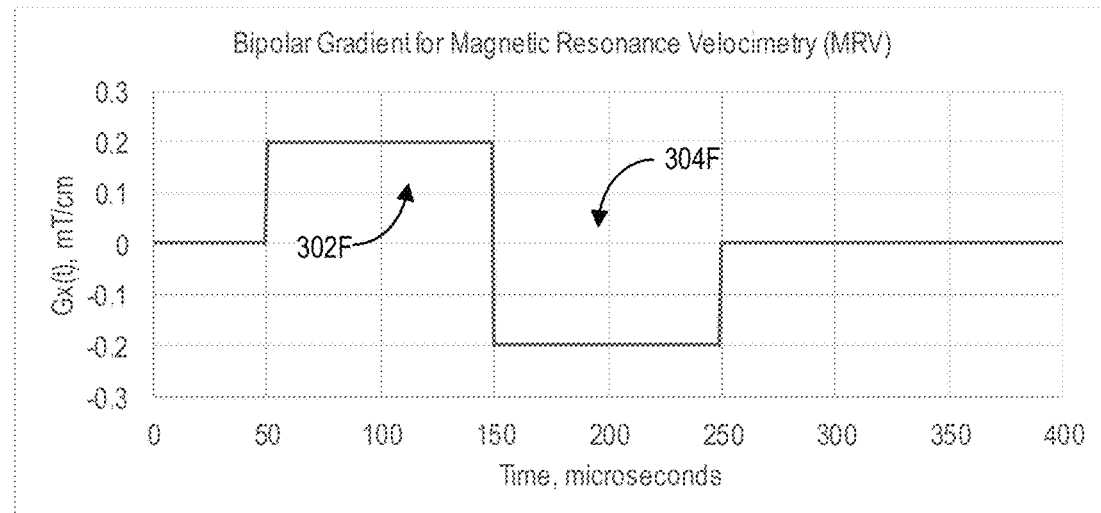
FIG. 3F shows an example bipolar gradient field which is used during magnetic resonance velocimetry (MRV).
Figure 3G:
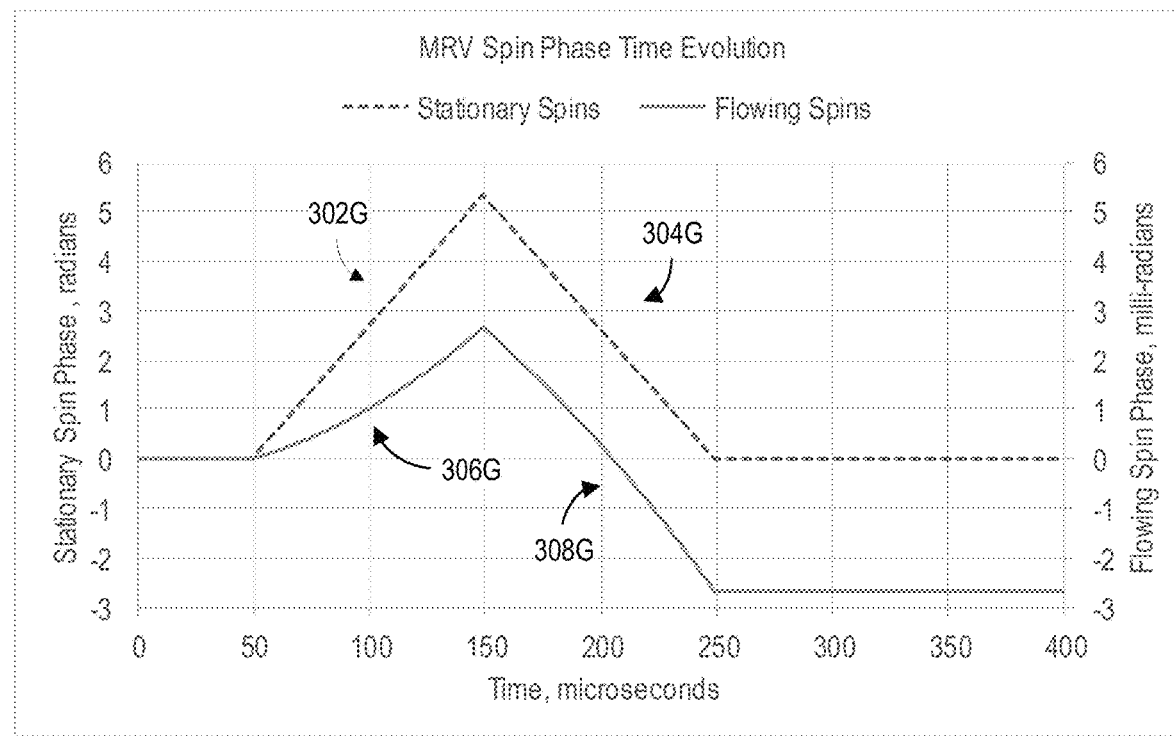
FIG. 3G shows the effect of the bipolar gradient field of FIG. 3F on a proton with a stationary spin and a proton moving at a constant speed.

Referring now briefly to FIGS. 3F and 3G, the principles underlying the MRV will be explained in further detail herein.

Referring now first to FIG. 3F, there is shown an example bipolar gradient pulse (BGP) which may be applied to a subject's finger as part of the MRV technique (also referred to as a flow encoding gradient). The BGP generally functions in a similar manner to the pulse field gradient applied in act 1006. More specifically, the BGP is a gradient magnetic field applied along the axis of the static magnetic field ($B_0$) and which has a variable gradient field along the x-axis. The gradient is varied along the x-axis because circulating blood flow, within a finger placed into the bore 106 of the NMR device 104, will flow primarily along the x-axis (i.e., as defined relative to the NMR device 104).

As shown in FIG. 3F, the BGP comprises a first positive component 302F (i.e., having a positive bipolar gradient) followed by a second negative component 304F (i.e., having an inverse negative bipolar gradient).

Referring now to FIG. 3G, there is shown the effect of the BGP when applied to a stationary proton. In particular, after applying the first positive component 302F of the BGP, the precession rate of the transverse component of the magnetic moment of the proton is perturbed by the gradient field (e.g., the precession speed may be, for example, accelerated as a result of the BGP, causing a phase shift to the transverse component). In particular, the phase-shift induced in a group of proton spins by the BGP at a given time (τ) may be expressed according to Equation (17).

$$\varphi(\tau) = \varphi_0 + \int_0^\tau \omega(t) dt \quad (17)$$

wherein φ(τ) is the phase-shift at time (τ), $\varphi_0$ is the initial phase, and ω(t) is the instantaneous Larmor frequency of the group of proton spins as determined according to Equation (18).

$$\omega(t) = \gamma(B_0 + G_x(t)x(t)) \quad (18)$$

wherein $B_0$ is the strength of the static magnetic field, and $G_x(t)x(t)$ is the strength of the BGP along the z-axis and as a function of the position along the x-axis. In general, phase accumulation due to the constant static field ($B_0$) term may be removed by demodulation at a spectrometer receiving unit of the NMR device 104.

In the example illustrated in FIG. 3G, the BGP causes the transverse component to undergo a phase shift at 302G of approximately 5 radians. Subsequent to applying the first positive component 302F, the second negative component 304F of the BGP is applied. The second negative component has the effect of reversing (or inversing) the perturbation caused to the precession as a result of the first positive component 302F. Accordingly, and as observed in FIG. 3G, during 304G, the phase shift of 5 milli-radians to the transverse component of the magnetic moment is reversed, resulting in a net phase shift of zero. As such, the magnitudes and duration of the positive and negative component of the BGP are designed to advance and retard the stationary spin resonance phases by precisely the same amount in order to return the spins to their original phases.

FIG. 3G also shows the effect of the BGP when applied to a proton moving at a constant speed (e.g., the alpha and beta anomers glucose hydrogen protons which may be flowing through the subject's veins and arteries). FIG. 3G assumes a gradient along the x-axis ($G_x$) of 0.2 mT/cm being applied to a proton travelling at a constant speed of 5 cm/sec.

As shown in FIG. 3G, when the positive component 302F of the BGP is applied, the magnitude of the accumulated phase shift in the transverse component of the magnetic moment becomes quadratic (e.g. 306G). This is because as the proton is moving along the x-axis (i.e., through an artery or vein), the proton is changing its spatial position vis-a-vis the gradient field (i.e., which is variating along the x-axis). Accordingly, the moving proton is continuously being subject to a variable magnetic field over the pulse duration of the positive component of the BGP. When the negative component 304F is subsequently applied, the accumulated phase shift to the magnetic moment, as a result of the positive component, is not reversed (i.e., as is the case where the proton is stationary). This is because the proton is now displaced along the gradient axis and is no longer experiencing the precise inverse gradient that was applied during the positive component 302F. Accordingly, in FIG. 3G, the inverse component generates a reverse or net phase shift of approximately −3 milli-radians (e.g. 308G).

In view of the foregoing, protons which are subject to constant velocity (e.g. protons in circulating blood) are subject to a net phase shift after applying a BGP, whereas protons which are stationary (e.g., located in tissue) experience a zero net phase shift after the BGP. Accordingly, this property is used to distinguish between resonance signals generated by glucose molecules located in blood and resonance signals generated by glucose molecules located, for example, in tissue.

In various embodiments described herein, where MRV is required, method 1000 is applied twice in order to resolve blood glucose from tissue glucose. In particular, a different BGP is applied between the first and second iterations of the method 1000. Typically, an inverted version of the original BGP is applied in the second iteration. The results (e.g., the resonance signals) generated from the two iterations of method 1000 can be subtracted to provide a measurement specific to the flowing spins. Alternatively, the results of the two iterations can be summed to provide a measurement for glucose concentration in the finger tissue At act 1014, the FID signals of the alpha and beta hydrogen anomers are measured based on the T2 relaxation. In particular, and as explained in further detail herein, the FID signal is detected by a set of receiver coils located within the magnet bore 106 of the portable NMR device 104.

At act 1016, the measured FID signal is converted into the frequency domain in order to generate an NMR frequency spectrum (e.g. FIG. 3A). In at least some embodiments, the frequency domain conversion is effected by a Discrete Fourier Transform (DFT). The DFT is facilitated by having resolved the resonance peaks of the alpha and beta anomers into single spectral peaks. In other embodiments, the frequency domain conversion may also be effected by a discrete cosine transform (DCT) or a discrete sine transform (DST), by way of non-limiting examples.

At act 1018, the alpha and beta anomer resonance amplitudes, as determined from the NMR frequency spectrum, are converted into a glucose concentration.

In at least some embodiments, the glucose concentration conversion is implemented by correlating: (a) the resonance peaks of the alpha and beta anomers (e.g. as determined from the NMR frequency plot), to (b) known reference glucose concentration levels. For example, a memory unit located in the portable NMR device 104 may store correlative information between specific resonance amplitudes and known reference glucose concentration levels. Because resonance amplitudes are linearly correlated to glucose concentration levels, interpolation may be used where direct correlative information is absent from the memory unit.

In other embodiments, conversion is implemented in real-time using the ERETIC (Electronic REference To access In vivo Concentrations) method. ERITEC generates an artificial electronic reference resonance peak in the NMR frequency plot which is then used to determine absolute concentration levels.

In still other embodiments, the glucose concentration levels can be determined without direct referencing. For example, the ratio of glucose $^1$CH group alpha and beta resonances may be measured. The nominal anomer split is 36% alpha to 64% beta in human blood. Accordingly, the number of alpha anomer glucose hydrogen protons within a sample of volume $V_s$ may be determined according to Equation (19):

$$N_{\alpha\text{-}glc}=0.36N_A c_{glc} V_s \quad (19)$$

wherein $N_A$ is Avogadro's number, $c_{glc}$ is the mean blood glucose concentration measured in units of moles per liter with a normal physiological value of 5.5×10−3 mol/L (or 99 mg/dL), and $V_s$ is the volume of the sample received in the portable NMR device. For example, assuming, $V_s$ of 2.00E-06 m$^3$, the number of alpha anomer glucose hydrogen protons within a sample is $N_{\alpha\text{-}glc}$, which is calculated to be 2.38E+18 protons.

The anomeric ratio varies based on glucose concentration, temperature, and pH levels of the circulating blood or blood test sample. In various embodiments, temperature and pH may be measured in order to enable determination of glucose concentration from the anomer ratio measured in the free induction decay signal. For example, intracellular pH can be measured in vivo by exciting carnosine molecules in the subject's finger or test blood sample and measuring the generated FID signal (see e.g., R. A. d. Graaf [2]).

In various cases, measuring both the alpha and beta anomers (rather than only one of the anomers) helps to improve repeatability of the measurement and reduces errors due to variation in the anomeric ratio.

In still yet other embodiments, spectral editing may be used to distinguish glucose from macromolecules such as glycated proteins. This capability is important because glycated proteins often have NMR resonances that substantially overlap glucose chemical shifts. Diabetes disease progression is characterized by an increase in glycated proteins over time. In general, metabolites have much higher T1 values than large macromolecules that experience more rapid spin-lattice relaxation, a difference that can be exploited to null the macromolecule signals. A non-selective inversion recovery sequence (180°−td) prior to measuring the metabolites may be used to null the macromolecule response. In various embodiments, the recovery delay is typically set to td=T1_mm*ln(2) so that the macromolecule net magnetization is zero when the metabolites are measured.

Figure 3H:
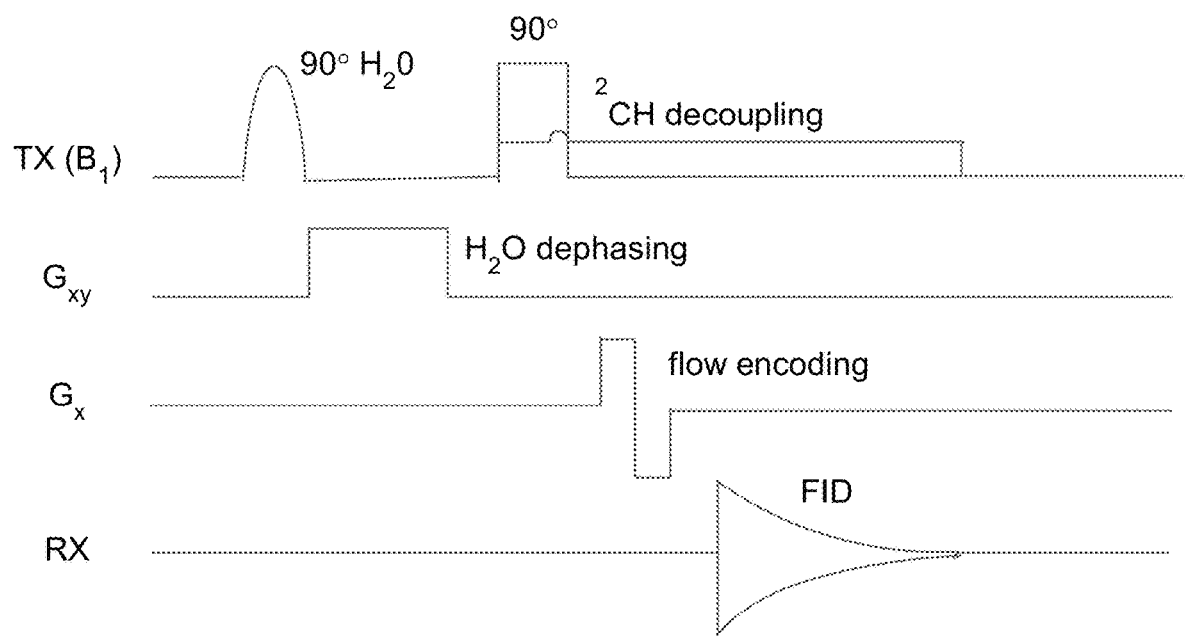
FIG. 3H shows an example embodiment of a sequence of magnetic signals that can be applied for measuring blood glucose concentration based on the alpha and beta glucose anomer $^1$CH hydrogen group proton resonances.

Referring now briefly to FIG. 3H, there is shown pictorially the method for measuring blood glucose concentration based on the alpha and beta glucose anomer $^1$CH hydrogen group proton resonances. As shown, a first 90° pulse is applied to rotate the magnetization of the water hydrogen proton onto the transverse plane. This first pulse is then followed by a de-phasing gradient to attenuate the water signal. A second 90° pulse is subsequently applied to rotate the magnetization of the glucose alpha and beta anomer $^1$CH hydrogen protons onto the transverse plane. At least partially simultaneously with the second 90° pulse, a CW irradiation is applied at the glucose alpha and beta anomer $^2$CH group hydrogen proton resonant frequencies in order effect homo-nuclear decoupling. In at least some cases, a bipolar gradient field (BGF) (or a flow encoding signal) is applied to a subject's finger in order to distinguish glucose hydrogen resonance signals generated by glucose in circulating blood, from resonance signals generated by hydrogen protons located in stationary glucose molecules (e.g. located in tissue). Finally, an FID signal is measured. Where an MRV technique is used, the sequence may be repeated a second time with an inverted BFG in order to properly resolve the glucose hydrogen resonance signals generated by glucose in circulating blood.

Figure 4A:
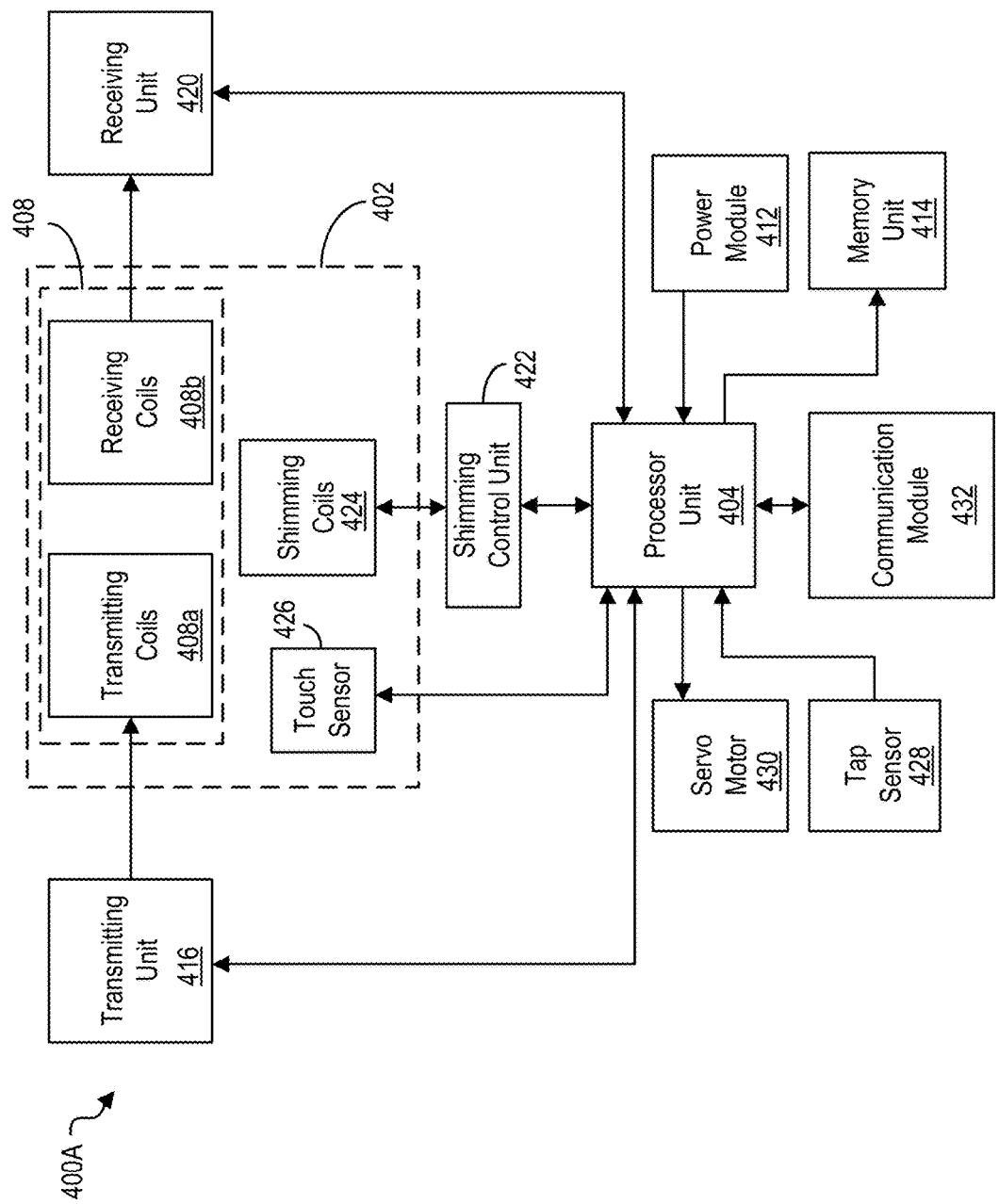
FIG. 4A shows a simplified block diagram for the portable NMR device of FIG. 1A in accordance with at least one embodiment described in accordance with the teachings herein.

Referring now to FIG. 4A, there is shown a simplified block diagram 400A for an example embodiment of the portable NMR device 104 of FIG. 1A, in accordance with another aspect of the teachings herein. As shown, the portable NMR device can be implemented to generally include a processor unit 404 in communication with a communication module 432, a power module 412, a memory unit 414, a transmission unit 416, and a receiving unit 420, as well as a shimming control unit 422. In at least some embodiments, the processor unit 404 may be in further communication with one or more of a touch sensor 426, a tap sensor 428, and a servo motor 430.

In accordance with the teachings provided herein, processor unit 404 may be configured to execute a plurality of instructions to control and operate the various components of the portable NMR device 104. In some embodiments, the instructions may be transmitted from the remote device 112 to the processor unit 404 using communication module 432. In other embodiments, the processor unit 404 may be pre-configured with specific instructions. The pre-configured instructions may be executed in response to specific events or specific sequences of events, or at specific time intervals. Processor unit 404 may also be configured to receive data from the various components of NMR device 104 and to make specific determinations using this data, as described in further detail herein. The determinations may then be stored in the memory unit 414 and/or sent to the communication module 432 for transmission to the remote device 112.

Memory unit 414 may be, for example, a non-volatile read-write memory which stores computer-executable instructions and data, and a volatile memory (e.g., random access memory) that may be used as a working memory by processor unit 404.

The power module 412 may be, for example, a battery capable of supplying power to the portable NMR device 104 for a predetermined period of time. For example, the battery may be a compact battery that is configured to be received within the portable NMR device 104, such as a lithium-ion (Li-Ion) battery. In some other embodiments, power module 412 may be an inductive power module, which can receive wirelessly transmitted power and supply power to the portable NMR device 104. In still other embodiments, the power module 412 may be re-charged using a USB interface located on the portable NMR device 104.

Communication module 432 may be configured to send and receive data, or information, to and from remote device 112. Communication module 432 may, for example, comprise a wireless transmitter or transceiver and antenna. In some embodiments, the communication module 432 may receive instructions or data from the remote device 112 and transmit the instructions or data to the processor unit 404. Accordingly, communication module 432 can be configured to provide duplex communication.

Transmitting unit 416 (also referred to as a spectrometer transmitting unit 416) may be coupled to transmitting coils 408a of a probe device 408. The transmitting coils 408a may be located within the magnet bore cavity 402, which is analogous to the magnet bore 106 of FIG. 1. In various embodiments described in further detail herein, the transmitting unit 416 may be configured to drive the transmitting coils 408a to generate a pulsed RF stimulus field ($B_1$) which induces resonance within an ensemble of target protons located in the subject's finger or sample received in the magnet bore 402. The frequency, or the intensity, of the RF stimulus field ($B_1$) may be determined, for example, by the processor unit 404 in accordance with the techniques described previously.

Receiving unit 420 (also referred to as the spectrometer receiving unit 420) may be similarly coupled to receiving coils 408b of the probe device 408. The receiving coils 408b may also be located within the bore cavity 402. In various embodiments described in further detail herein, the receiving coils 408b may be configured to receive a signal (e.g., an FID signal) generated by a sample located within the bore cavity 402. The receiving coils 408b may then send the signal to the receiving unit 420, which reduces signal noise, and subsequently sends the signal to the processor unit 404 for further analysis. In other embodiments, the processor unit 404 may pass the received signal to the communication module 432, which may then transmit the signal over network 106 to the remote device 112. An application installed on the remote device 112 may be configured to analyze or process the raw signal data, e.g. to determine metabolite levels.

As NMR spectroscopy requires a homogenous static field to be generated across the magnet bore 402, a shimming control unit 422 may be coupled to the processor unit 404. The shimming control unit 422 are in-turn be coupled to a set of shimming coils 424 disposed within the magnet bore 402. As explained in further detail herein, the shimming control unit 422 drives the shimming coils 424 to generate a compensatory magnetic field within the bore cavity 402 to compensate for the spatial non-uniformity of a static magnetic field ($B_0$) generated by permanent magnets located in the portable NMR device 104. The shimming coils 424 may also be used to generate the pulse field gradient (PFG) and the bi-polar pulse gradient (BPG) which are used during water signal suppression and MRV, respectively, as described previously.

In at least some embodiments, the portable NMR device 104 may also include one or more of a touch sensor 426, a tap sensor 428, and a servo motor 430.

The touch sensor 426 (also referred to as proximity sensor 426) may be located inside of the bore 402 and may be used to detect the presence of a subject's finger or a test sample received within the bore 402. In at least some embodiments, the touch or proximity sensor 426 may also be used to detect whether the finger, or test sample, is positioned correctly within the bore 402. If the finger or sample is determined to be correctly positioned, the sensor 426 may transmit a signal to the processor unit 404 instructing the processor unit 404 to activate the various hardware components of the portable device 104 for metabolite testing. In at least some cases, more than one the touch sensor 426 may be included to more accurately determine whether the subject's finger or test sample is accurately positioned within the bore. In various cases, the touch sensor(s) 426 may be capacitive devices which provide an analog value readout. Accordingly, if the touch sensor 426 detects that the subject's finger or test sample is correctly positioned, the touch sensor 426 may generate a higher analog readout as compared to where the subject's finger or touch sensor is incorrectly positioned.

The touch sensor 426 may also incorporate a fingerprint reader which identity tags in vivo measurements. For example, the touch sensor 426 may be located within the magnet bore 402, and may receive a subject's finger located within the bore 402. As data or measurements are collected by the portable NMR device 104, the touch sensor 426 may stamp the data with the information in respect of the subject's finger print. In at least some embodiments, this information may then be stored, for example, in the memory unit 414 for later retrieval. Identity tagging metabolite test results may be useful where multiple subjects use the portable NMR device 104 (i.e., data may be stored and categorized according to each user's respective finger print information). In other embodiments, the portable NMR device 104 may be configured to associate a user's finger print with a corresponding remote device 112. The portable NMR device 104 can accordingly use information from finger print readings to determine which remote device 112 should receive the metabolite test results.

Tap sensor 428 may be incorporated into the portable NMR device 104 to provide for a convenient mechanism to power-up the device. For example, a subject may touch the tap sensor 428, and in turn, the tap sensor 428 may activate the processor unit 404. In at least some embodiments, the tap sensor 428 may be an accelerometer.

In at least some embodiments, the magnet bore 402 may also include a movable or sliding door that is located at the opening of the magnet bore 402. The sliding door opens to provide access to the bore 402 when testing is to be done. Accordingly, activating the tap sensor 432 may result in activating a servo motor 430 which opens the door to the bore cavity 402.

Figure 4B:
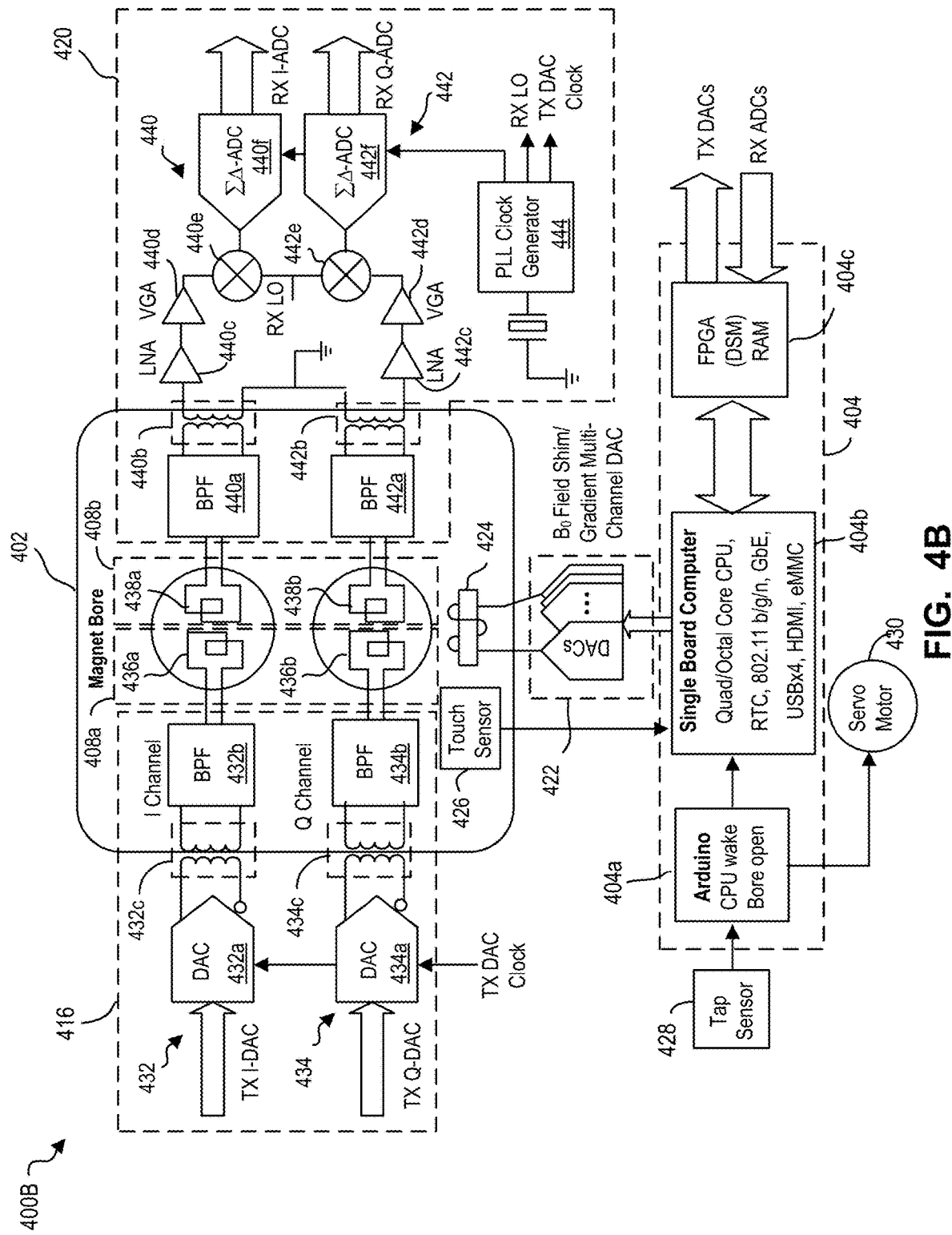
FIG. 4B is a simplified circuit diagram of an example embodiment of the portable NMR device of FIG. 1A.

Referring now to FIG. 4B, there is shown a circuit diagram 400B, which illustrates in more detail the various components of the block diagram 400A.

As shown, the processor unit 404 may include a microcontroller 404a, a single-board computer (SBC) 404b, and a Field Programmable Gate Array (FPGA) 404c. In various embodiments, the microcontroller 404a, SBC 404b and 404c may comprise a single unit.

The microcontroller 404a may receive inputs from the tap sensor 428, and in response to an input signal received from the tap sensor 428, the microcontroller 404a may control or activate the servo motor 430 to open an access door to the magnet bore 402. The microcontroller 404a may also be configured activate the single-board computer (CPU) 404b in response to receiving an activation signal from the tap sensor 428. In at least some embodiments, the microcontroller 404a may be a low power microcontroller, such as an Arduino board.

The single-board computer (SBC) 404b may, once activated by the microcontroller 404a, control the various electrical hardware elements of the portable NMR device 104. For example, the SBC 404b may control the shimming control unit 422 to drive the shimming coils 424 to generate a compensatory magnetic field which compensates for spatial inhomogeneity in the magnetic field provided by the permanent magnets to provide a more homogenous static magnetic field ($B_0$). The SBC 404b may also include the communication module 432 (i.e., which can support IEEE 802.11 communication), as well as various input interfaces, including Universal Serial Bus (USB), High-Definition Multimedia Interface (HDMI), as well as an embedded Multi-Media Controller (eMMC). In various cases, the USB interface may allow the NMR device to be used for either transmitting or receiving data (i.e. as a data feed), or alternatively as a power input to re-charge the power module 412. In at least some embodiments, the SBC 404b can also include an on-board real-time clock (RTC). The RTC can be used to time stamp data measurements generated by the portable NMR device 104.

The FPGA (Digital Signal Processor) RAM 404c may be configured to generate the signals transmitted to the transmitting unit 416, and receive signals generated by the receiving unit 420.

Still referring to FIG. 4B, as mentioned previously, the transmitting unit 416 is configured to drive the transmitting coils 408a to generate a pulsed RF stimulus field ($B_1$). In various embodiments, the transmitting unit 416 is configured to drive the transmitting coils 408a to generate a circularly or elliptically polarized magnetic field ($B_1$) at one or more Larmor, or resonant, angular frequencies of the metabolite to be measured.

To this end, the transmitting unit 416 may include an in-phase transmission pathway 432 and a quadrature transmission pathway 434. The in-phase transmission pathway 432 may be configured to drive a first transmission coil 436a, of the transmitting coils 408a, to generate an in-phase component of the RF stimulus signal ($B_1$). Similarly, the quadrature transmission pathway 434 may be configured to drive a second transmission coil 436b, of the transmitting coils 408a, to generate a quadrature component of the RF stimulus signal ($B_1$). As explained in further detail herein, driving the transmission coils 408a in-phase quadrature allows for generating a circularly or elliptically polarized stimulus signal to induce resonance in target nuclei.

Each of the in-phase and quadrature transmission pathways 432, 434 includes a digital-to-analog converters (DAC) 432a, 434a coupled to passive band pass filters 432b, 434b through broad band transformers or baluns 432c, 434c, respectively. The transformers 432c, 434c may provide for galvanic isolation and impedance matching. The turn ratio for each transformer 432c, 434c may be selected for optimal impedance matching. In various embodiments, the DACs 432a, 434a receive digital signals generated by the processor unit 404 (or the FPGA 404c), and convert the digital signals to analog signals. The DACs 432a, 434a may also receive a sampling clock signal which is synchronized between the two DACs. The analog signals, generated by the DACs 432a, 434a, are then transmitted to the passive band pass filters 432b, 434b across the transformers 432c, 434c. In particular, the band pass filters 432b, 434b receive the signals generated by the DACs 432a, 434a and filter the signals for frequencies within a predefined pass band range of frequencies. In various cases, the pass band range may include one or more Larmor (or resonant) frequencies for one or more ensembles of target nuclei.

Similar to the transmitting unit 416, the receiving unit 420 includes an in-phase receiving pathway 440 coupled to a first in-phase receiving coil 438a, and a second quadrature receiving pathway 442 coupled to a second quadrature receiving coil 438b. As explained in further detail herein, the in-phase receiving coil 438a is configured to receive (or detect) an in-phase component of the FID signal, while the second quadrature receiving coil 438b is configured to receive a quadrature component of the FID signal (e.g., see Equations (6) and (7)). In at least some embodiments, the receiving coils 438 may be the same as the transmitting coils 436. In these cases, fast PIN diode switches may be used to gate the receiver input off while in transmit mode. In at least some cases, two PIN switches are used in series to improve isolation.

Each of the receiving pathways 440, 442 includes a passive band pass filter 440a, 442a coupled, at an input end, to each of the receiving coils 438a, 438b. Each of the band pass filters 440a, 442a may have an analogous topology to the band pass filters 432b, 434b in the transmitting unit 416. In accordance with the teachings herein, the band pass filters 440a, 442a may be configured to filter for a narrow range of frequencies which include one or more Larmor frequencies of the target nuclei.

The filtered signals, generated by the band pass filters 440a, 442a, are then passed through broadband transformers and/or baluns 440b, 442b which are coupled to the output ends of the band pass filters 440a, 442a, respectively. Similar to transformers 432c, 434c of the transmitting unit

416, the transformers 440b, 442b may provide for both galvanic isolation as well as impedance matching. In at least some embodiments, one end of the outbound (or secondary) windings of each of the transformers/baluns 440b, 442b may be center tapped for local ground referencing. The turn ratio for each transformer 440b, 442b may be selected for optimal impedance matching.

Each of the transformers 440b, 442b are coupled, at one node of the outbound winding, to an in-series connection comprising a low noise amplifier (LNA) 440c, 442c, a variable gain amplifier (VGA) 440d, 442d, a local oscillator (LO) 440e, 442e, and an analog-to-digital (ADC) converter 440f, 442f, respectively. The LNAs, VGAs, LOs, and ADCs are used to lower the signal noise and to boost the FID or metabolite signal level to achieve higher measurement accuracy. In various embodiments, the combination of these components allows for a low noise receiver design which achieves a noise level of below 1.1 nV/√Hz as referred to input (RTI).

In at least some embodiments, a clock generator, such as a phase-locked-loop (PPL) clock generator 444 may be coupled to the LOs 440e, 440f, as well as to the ADCs 440f, 442f.

More specifically, the LNAs 440c, 442c are configured to act as a pre-amplifier stage to achieve an overall low receiver noise figure. In at least some embodiments, the LNAs 440c, 442c are configured to generate an overall noise level of below one decibel. The LNAs 440c, 442 may be formed, for example, from GaAs E-pHEMT technology.

The VGAs 440d, 442d are coupled to the output nodes of the LNAs 440c, 442c, respectively, and are configured to boost the amplitude of the received FID signals. In particular, the VGAs 440d, 442d boost the FID signals in order to mitigate for spurious signal products which will be introduced into the FID signals subsequently by the LOs and the ADCs.

In at least some embodiments, the VGAs 440d, 442d can be further incorporated into an Automatic Gain Controller (AGC) circuit which is configured to provide for gain control and to limit the output of the VGAs 440d, 442d. To this end, the AGC may use a feedback loop which accounts for the difference between the output of the VGAs 440d, 442d and an internal reference threshold. The incorporation of the VGA into an AGC ensures that the LO mixer is not overloaded. For example, the LO mixer may be overloaded where insufficient water (or solvent) suppression is performed, and accordingly, the received FID signal not only includes the resonance signal of the glucose protons, but also the resonance signal for the hydrogen protons located in water. In order to minimize receiver noise figure over a wide range of input levels, the AGC sets the maximum VGA gain consistent with not overloading the mixer RF input.

Coupled to the output of the VGAs 440d, 442d are the LO mixers 440e, 442e which are used to filter additional sources of noise from the FID signal, including for example close-in LO phase noise, baseband 1/f noise, as well as intermodulation distortion (IMD). In particular, the LO mixers 440e, 442e ensure that the noise in the received signal is spectrally uniform with a Gaussian-like amplitude distribution, and is not otherwise corrupted with other noise signals. This is in conformity with the assumption used in calculating the statistical confidence in Equation (9). In at least some embodiments, the LOs 440e, 442e are configured to offset the received FID signal at least 100 kHz from the Larmor frequency of the target proton.

ADCs 440f, 442f receive the analog output signals of the LO mixers 440e, 442e, respectively, and convert the signals to digital signals. In at least some embodiments, the ADCs 440f, 442f are high resolution 16-bit sampling ADCs. For example, the ADCs 440f, 442f may be 16-bit sigma-delta ADC converters which are configured to oversample the analog output signals from the LO mixers 4403, 442e at a greater rate than the Nyquist rate (i.e. for quantization). In various cases, to reduce quantization error and increase signal to noise ratio (SNR), a "dithering" noise may be introduced into to the received signal (e.g. a white Gaussian noise). In at least some embodiments, the "dithering" noise may be introduced to ensure 110 dB non-harmonic spurious levels are achieved in the FID signal. In at least some cases, the ADC have ultra-wide band analog inputs. In various embodiments, chemical shifts up to +/−200 ppm in systems under 2T can be accommodated with low frequency or audio sigma-delta converters sampling above 100 kSPS.

Figure 5A:
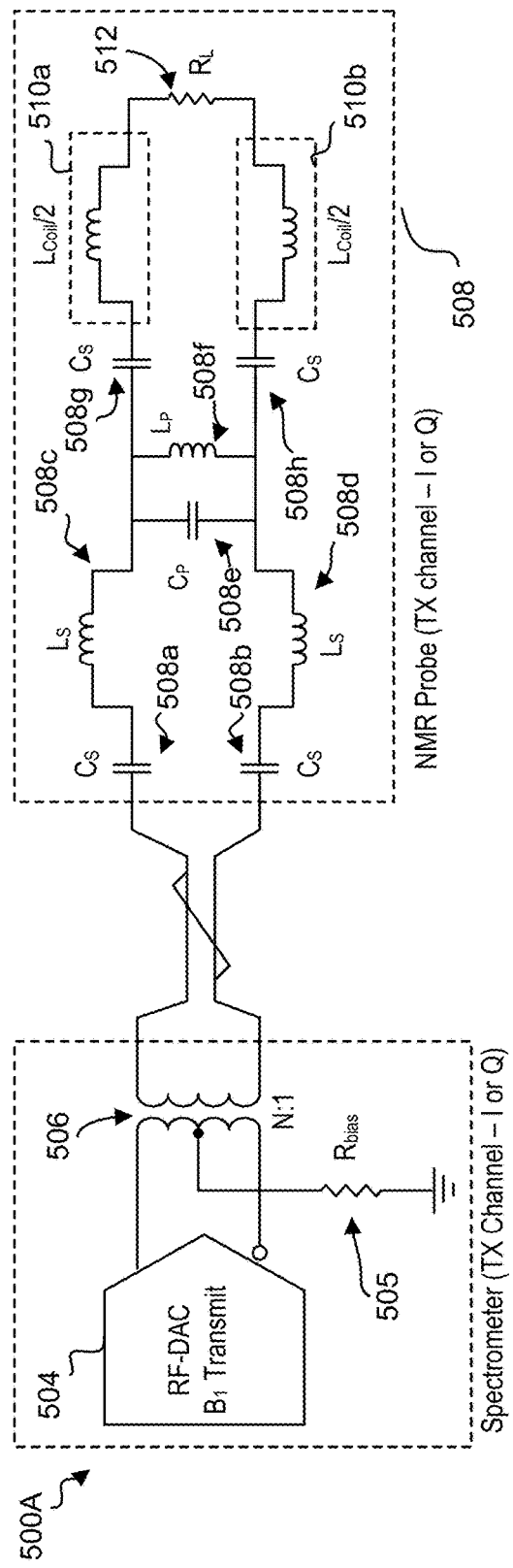
FIG. 5A is a circuit diagram of an example embodiment of a transmission circuit used in the portable NMR device of FIG. 1A.

Referring now to FIG. 5A, there is shown a simplified circuit diagram of an example embodiment of a transmission circuit 500A. The transmission circuit 500A can be used in both the in-phase or quadrature transmission pathways 432, 434 of FIG. 4B. In particular, the transmission circuit 500A illustrates the topology of the band pass filters 432b, 434b in further detail. As illustrated, the transmission circuit 500A includes a digital to analog converter (DAC) 504, a transformer 506 (e.g. characterized by a N:1 turns ratio transformer), a passive band pass filter 508, as well as transmission coils 510a, 510b.

The transformer 506, as mentioned previously, may be a broadband RF transformer which is used for galvanic isolation and impedance matching. The transformer 506 may also be characterized by low insertion loss to minimize noise figure. In some cases, the primary winding of the transformer 506 may include a center tap resistor 505 which is used for DC biasing of the DAC 504 output. In particular, the center-tapped transformer may have an insertion losses of 0.5 dB to 1.0 dB. In at least some embodiments, the RF broadband transformers may be a transmission line style broadband balun transformer which has an insertion loss below 0.2 dB.

The band pass filter 508 may be analogous to either the band pass filters 432b, 434b of the transmitting unit 416 of FIG. 4B. As illustrated, the band pass filter 508 may be a third, or higher order, differential bandpass tee topology filter.

In particular, the band pass filter 508 may include two parallel branches (i.e. a first branch, and a second branch) which each include a capacitor ($C_s$) 508a, 508b in series arrangement with an inductor ($L_s$) 508c, 508d. The input nodes of each of the capacitors ($C_s$) 508a, 508b is coupled to an output node of the output (or secondary) winding of the transformer 506. A parallel arrangement of a capacitor ($C_P$) 508e and an inductor ($L_P$) 508f extends between the first branch and the second branch. Specifically, one common (or shared) node of the capacitor ($C_P$) 508e and inductor ($L_P$) 508f is coupled to an output node of the inductor 508c (Ls), and the other common (or shared) node of the capacitor ($C_P$) 508e and inductor ($L_P$) 508f is coupled to an output node of the inductor ($L_s$) 508d.

On the other side of the parallel arrangement of the capacitor ($C_P$) 508e and the inductor ($L_P$) 508f, is another set of parallel branches which each include a capacitor 508g, 508h ($C_S$). Each capacitor 508g, 508h ($C_P$) has an output node which is coupled in-series to an outbound coil winding 510a, and a return coil winding 510b. In various embodiments, the outbound and return coils windings 510a, 510b correspond to an outbound and return coil winding of one of the first in-phase transmission coil 436a, and the second quadrature transmission coil 436b. Each of the outbound and return windings 510a, 510b may be located within the magnet bore and are similarly polarized (i.e., in-phase or quadrature). By implementing the transmission or receiving coils as one-half length outbound winding, and one-half length return winding, the coil length may be effectively reduced by a factor of two, which results in an increase in the self resonance frequency of the inductor coils, (i.e., the frequency limit at which the inductor coils lose their functionality and behave as open circuits). Increasing the inductor self-resonance frequency ensures that the self resonance frequency is higher than the operating passband frequencies.

A load resistor 512 is connected in-series between the outbound winding 510a and the return winding 510b. Because the filter 508 provides a band pass (voltage) magnitude frequency response across the load resistor 512, and the bandpass filter synthesized from a tee topology low pass filter has its final branch inductor(s) 510a, 510b in series with the load resistor 512, the inductor current (i.e., the NMR coil current) also has the same magnitude frequency response characteristic. Further, the outbound and return coil current is directly correlated with the strength of the RF stimulus field ($B_1$) in each coil.

In various embodiments, the maximum voltage ratings of the capacitors must be enough to handle the working voltage drops in resonance. Further, the filter lumped inductances Lp and Ls may be situated outside the main bore 106 field to avoid saturation of their ferrite cores by the static field ($B_0$).

The above described bandpass filter topology avoids a number of problems associated with conventional transmitting units. In particular, conventional transmitting units in NMR applications employ narrow band high Q tuned LC circuits which use tunable capacitors. The capacitors must be tuned to a given operating frequency (i.e. the Larmor or resonant frequency) in order to achieve impedance matching between the transmission coils, i.e. the load to the LC circuit, and the transmission line. Accordingly, the LC circuit is impedance matched for one operating frequency. Tunable capacitors, in traditional LC circuits, are also unreliable, require time consuming costly manual adjustment, and introduce noise and gain error.

Conversely, the bandpass filter design, in accordance with the teachings herein, includes no tunable circuit elements, and can operate to filter a pass band of frequencies which includes one or more Larmor frequencies rather than only one Larmor frequency. This feature may, for example, supports heteronuclear NMR experiments. For example, in one application, the transmitting pass band range can include closely proximate Larmor frequencies for hydrogen $^1$H and Fluorine $^{19}$F. The Larmor frequency of $^{19}$F is 0.94× that of $^1$H protons, a difference that is currently supported only by "doubly tuned" resonant LC circuits. In particular, NMR studies of fluorine can be used to study the metabolism of Fluorine containing drugs and anesthetics. Further, the above described bandpass tee topology provides for broader passband with flat frequency response that allows all spectral components to experience the same gain. This feature allows the portable NMR device 104 to operate over a wider range of Larmor frequencies without requiring analog probe retuning.

Allowing the transmission of frequencies within a pass band range (rather than at one operating frequency) also accommodates for manufacturing tolerances in the permanent magnet design. Permanent magnets often have a range of residual magnetization that varies by up to +/−3% around a nominal value. As the Larmor frequency is a function of the static magnetic field (see e.g., Equation (2)), variations in the residual magnetization from the nominal value can result in variations in the Larmor frequencies. Conventional LC circuits, which operate at a single frequency, require constant re-turning to accommodate for manufacturing tolerances.

Figure 5B:
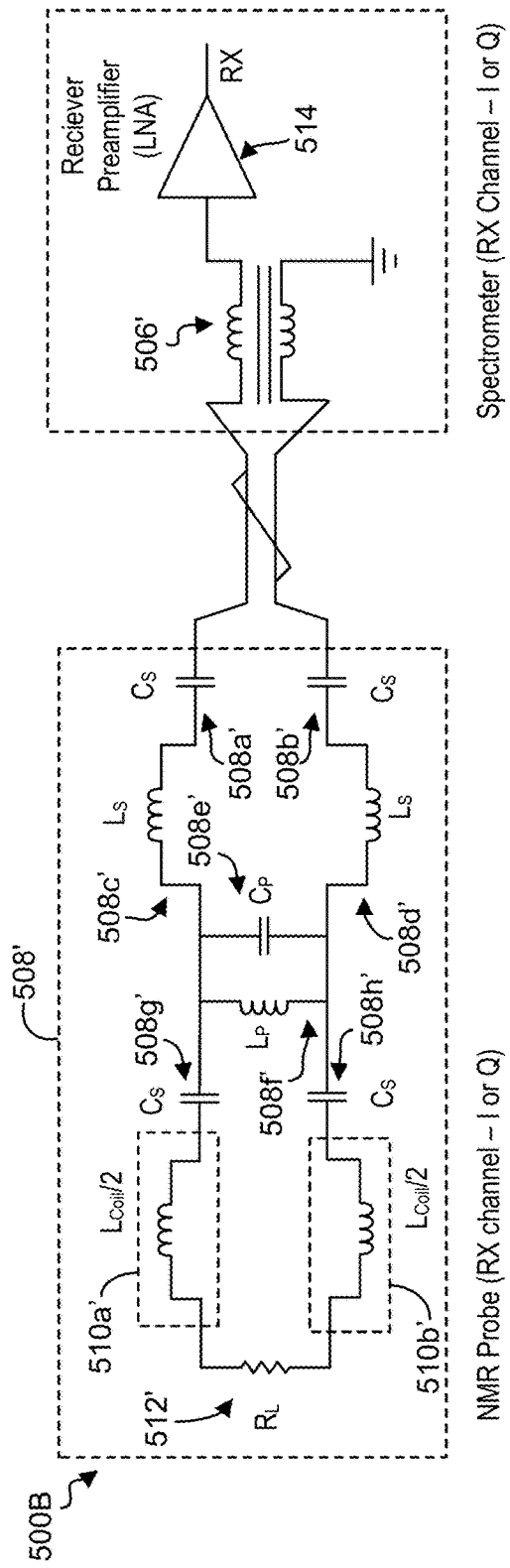
FIG. 5B is a circuit diagram of an example embodiment of a receiver circuit used in the portable NMR device of FIG. 1A

Referring now to FIG. 5B, there is shown a simplified circuit diagram of an example embodiment of a receiver circuit 500B. The receiver circuit 500B can be used in both the in-phase or quadrature receiving pathways 440, 442 of FIG. 4B. As illustrated, the receiving circuit 500B includes a passive band pass filter 508' as well as a transformer 506'. In particular, the band pass filter 508' may be analogous to either the band pass filters 440a, 442a of the receiving unit 420 of FIG. 4B.

The band pass filter 508' has an identical design to the band pass filter 508 of FIG. 5A. To this end, the band pass filter 508' includes outbound and return coils windings 510a', 510b' corresponding to an outbound and return coil winding of one of the first in-phase receiving coil 438a, and the second quadrature receiving coil 438b. Each of the outbound and return windings 510a', 510b' may be located within the magnet bore and are similarly polarized (i.e., in-phase or quadrature). A load resistor 512' is connected in-series between the outbound winding 510a' and the return winding 510b'.

In at least some embodiments, the transformer 506' may be center tapped for ground referencing at the output (secondary winding). The transformer 506' may also be coupled to a low noise amplifier (LNA) 514, which may be analogous to LNAs 440c, 442c of FIG. 4B.

In various cases, the pass band range of the band pass filter 508' may be different than the pass band range for the band pass filter 508. This may allow generating a pass band range at the transmitter side which includes the Larmor frequencies for one or more isotopes, while generating a pass band range at the receiver side which detects the Larmor resonance signal of only one particular isotope.

Figure 5C:
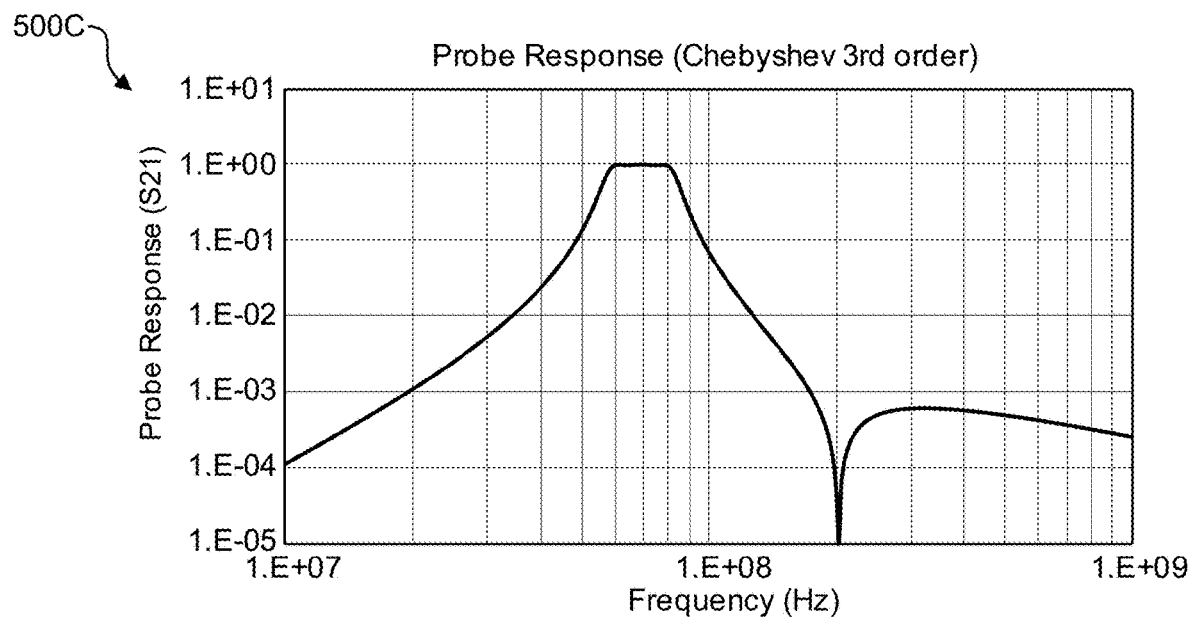
FIG. 5C shows an example frequency response for a band pass filter used in the transmission circuit of FIG. 5A or the receiver circuit of FIG. 5B.

Referring now to FIG. 5C, there is shown an example frequency response plot 500C for the band pass filter 508 of FIG. 5A or the band pass filter 508' of FIG. 5B. Specifically, the plot 500C illustrates a simulated frequency response for a $3^{rd}$ order Chebyshev response bandpass filter, which is designed to support Larmor frequencies between 60 MHz to 80 MHz. Coil self resonance manifests as a stopband zero at approximately 200 MHz.

Figure 6:
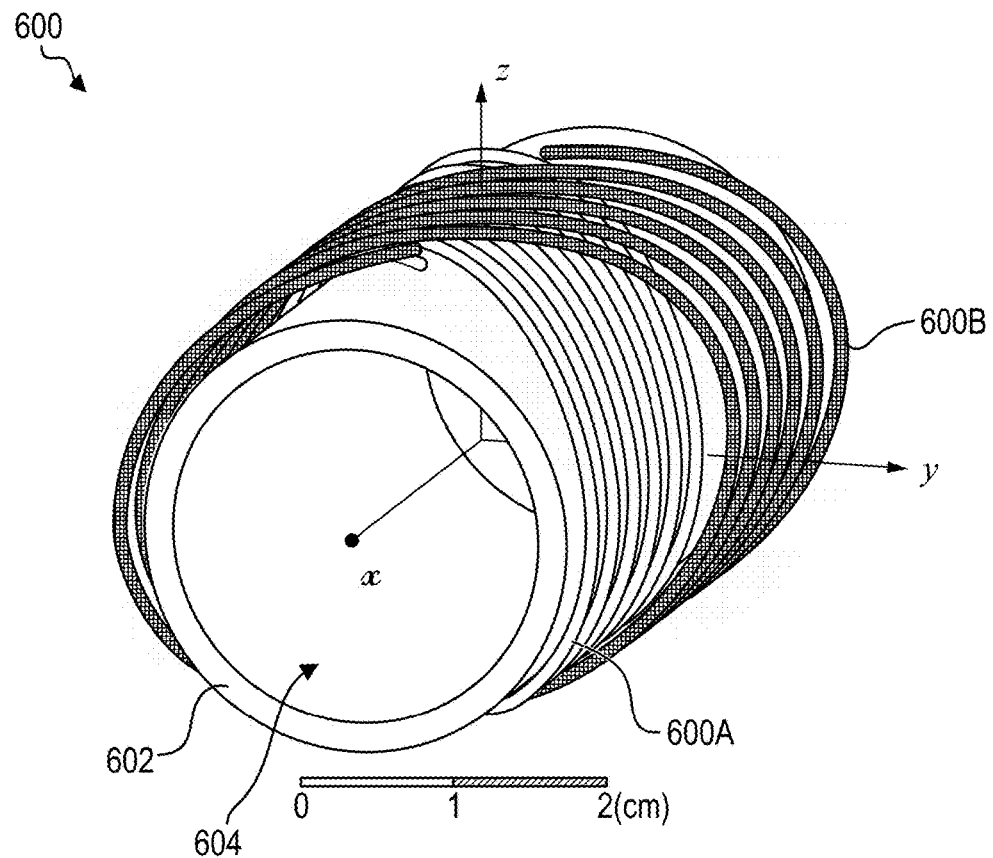
FIG. 6 shows a schematic representation of an example set of coils located in the portable NMR device of FIG. 1A in accordance with at least one embodiment in accordance with the teachings herein.

Referring now to FIG. 6, there is shown a schematic representation of an example set of coils 600 in accordance with some embodiments. One instance of the coil set 600 may be used to implement the RF transmitting coils 408a, and a second instance of the coil set 600 can be used to implement the RF receiving coils 408b.

The coil set 600 may include a first in-phase coil 600A and a second quadrature coil 600B. In various embodiments, the coils 600A and 600B may be volume coils, such as solenoids or air inductors, which provide a more uniform RF stimulus magnetic field ($B_1$) across the magnet bore 106 at the transmitting end, and provide better receiving sensitivity at the receiving end, as compared to surface coils currently used in high field NMR applications. More specifically, in contrast to surface coils, volume coils are inherently able to generate more uniform stimulus fields that do not otherwise rely on the use of adiabatic pulses. Adiabatic pulses, which provide homogenous stimulus fields over certain thresholds, are commonly used with surface coils to compensate (or mitigate) for the inherent inhomogeneous RF stimulus field which these surface coils typically generate. As previously mentioned however, because adiabatic pulses must be truncated in the time domain, surface coils may not otherwise be used to generate high frequency selective excitation pulses with high uniformity (e.g. as required in a water suppression technique). Accordingly, the ability of volume coils to generate inherently homogenous stimulus fields, which do not rely on adiabatic pulses, enables the volume coils to be used in applications where high frequency selective excitation pulses are necessary. The low field design of the portable NMR device (e.g. generating fields below 2 T), as well, is adapted for the lower self-resonance frequencies of volume coils.

Referring still to FIG. 6, the geometry of the coils 600A and 600B may be a helical coil geometry which is characterized according to Equation (20):

$$C(x,y,z) = C(R \sin \theta \cot \alpha + p\theta/2\pi, R \sin \theta, R \cos \theta) \quad (20)$$

where "R" is the radius of curvature of each coil, "$\theta$" is the angular parameter, "$\alpha$" is the tilt angle, and "p" is the pitch.

In FIG. 6, the coils 600A, 600B are shown as extending lengthwise in an x-direction and tilted with respect to a YZ plane. When the coils 600 are placed within a magnet bore, the z-axis of the coils 600 defines the axis of the static magnetic field ($B_0$).

In at least some embodiments, the coils 600A, 600B may be spatially orthogonal canted cosine coils which are tilted, or canted, in opposite directions and at an angle of ±45 degrees relative to the YZ plane to generate circularly polarized RF signals. In other cases, the spatial offset angle can be adjusted in order to generate, for example, elliptically polarized RF signals.

When the coils 600A are being used as transmitting coils (e.g. 408A in FIG. 4A), the first in-phase coil is coupled to the in-phase transmission pathway 432 and is driven to generate an in-phase component of the stimulus field ($B_1$), while the second quadrature coil 600B is coupled to the quadrature transmission pathway 434 and is driven to generate a quadrature component of the stimulus field ($B_1$). In driving the coils 600A, 600B in phase quadrature, the coils 600 may generate a circular polarized field (e.g. left hand or right hand, as required and defined by the gyromagnetic ratio of the target isotope) which induces magnetic resonance in that target isotope. The frequency of the transmitted stimulus field ($B_1$) may be controlled by the bandpass filters of the transmission unit 416 as explained previously.

When the coils 600 are being used as receiving coils (e.g. 408B in FIG. 4A), the spatially orthogonal arrangement of the coils allows the coils to detect a circularly polarized FID signal generated in the transverse XY plane. In particular, the first in-phase coil 600A may detect an in-phase component of the FID signal, while the second quadrature coil 600B may detect a quadrature component of the FID signal (e.g., see Equations (4) and (5)). The sum and difference signals of the two canted cosine coils at the receiving end can accordingly be used to discriminate magnetization signals that are projected onto the two transverse spatial axes (i.e. the X and Y axis), which may be required for some NMR spectroscopy applications.

Still referring to FIG. 6, in order to support the coils 600A, 600B in a stable position, the coils 600A, 600B may overlay a hollow cylindrical support structure 602. The support structure 602 may include a cavity 604 which receives a subject's finger or a test sample when the structure is placed in the magnet bore 106. In at least some embodiments, an outer surface of the cylindrical support structure 602 may be lined with helical grooves, or indents, which receive the helical coils. The helical grooves or indents may help to maintain the helical form of the coils, as well as the position of the coils vis-à-vis each other. In particular, the mechanical support 602 and the indents or grooves on the outer surface thereof, are important to maintain the structural integrity of the coil geometry against counteracting Lorentz forces which may otherwise deform the coil geometry over time. In at least some embodiments, the coils may include an insulating protection cover.

The cable connections between the coils and the corresponding spectrometer components (e.g. the transmission unit 416 and the receiving unit 420) may run in parallel to the axis of the static magnetic field ($B_0$) (e.g. the z-axis), and be situated within the magnet assembly frame of the portable NMR device 104, in order to avoid generating any z directed error component to the $B_0$ field.

In various embodiments, the connection between the coils 600A, 600B and the spectrometer receiving and transmitting units 416, 420 is accomplished with shielded twisted pair cabling. The shielded twisted pair cabling is effective to prevent coupled noise and to provide emission suppression, which are important considerations given how close the portable NMR device 104 operates to FM radio bands. In at least some embodiments, the shielded twisted pair cabling may be a Category 6A ethernet cable which contains four differential pairs of wide analog bandwidth (>500 MHz) shielded twisted pairs, and accordingly, supports in-phase and quadrature signal delivery for both transmit and receive modes of operation.

Figures 7A, 7B:
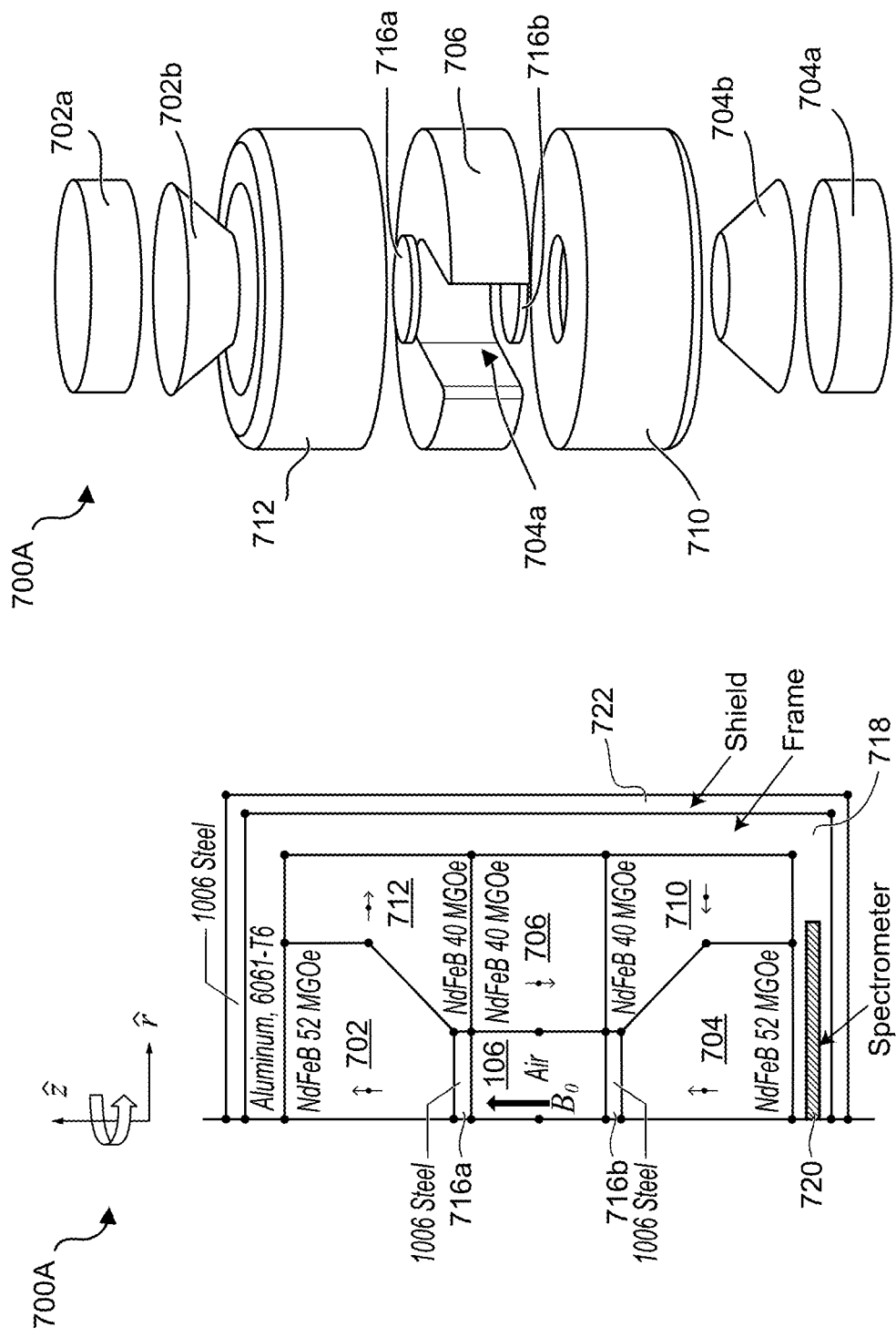
FIG. 7A shows a cross-sectional view of the portable NMR device along the section line 7-7' of FIG. 1A and illustrating a permanent magnet assembly located within the portable NMR device according to at least one embodiment in accordance with the teachings herein.
FIG. 7B shows an exploded view of the permanent magnet assembly of FIG. 7A.

Referring now to FIGS. 7A and 7B, there is shown an example embodiment of an axisymmetric permanent magnet assembly 700A that can be used by the portable NMR device 104 of FIG. 1A according to some embodiments. In particular, FIG. 7A shows a cross-sectional view of the portable NMR device 104 along the section-line 7-7' of FIG. 1A. FIG. 7B shows an exploded view of FIG. 7A.

The axisymmetric permanent magnet assembly 700A shown in FIGS. 7A and 7B is compact and is capable of generating strong and near homogenous static magnetic fields ($B_0$) across the magnet bore 106 with improved field confinement properties. The compact size of the permanent magnet assembly 700A allows for the realization of a portable and consumer-friendly NMR device.

As illustrated therein, the axisymmetric design includes a number of magnet segments rotated about an axis of symmetry (e.g. the z-axis). Each of the magnets is characterized by a magnetization direction that is either oriented along the axis of symmetry (z), or along the radial axis (r). A static field ($B_0$) is generated in the +z direction as a result of the superimposition of the magnetic fields generated by each permanent magnet segment.

In accordance with the teachings provided herein, a stronger, more uniform, and better confined $B_0$ field results because the Hilbert transform relationship between orthogonal r and z magnetization components in each segment is achieved over the entire range from 0 to $2\pi$. In contrast the Hilbert relationship between r and $\phi$ components in a traditional Halbach cylinder design, conventionally used in NMR applications, is only maintained for its finite length along the z-direction.

In further detail, the axisymmetric permanent magnet includes a top disk magnet segment 702a and a top cone magnet segment 702b which are stacked above the magnet bore 106 in the +z direction. Each of the top disk and top cone magnet segments 702a, 702b has a magnetization in the +z direction. In at least some embodiments, these segments can comprise a single magnet segment. A steel disk 716a may be interposed between an upper portion of the magnet bore 106 and the bottom surface of the top magnet disk 702b in order to strengthen the magnetic static field ($B_0$), as well as to improve the static field uniformity. In particular, and by default, a magnetic field exiting a region of high permeability (e.g., steel) and entering a region of low permeability (e.g., air in the magnet bore 106) will exit normal to the surface. Accordingly, this feature allows for improvement to the static field ($B_0$) uniformity. In various embodiments, the surface of the steel disk 716a can be more precisely shaped to compensate for non-uniformity in the static magnetic field ($B_0$) field.

Similarly, a bottom disk magnet segment 704a and a bottom cone magnet segment 704b are stacked below the magnet bore 106 in the −z direction. Each of the bottom disk and bottom cone magnet segments 704a, 704b has a magnetization in the +z direction. Similar to segments 702a and 702b, in at least some embodiments, these two segments 704a, 704b can also comprise a single magnet segment. A steel disk 716b may also be positioned between a bottom portion of the magnet bore 106 and an upper surface the bottom disk magnet segment 704b to strengthen the magnetic static field ($B_0$), as well as to improve the static field uniformity.

A central ring magnet segment 706 is located radially outwardly from the magnet bore 106, in the +r direction, and is characterized by a magnetization in the z direction. The central ring magnet segment 706 at least partially surrounds the magnet bore 106 while leaving unobstructed an access opening to the bore 106 (e.g., to receive a subject's finger or a test sample).

Stacked above the central ring segment 706 in the +z direction, and radially outwardly in the +r direction from the top disk and cone segments 702a, 702b, is top ring magnet segment 712 which has a magnetization in the +r direction.

Similarly, stacked below the central ring segment 706 in the z direction, and radially outwardly from the bottom disk and cone segments 704a, 704b is a bottom ring magnet segment 710 having a magnetization in the r direction.

In various embodiments, the top, central, and bottom permanent magnetic rings may be implemented with multiple transversely magnetized cylindrical magnets with their magnetizations oriented along +r or −r directions (e.g. 12 magnets spaced 30 degrees apart).

As stated above, the net magnetization generated by each of these permanent magnet segments results in a static magnetic field ($B_0$) in the vertical +z direction inside the magnet bore 106. To this end, each of the magnet segments may be formed of a "hard" permanent magnetic alloy, such as a neodymium (NdFeB) permanent magnet, which permits the principle of superposition to apply. In at least some embodiments, N40 grade NdFeB permanent magnet material is used in the central ring 706 where there is a high reverse coercive field. In particular, the high reverse coercive field results from the strong static magnetic field ($B_0$) in the magnet bore 104 which is tangent to, and opposing in direction, to the magnetization of the central ring 706. As well, the top and bottom rings 710, 712 may be formed from N40 grade NdFeB permanent magnet to provide optimal field confinement. N52 grade NdFeB permanent magnet material may be used in the top and bottom cone and disk segments 702 and 704. In various embodiments, modifying the grade of each magnet provides a degree of freedom when trying to minimize the flux that escapes from the ideally one-sided flux structure, and as a result, allowing for the minimizing of the size and weight of a protective shield around the permanent magnet assembly.

Table 1, below, provides a summary of the magnetization directions and material types for each magnet segment in the segmented axisymmetric magnet assembly 700A.

TABLE 1

Axisymmetric Magnet Array Design

| Component | Material | Magnetization |
|---|---|---|
| Top Cone (702a) | NdFeB | $\hat{z}$ |
| Top Disk (702b) | NdFeB | $\hat{z}$ |
| Top Ring (712) | NdFeB | $\hat{r}$ |
| Central Ring (706) | NdFeB | $-\hat{z}$ |
| Bottom Ring (710) | NdFeB | $-\hat{r}$ |
| Bottom Disk (704b) | NdFeB | $\hat{z}$ |
| Bottom Cone (704b) | NdFeB | $\hat{z}$ |

In accordance with the teachings provided herein, the segmented axisymmetric permanent magnet architecture described above ideally provides for a near-uniform and a strong static magnetic field ($B_0$) of 1.79 T across the magnet bore 106. In particular, this assumes a permanent magnet structure having a height and diameter, each of approximately 10 cm (and a weight of approximately 10 kg). However, because the magnet bore 106 carves into the central ring 706, the angular (or azimuthal) symmetry of the permanent magnet assembly is compromised and results in a reduction of the magnetic field strength by approximately 4% to 6% down to about 1.68 T for example. Nevertheless, a magnetic strength of 1.68 T represents an improvement over traditional segmented Halbach cylinder permanent magnet architectures (which are often used in NMR) and which normally achieve a static field strength of 1.54 T in the magnet isocenter. As mentioned previously, improving the strength of static magnetic field in the magnet bore is an important consideration in improving the SNR of the received resonance signal in the portable NMR device 104 (e.g., SNR improves approximately in proportion to $B_0^2$).

The segmented magnet architecture of FIGS. 7A and 7B also achieves confinement of the 5 Gauss field line. The 5 Gauss field line defines the outer perimeter line of the magnetic field where the magnitude of the static magnetic field $B_0$ is greater than 5 Gauss. Confinement of the 5 Gauss field line is an important safety consideration for magnetic equipment which is in routine commercial use.

Still referring to FIGS. 7A and 7B, a hollow frame 718 may be disposed about the permanent magnet assembly to provide an outer 3D perimeter and an air gap about the axisymmetric permanent magnet. The hollow frame 718 may receive various electric hardware which is used for the operation of the NMR device 104. In various embodiments, the hollow frame 718 may be configured to receive the electronic circuitry illustrated in FIGS. 4A and 4B (e.g., a spectrometer 720 for analyzing the FID signals generated from the subject's finger or test sample located in the magnet bore 106). In various embodiments, where the coils 408a, 408b are located in the magnet bore 106, the cable connection between the coils 408a, 408b and the spectrometer 720 may extend from the coils, through the magnet bore 106, down through the frame 718, and under the permanent magnet assembly to the spectrometer 720 or, if the spectrometer 720 is provisioned externally, out the back of the permanent magnet assembly.

The hollow frame 718 may be formed a non-magnetic material which protects electrical hardware and circuitry from leakage magnetic field generated by the permanent magnet assembly. In at least some embodiments, the frame 718 may be formed from aluminum, which is both non-magnetic and lightweight.

To provide further insulation against static magnetic field leakage, the NMR device 104 may also include an outer shield layer 722 that is disposed about the hollow frame 718. The shield layer 722 may be formed of any suitable material which is characterized by high saturation field strength, as well as high permeability. In at least some embodiments, the material forming the shield layer 722 may be characterized by a saturation field strength property of greater than 1.5 T, and a permeability of greater than 100 $\mu_o$. In at least some cases, the outer shield layer 722 may be formed of a Martensitic or Ferritic stainless steel which has high corrosion resistance and good magnetic properties (e.g. high permeability and high saturation strength). In various embodiments, the outer shield layer 722 may be 3 mm thick. An additional outer shield layer may also incorporated over the shield layer 722 in some cases to provided additional leakage protection. This additional shield layer 722 may be formed, for example, from a thin Mu metal.

Figures 7C, 7D:
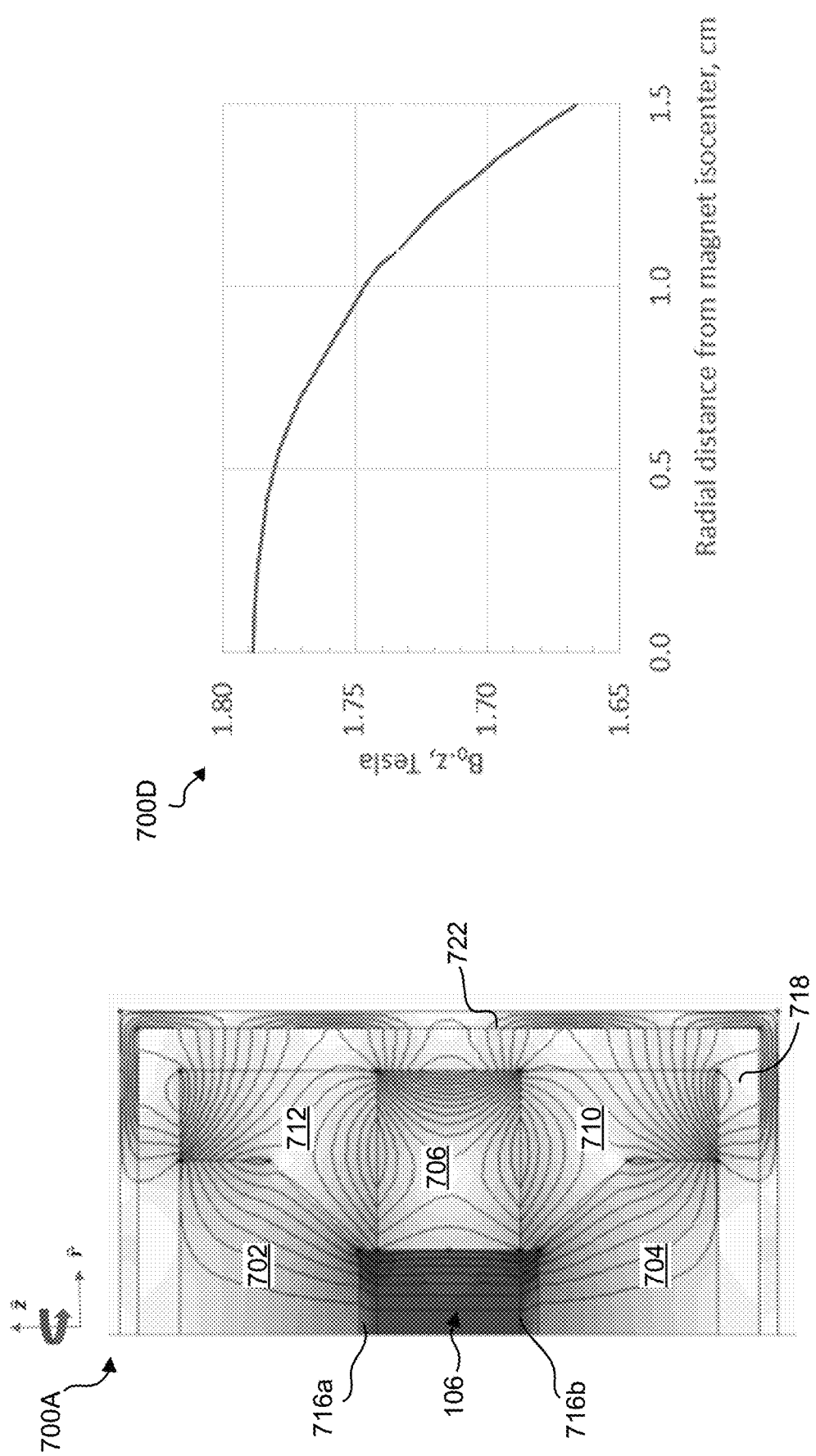
FIG. 7C shows a contour field plot generated by simulating the magnetic field components generated by the permanent magnet assembly of FIGS. 7A and 7B.
FIG. 7D shows a plot of the strength of the static magnetic field ($B_0$) generated by the permanent magnet assembly of FIGS. 7A and 7B as a function of radial distance from the magnet isocenter.

Referring now to both FIGS. 7C and 7D, there is shown a simulation of the static magnetic field ($B_0$) generated by the segmented axisymmetric permanent magnet assembly in FIGS. 7A and 7B. In particular, FIG. 7C shows the contour field plot generated by the permanent magnet assembly of FIGS. 7A and 7B. FIG. 7D shows a plot 700D of the strength of the static field generated within the magnet bore 106 as a function of radial distance from the magnet isocenter.

As shown in FIG. 7C, the superimposition of the magnetic fields generated by each of the magnet segments 702 to 712 is a magnetic field in the bore 106 along the axis of symmetry (+z) direction. Further the axisymmetric arrangement of the permanent magnets achieve, in conjunction with the outer layer shield 722, minimal magnetic field leakage out of the device 104 and confines the static field there within.

FIG. 7D shows a plot 700D of the magnetic field strength as a function of radial distance (i.e., along the transverse plane XY) from the magnet isocenter, or the center of the magnet bore 106. As shown, the axisymmetric design achieves a 1.79 Tesla static magnetic field strength at the isocenter and tapers off to only about 1.67 Tesla at 1.5 cm from the isocenter due to the compromise in azmithual symmetry as a result of the magnet bore, as previously explained.

Figure 7E:
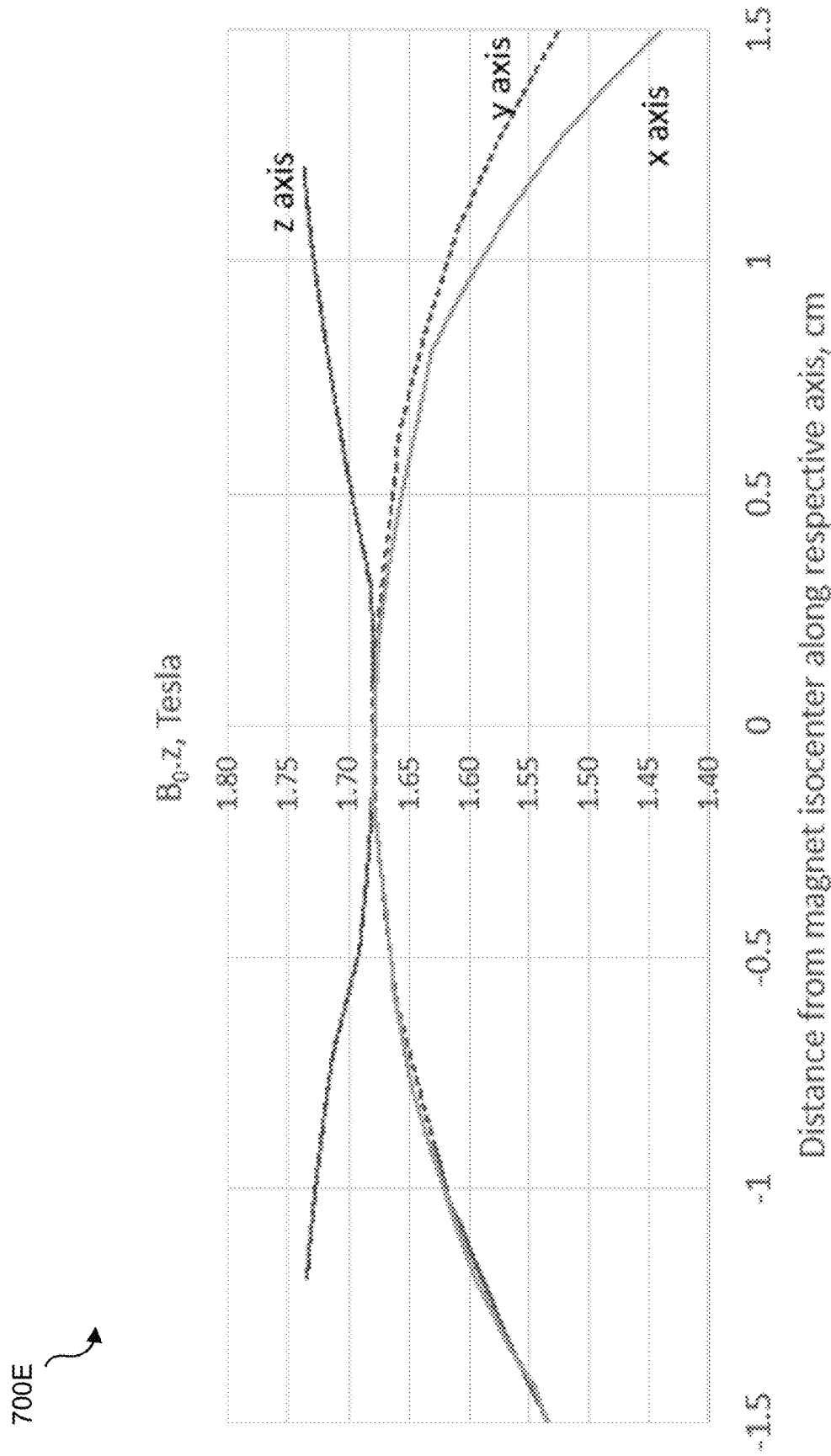
FIG. 7E shows a plot of a magnetostatic simulation of the static magnetic field ($B_0$) generated by the permanent magnet assembly of FIGS. 7A and 7B.

Referring now to FIG. 7E, there is shown a plot 700E illustrating a magnetostatic simulation of the static magnetic field ($B_0$) within the bore 106. In particular, plot 700E shows the static field along the z-axis in relation to the distance from the magnetic isocenter along the three Cartesian axis. As shown therein, the static magnetic field ($B_0$) is nearly uniform along the z-axis and the y-axis, but the uniformity is slightly compromised along the x-axis. Again, the non-uniformity along the x-axis is caused by loss of magnet volume in the central ring 706 as a result of the bore 106.

Figure 7G:
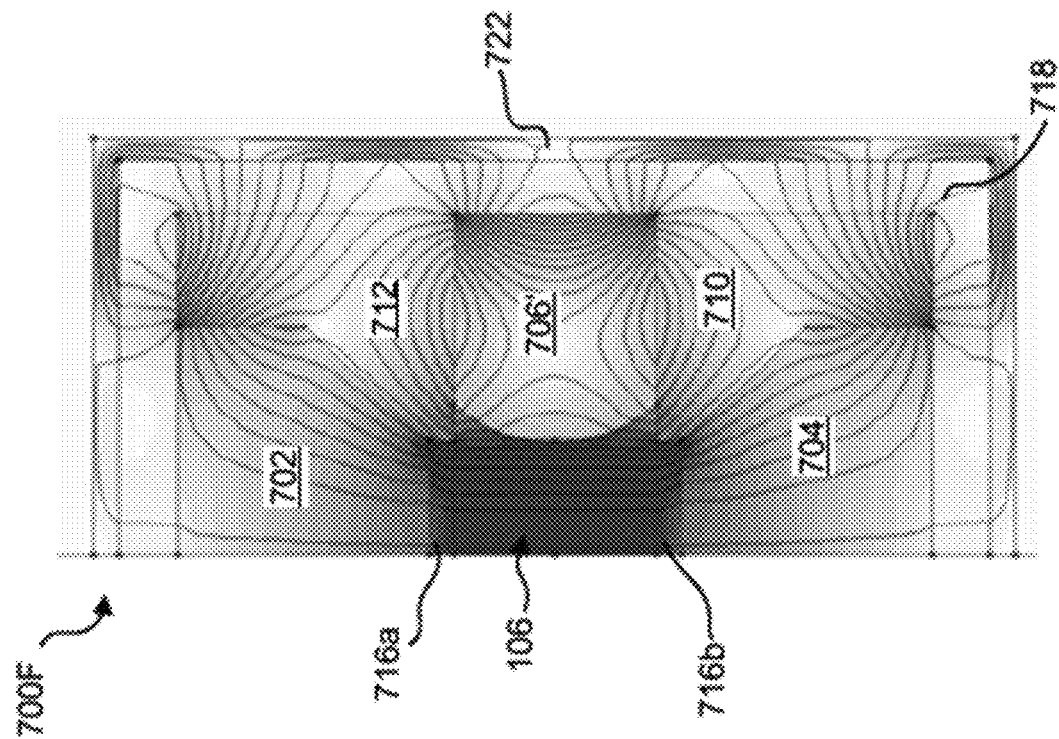
FIG. 7G shows a contour field plot generated by simulating the magnetic field components generated by the permanent magnet assembly of FIG. 7F.
Figure 7F:
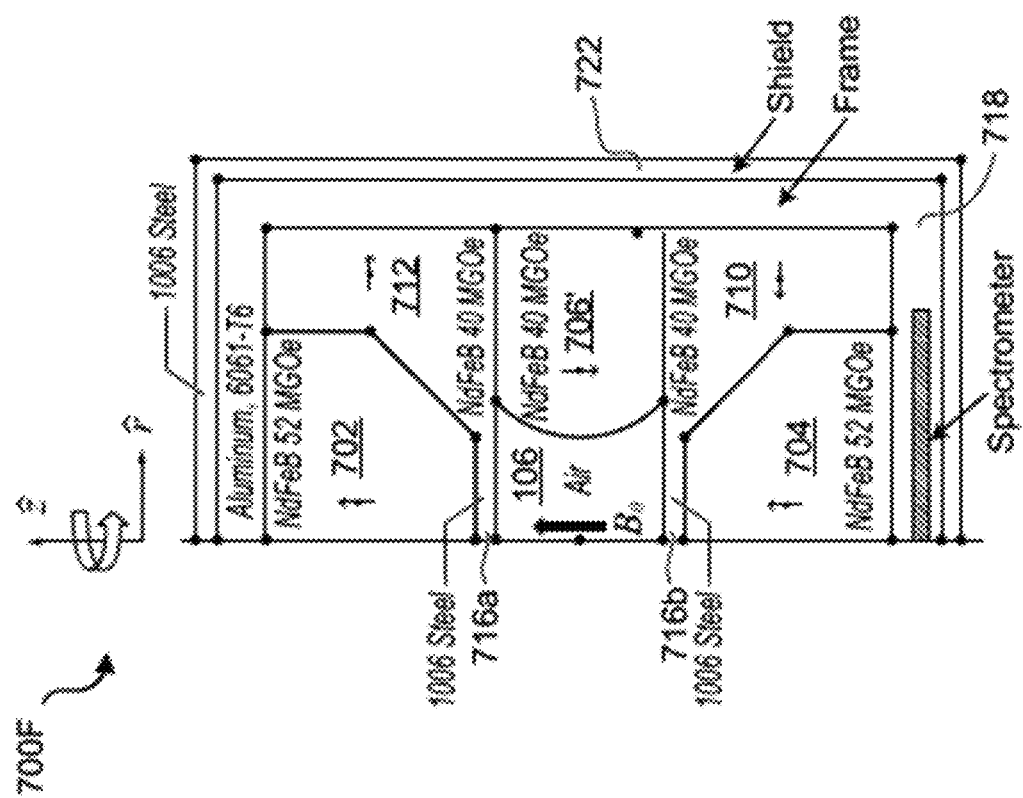
FIG. 7F shows a cross-sectional view of the portable NMR device along the section line 7-7' of FIG. 1A and illustrating a permanent magnet assembly located within the portable NMR device according to another example embodiment in accordance with the teachings herein.

Referring now to FIG. 7F, there is shown a permanent magnet assembly 700F of the portable NMR device 104 according to another example embodiment. In particular, the central ring segment 706' now includes an inner surface which is non-planar, and is defined by a semi-spherical protrusion into the magnet bore 106. Shaping the inner surface of the central magnet segment 706' in this manner may mitigate the reduced magnetic static field strength and the spatial non-uniformity of the static magnetic field which results from the loss of volume attributed to the bore 106.

In various embodiments, the inner surface protrusion of the central ring segment 706' may be formed from a separate pole piece which is formed of high permeability soft steel or other magnetic alloy.

Figure 7H:
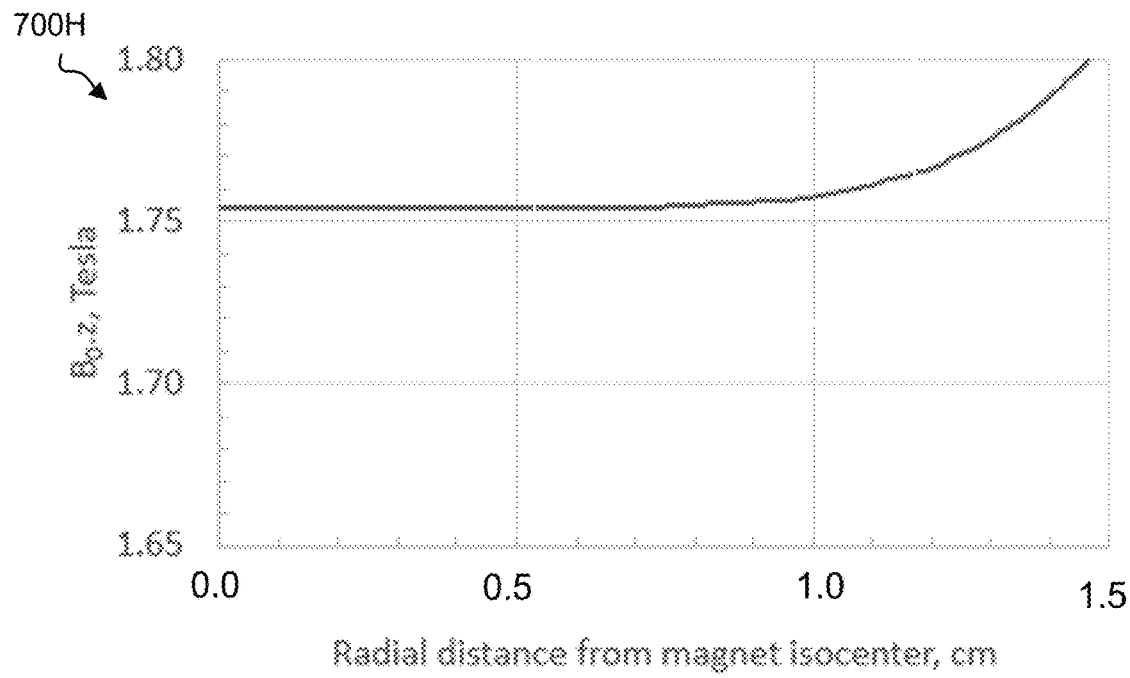
FIG. 7H shows a plot of the strength of the static magnetic field ($B_0$) generated by the permanent magnet assembly of FIG. 7F as a function of radial distance from the magnet isocenter.

Referring now to FIGS. 7G and 7H, there is shown the effect of deforming the inner surface of the central ring segment 706' as shown in FIG. 7F.

FIG. 7G shows the contour field plot for the permanent magnet assembly 700B. The static field uniformity is improved in the magnet bore 106 as compared to FIG. 7C.

FIG. 7H shows a plot 700H of the magnetic field strength as a function of radial distance (i.e., along the transverse plane XY) from the magnet isocenter, or the center of the magnet bore 106. In particular, plot 700H shows a significant improvement in field uniformity especially within 1 cm distance from the isocenter as compared with plot 700D.

While the axisymmetric permanent magnet design achieves a near homogenous static magnetic field across the magnet bore, as shown by the plots in FIGS. 7D and 7H, the static field is not perfectly homogenous, especially at extended distances from the magnet isocenter. Accordingly, in order to correct the spatial non-uniformity of the static magnetic field ($B_0$), the portable NMR device 104 may include a shimming assembly (see e.g., 424 of FIGS. 4A and 4B), located in the magnet bore 106, which generates a compensatory magnetic field to improve the homogeneity of the static field. In particular, the shimming assembly allows the static field uniformity to be under 0.1 ppm, and ideally within 0.01 ppm.

Figure 8A:
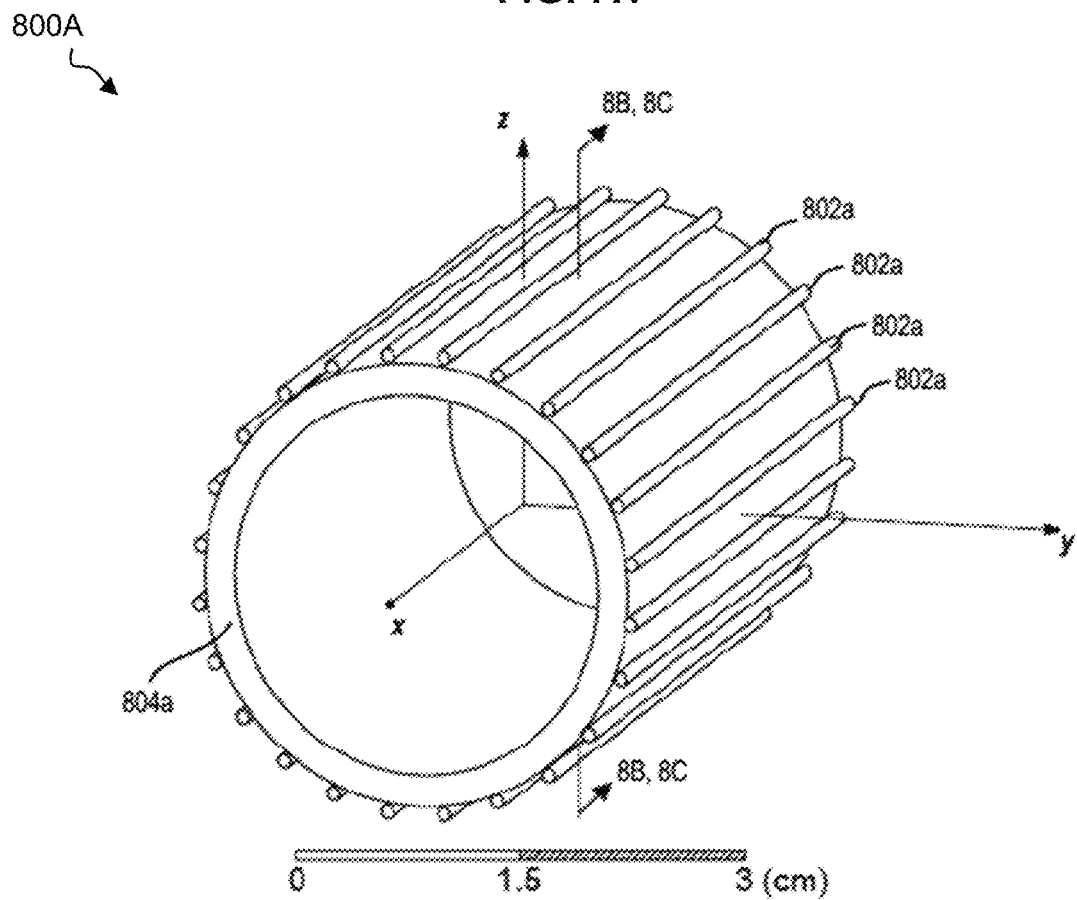
FIG. 8A shows an example shimming assembly according to at least one embodiment in accordance with the teachings herein.

Referring now to FIG. 8A, there is shown an example shimming assembly 800A according to some embodiments. The shimming assembly 800A may be analogous to the shimming assembly 424 of FIGS. 4A and 4B.

As shown, the shimming assembly 800A is formed from a plurality of current carrying conductors 802a which extend along the x-axis (as defined relative to the NMR device 104) and which are arranged in a circular configuration inside, or proximate, the bore 104 and are otherwise uniformly circumferentially spaced. Accordingly, the current carrying conductors form a "cylindrical" shape in three-dimension. In various cases, the current carrying conductors 802a may be positioned over a hollow cylindrical support frame 804a.

In particular, the shimming assembly 800A employs conductors 802a having uniform wire densities wherein each of the current carrying conductors 802a may receive an independently controlled direct current (DC) that may be supplied, for example, by a dedicated digital-to-analog (DAC) converter (e.g. using a multi-channel DAC converter). In various embodiments, the DAC converters may be located in the shimming control unit 422 of FIGS. 4A and 4B. To this end, the shimming control unit 422 may also include a plurality of current generators (not shown) coupled to the plurality of digital-to-analog (DAC) converters. In particular, the use of uniform wire densities with varying current is to be contrasted to conventional NMR shim designs which employ complicated wiring geometry using correction coils with variable copper winding densities.

As explained in further detail herein, the shimming assembly 800A uses a sinusoidal distribution of DC current magnitudes through the current carrying conductors which is varied vis-à-vis the angular position of the current carrying conductors around the "shell" of the hypothetical "cylinder" (e.g. formed by the arrangement of the current carrying conductors). This feature, in conjunction with the uniform circumferential spacing of the current carrying conductors, allows the shimming assembly 800A to generate high order mode magnetic field patterns in the magnet bore 104, which in turn, allow for accurate compensation of the non-uniformity of the static magnetic field ($B_0$) as explained herein. In particular, conventional shimming assemblies implement conductor coil geometries intended to produce a single magnetic field mode when driven by a current of magnitude proportional to that mode. Accordingly, these shimming assemblies are unable to provide accurate and precise compensation for static field non-uniformity without numerous and complex coil wiring geometries specific to each mode.

Further, and as explained in detail herein, the ability to variably control the current through each linear conductor allows a unique one-to-one mapping between the amplitude of the modal current, and the magnitude of a corresponding term in a polynomial decomposition of the uncompensated static magnetic field ($B_0$). That is, if the non-uniformity of the static magnetic field ($B_0$) is expressed as, or decomposed into, a polynomial (see e.g. FIG. 7E, wherein the non-uniformity plot may be approximated as an $n^{th}$ order polynomial), then the current in each conductor is adjustable to compensate for a corresponding term of that polynomial. Significantly, this allows the shim assembly to effect precise correction of the near-uniform static field. By extension, this allows the portable NMR device 104 to realize high field uniformities in the order of 0.01 ppm (or at least below 0.1 ppm), which has otherwise been unachievable using conventional shim assemblies. In particular, conventional shimming assemblies do not allow for a similar direct one-to-one mapping and otherwise do not permit for precise static field compensation to generate high static field uniformity as is useful in NMR applications.

It is also appreciated that the current shimming assembly 800A may be distinguished from conventional "bridge-cage coil" assemblies that may be used in conventional NMR application to generate homogenous RF magnetic field ($B_1$). In particular, conventional bird-cage RF coils have end cap rings that capacitive couple each "bar" of the bridge-coil to the next bar. As a result the bird-cage electrically is a cascade of C-L high pass filters, with capacitors between the bars on both end rings and the bar serving as a distributed inductance. Accordingly, this bridge-cage topology allows a single feed-in at the right frequency to establish resonance in the form of a sinusoidal distribution of current around the cage. Thus, the system provides a near-homogeneous $B_1$ field at a select radio frequency and circular polarization. However the bridge-cage topology cannot extend down to DC, as is the case with shimming assembly 800A, and can only generate higher mode field patterns at harmonics of the tuned RF frequency. Accordingly, by removing the end cap rings in shimming assembly 800A, and driving each conductor line with independent DC currents generated by multi-channel DAC(s), the shimming assembly 800A may generate any magnetostatic modal field pattern in the magnet bore 104. As previously mentioned, the ability to generate any modal field pattern allows for high correction to field non-uniformity of the static magnetic field ($B_0$).

Now in more detail, in order to generate the correction field using the shimming assembly 800A, the current density (I) in each current carrying conductor (also referred to herein as a "shim current mode") is varied sinusoidally. In at least some embodiments, the sinusoidal variation may be expressed according to Equation 21.

$$I = I_o \sin \theta \tag{21}$$

wherein $I_o$ is the magnitude of the current carried through a respective current carrying conductor, and $\theta$ is the angle of the current carrying conductor as measured counter-clockwise with respect to the z-axis.

Figure 8B:
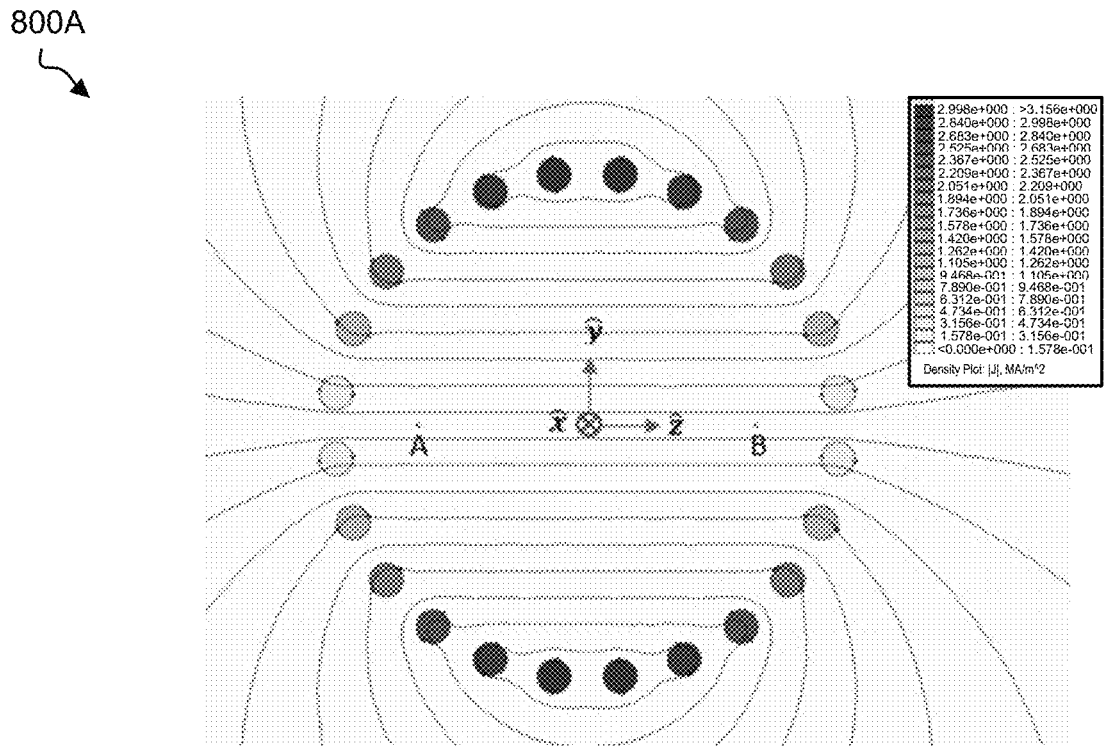
FIG. 8B shows a cross-sectional view of the shimming assembly of FIG. 8A along the cross-sectional line 8B-8B of FIG. 8A.

Referring now to FIG. 8B, there is shown a cross-sectional view of the shimming assembly 800A along the cross-sectional line 8B-8B' of FIG. 8A. As shown by the field stream lines illustrated therein, where the current density is varied according to Equation (21), the superimposition of the magnetic fields produced by each of the current carrying conductors generates a dipole field characterized by a linear compensatory field along the z-axis. In the illustrated example of FIG. 8B, the conductor current densities vary in a range between 0.42 MA/m² (million amperes per square meter) to 3.16 MA/m². The linear compensatory field along the z-axis may be accordingly used to compensate for the non-uniformity of the static magnetic field ($B_0$) along said z-axis.

In at least some other embodiments, the current density (I) in each current carrying conductor may be also varied according to Equation (22).

$$I = I_o \sin 2\theta \tag{22}$$

The effect of varying the conductor current according to Equation (22) is to generate a higher order quadruple mode field which is also characterized by a linear compensatory field along the z-axis.

Figure 8C:
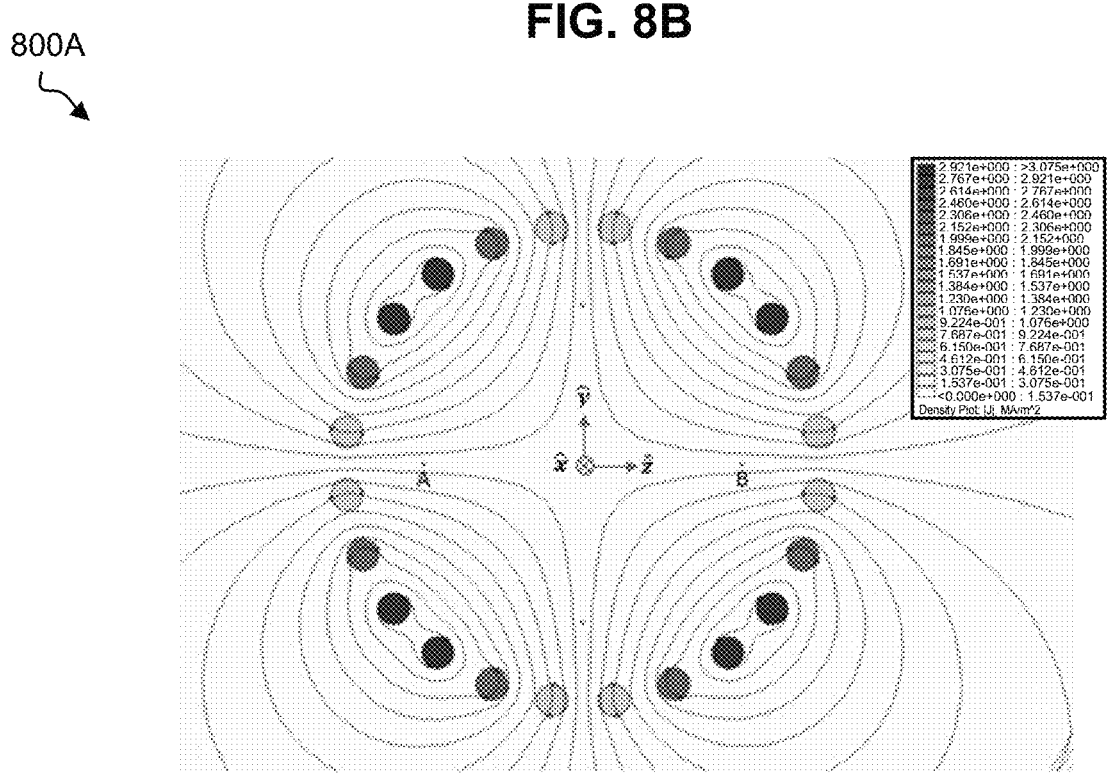
FIG. 8C shows a further cross-sectional view of the shimming assembly of FIG. 8A along the cross-sectional line 8C-8C of FIG. 8A.

Referring now to FIG. 8C, there is shown a further cross-section view of the shimming assembly 800A along the cross-section line 8C-8C' of FIG. 8A. As shown by the field stream lines illustration therein, where the current is varied in the current carrying conductors according to Equation (22), a quadrupole field is generated and the compensatory field along the z-axis is linear (while not shown, the field is also linear along the y-axis). In the illustrated example of FIG. 8C, the conductor current densities vary in a range between 0.82 MA/m² (million amperes per square meter) to 3.08 MA/m².

Accordingly, a 2n pole field may be generated using the shimming assembly 800A by varying the current density (I) in each current carrying conductor according to Equation (23).

$$I = I_o \sin n\theta \tag{23}$$

As explained above (and as explained in further detail herein), allowing the generation of higher order mode fields allows for more precise compensation of the non-uniform static magnetic field ($B_0$). This is because at higher order modes, the higher order terms may be correlated to a corresponding term in the polynominal expansion of the static magnetic field ($B_0$). Accordingly, the shim coil assembly 800A permits for a unique one-to-one mapping between the amplitude of each shim current mode and the magnitude of a corresponding term in a polynomial decomposition of the non-uniform static magnetic filed ($B_0$) (i.e., generated by the permanent magnet assembly).

The theory behind the unique one-to-one mapping of shim current mode to corresponding terms in a polynominal decomposition of the non-uniform static magnetic filed ($B_0$) will now be herein described in further detail.

The magnetic field generated by the combination of the static field ($B_0$) (i.e., generated by the permanent magnet assembly), and the compensatory field (i.e., generated by the shim coils), satisfies the governing magnetic equation expressed by Equation (24).

$$\nabla^2 \vec{A} = -\mu_0 \vec{J} - \mu_0 \nabla \times \vec{M} \tag{24}$$

where $\vec{A}$ is the vector magnetic potential, $\vec{J}$ represents current density in units of Amperes per square meter through the current carrying conductors, $\mu_0$ is the permeability of free space, and $\vec{M}$ represents the spatial magnetization of the permanent magnet structure. Given the high linearity of the hard-permanent magnets used in the permanent magnet assembly of the NMR device 104, it is possible to use the principle of superposition to consider the effects of the shim current and the permanent magnets separately.

In particular, the magnetic field (B) generated in the magnet bore 106 (i.e., as a result of the static field and the compensatory field) may be solved by first solving for the vector magnetic potential $\vec{A}$, and then solving for its curl. For the proposed current geometry, $\vec{A}$ is purely longitudinally directed (x-axis) and satisfies Laplace's equation expressed by Equation (25):

$$\nabla^2 A_x = 0 \tag{25}$$

Assuming that the conductors, extending along the x-axis, form a cylindrical shape having a radius $r_i$, and assuming a surface current is defined on the "shell" of the cylinder at radius $r=r_i$, then solutions of the Laplace's equation in Equation (25) can be found in both a first region defined by $r<r_i$ (region I) and a second region defined by: $r>r_i$ (region II), subject to the following continuity and normal derivative boundary conditions at $r=ri$ as provided by Equations (26) and (27).

$$A_I(r_i, \theta) = A_{II}(r_i, \theta) \tag{26}$$

$$\frac{\partial A_{II}(r, \theta)}{\partial r} - \frac{\partial A_I(r, \theta)}{\partial r}\bigg|_{r=ri} = -\mu_0 \sum_{n=1}^{N} K_{no}\sin n\theta + K_{ne}\cos n\theta \tag{27}$$

wherein $\theta$ is the angle with respect to the z-axis, $K_{no}$ and $K_{ne}$ are the $n^{th}$ odd and even mode sheet current densities in units of amperes per meter along the circumference of the cylinder, and N is the shim current mode.

It has been appreciated that the sheet current boundary condition given by a Fourier Series on a basis of circular harmonics is appropriate for the longitudinal symmetry of this ideal 2D device geometry and can produce any desired compensatory magnetic field (B) field distribution within the bore as N (the shim mode) approaches infinity.

In particular, for an arbitrary current distribution of order N, ideally distributed on an infinitesimally thin cylindrical shell of radius $r_i$, the magnetic field (B) field in the bore $r<r_i$ may be expressed according to Equation (28).

$$\vec{B}(r, \theta) = \frac{\mu_0}{2} \tag{28}$$

$$\sum_{n=1}^{N} \left(\frac{r}{r_i}\right)^{n-1} \left[(K_{no}\cos n\theta - K_{ne}\sin n\theta)\hat{r} - (K_{ne}\cos n\theta + K_{no}\sin n\theta)\hat{\theta}\right]$$

Further, the magnetic field (B) outside the cylindrical bore where $r>ri$ may be expressed according to Equation (29).

$$\vec{B}(r, \theta) = \frac{\mu_0}{2} \tag{29}$$

$$\sum_{n=1}^{N} \left(\frac{r_i}{r}\right)^{n-1} \left[(K_{no}\cos n\theta - K_{ne}\sin n\theta)\hat{r} - (K_{ne}\cos n\theta + K_{no}\sin n\theta)\hat{\theta}\right]$$

It is evident at least from Equation (28) that there is a direct correspondence between the $n^{th}$ odd harmonic of the shim current mode, and a $z(n^{-1})$ dependence of the tangential compensatory magnetic field (B) magnitude along the z-axis ($\theta=0$, $\hat{r}=\hat{z}$) within the cylinder bore.

Accordingly, this $B_0$ field modal analysis demonstrates a unique one-to-one mapping between the required amplitude of each shim current mode and the magnitude of the corresponding term in a polynomial decomposition of the tangential magnetic field ($B_0$).

However, these shim currents are only approximations to ideal sheet currents which do not otherwise account for the spatial sampling at uniform angles and the finite current density over each shim conductor cross-section. A shim structure with M conductors limits polynomial correction order to $N=M/2-1$. A good test of the theory is to relate current in the $l^{th}$ conductor to the ideal sheet current and use the result to predict static field ($B_0$) strength. Dividing the circumference of the cylinder into M zones with even angular spacing around each shim conductor, current mode n in the $l^{th}$ conductor is a line integral of the sheet current in zone 1 given by Equation (30).

$$I_{ln} = \int_{\theta_l - \pi/M}^{\theta_l + \pi/M} (K_n \sin n\theta) r_i d\theta = \frac{2r_i K_n}{n} \sin n\theta_l \sin\frac{n\pi}{M} \tag{30}$$

In the above expression, only the odd mode currents are retained (and subscript o dropped) because the static field ($B_0$) along the x-axis results from odd mode sheet current distribution. For low order modes in a shim structure with enough conductors, $\sin n\pi/M \approx n\pi/M$ so that the Equation (30) simplifies to Equation (31).

$$I_{kn} \cong \frac{2\pi r_i}{M} K_n \sin n\theta_k \tag{31}$$

As noted previously the $B_0$ dipole field in the bore is associated with mode $n=1$, accordingly Equation (29) resolves to Equation (32).

$$B_0(0, 0) = \frac{\mu_0 K_{n=1}}{2} = \frac{\mu_0}{2r_i}\left(\frac{M}{2\pi}\right)\frac{I_{k_1}}{\sin\theta_k} \tag{32}$$

This model predicts a 1A peak current in mode 1 ($\theta_k=\pi/2$) produces a 0.16 mT $B_0$ field at magnet isocenter with bore radius of 1.5 cm and 24 shim conductors. While, it may be standard practice to take the $B_0$ field at magnet isocenter as the "true" value and only shim $n\geq 2$ higher order modes, however, $n=1$ modal analysis demonstrates the relative strength of the shim system and provides a good test of the theory as it agrees well with empirical results.

In practice, each shim current mode produces a compensatory field that is best described by an Nth order polynomial with a dominant term, albeit with several non-negligible additional terms. Let $S_{ij}$ denote the coefficient of the $x^i$ term of a polynomial fit to the field produced by the PI current mode with all other shim currents off. These field response polynomials for each shim current mode can be determined experimentally. If the uncompensated static field ($B_0$) is written as an $N^{th}$ order polynomial expressed by Equation (33) then the currents needed to shim the system can be found by solving Equation (34).

$$B_0(z) = B_0 + \Delta B_{01}z + \Delta B_{02}z^2 \ldots \Delta B_{0N}z^N \quad (33)$$

$$\begin{pmatrix} -\Delta B_{01} \\ \vdots \\ -\Delta B_{0N} \end{pmatrix} = \begin{pmatrix} S_{11} & \cdots & S_{1N} \\ \vdots & S_{ij} & \vdots \\ S_{N1} & \cdots & S_{NN} \end{pmatrix} \begin{pmatrix} I_1 \\ \vdots \\ I_N \end{pmatrix} \quad (34)$$

where elements of the current column vector are the modal currents.

It may be observed that the matrix describing this linear system is strongly diagonal and thus well-conditioned and invertible. Conventional shim coil geometric configurations that do not directly correspond to the modal properties of the system may result in ill-conditioned matrix formulations that require calculation of a pseudo-inverse. Field homogenization performance may be compromised in this scenario.

In various cases, the method of resolving shim currents using Equations (33) and (34) may be suited when the shim assembly is used with a traditional Halbach magnet array designs defined by longitudinal symmetry.

Figure 8D:
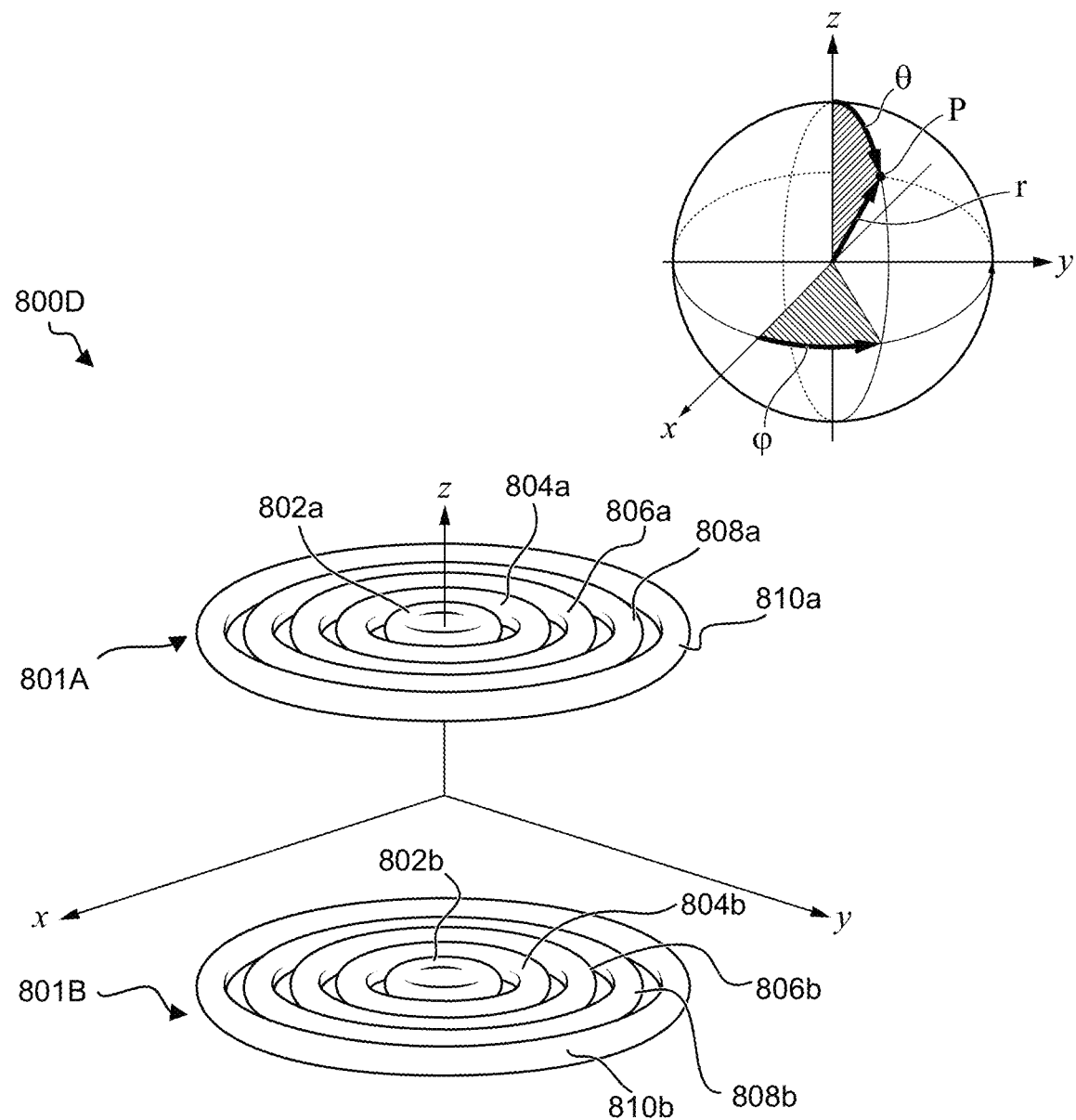
FIG. 8D shows a further example shimming assembly according to at least one embodiment in accordance with the teachings herein.

Referring now to FIG. 8D, there is shown a shimming assembly 800D according to another example embodiment. In particular, shimming assembly 800D may represent an implementation of the shimming assembly 800A of FIG. 8A which is more suited for the axisymmetric permanent magnet design shown in FIG. 7A or 7F. The theoretical principles underlying the shim assembly 800D are similar to the theoretical principles explained above in respect to the shim assembly 800A.

As shown, the shimming assembly 800D includes two parallel sets of laterally spaced concentric loops 801A, 801B which may be positioned on the top and bottom surfaces of the cavity 106 such that the centers of the concentric loops are collinear with the axis of the static magnetic field ($B_0$) (e.g., the z-axis in FIGS. 7A and 7F). Each set includes multiple concentric loops which rotate around the axis of the static magnetic field. In particular, the concentric loops 801A, 801B on the top and bottom surfaces form a plurality of spaced and opposed concentric loop pairs 802a, 804a, 806a, 808a, and 810a as well as 802b, 804b, 806b, 808b, and 810b, respectively. In various cases, at least one current carrying conductor pair may be configured such that a coil radius, of each coil in the conductor pair, is substantially equal to the spacing between the respective coils of the conductor pair. Accordingly, this may satisfy the reverse Helmholtz condition if the current drives of the two coils are in opposite directions (e.g., clockwise versus counter-clockwise) which allows the coil pairs to generate a linear field gradient between the two coils.

In various embodiments, each of the centric loops carries an independent current and generates a field profile on the axis of symmetry (e.g. the z-axis). While the field profile is analytically known in closed form in a similar manner as discussed above with respect to shimming assembly 800A, a polynomial expansion of the magnetic field generated by each coil using spherical harmonics may be better for evaluating the suitability of the concentric coils 800D for uniformly compensating the static field ($B_0$).

In particular, the magnetic field components generated by a circular shim coil, in assembly 800D, having a radius ($a$) positioned relative to the magnet isocenter at polar angle ($\alpha$), can be expressed in spherical harmonics using Equations (35) and (36). Equation (35) expresses the radial (r) directed component of the field, and Equation (36) expresses the polar angle ($\theta$) directed component. Equations (35) and (36) apply in regions within the radius of the shim coil (e.g., r>a).

$$B_r(r, \theta) = \frac{\mu I}{2a}\sin\alpha \sum_{n=1}^{\infty} \left(\frac{r}{a}\right)^{n-1} P_n^1(\cos\alpha)P_n(\cos\theta) \quad (35)$$

$$B_\theta(r, \theta) = -\frac{\mu I}{2a}\sin\alpha \sum_{n=1}^{\infty} \frac{1}{n}\left(\frac{r}{a}\right)^{n-1} P_n^1(\cos\alpha)P_n^1(\cos\theta) \quad (36)$$

wherein I is the current (A) applied to the shim coil, $P_n$ are the Legendre polynomials, and $P_n^1$ are the associated Legendre polynomials of the first kind (W. R. Smythe[3]).

In the illustrated example embodiment of FIG. 8D, each coil in sets 801A and 801B is positioned relative to the magnet isocenter at a polar angle ($\alpha$) defined by $\alpha=\tan^{-1} a/h$, wherein ±h is height of the coil above or below the plane z=0. For the ideal axisymmetric design for the permanent magnet structure (e.g., magnet 700F of FIG. 7F), there is no azimuthal magnetic field component, or dependence on $\varphi$ the azimuthal angle. Further, on the axis of symmetry, where $\cos\theta=1$, the field is purely radially directed (r=z) which results from $P_n^1(1)=0$ and $P_n(1)=1$ for all values of n.

Each closed circular coil in coil sets 801A and 801B generates both even and odd Legendre polynomial terms in Equations (35) and (36), rather than a single dominant mode. Further, coils of different radii generate Legendre polynomial coefficient vectors that are linearly independent. In particular, this is owing to the fact that Legendre polynomial coefficients depend on powers of the coil radius (a). In particular, by uniquely expressing the field generated by the shim coils using an infinite series expansion on spherical harmonics, and demonstrating that each coil generates even and odd polynomial terms (rather than only a single dominant mode), it can be appreciated that the shim assembly can be used to form a complete basis to produce any desired compensatory field (e.g., any desired field pattern) in a bore 106 of an axisymmetric permanent magnet assembly defined by azimuthal symmetry.

It will be further appreciated that the separability of the magnetic field equations in the radial (r) and polar ($\theta$) directions implies that corrections to the field along an axis co-linear to the magnetic field (e.g., the z-axis in the magnet design of 7F) to make it uniform will ensure that the field everywhere within the bore of the magnet will be made uniform. In particular, this fact results from the axisymmetric design of the permanent magnet, and greatly simplifies the shimming process.

Figure 11:
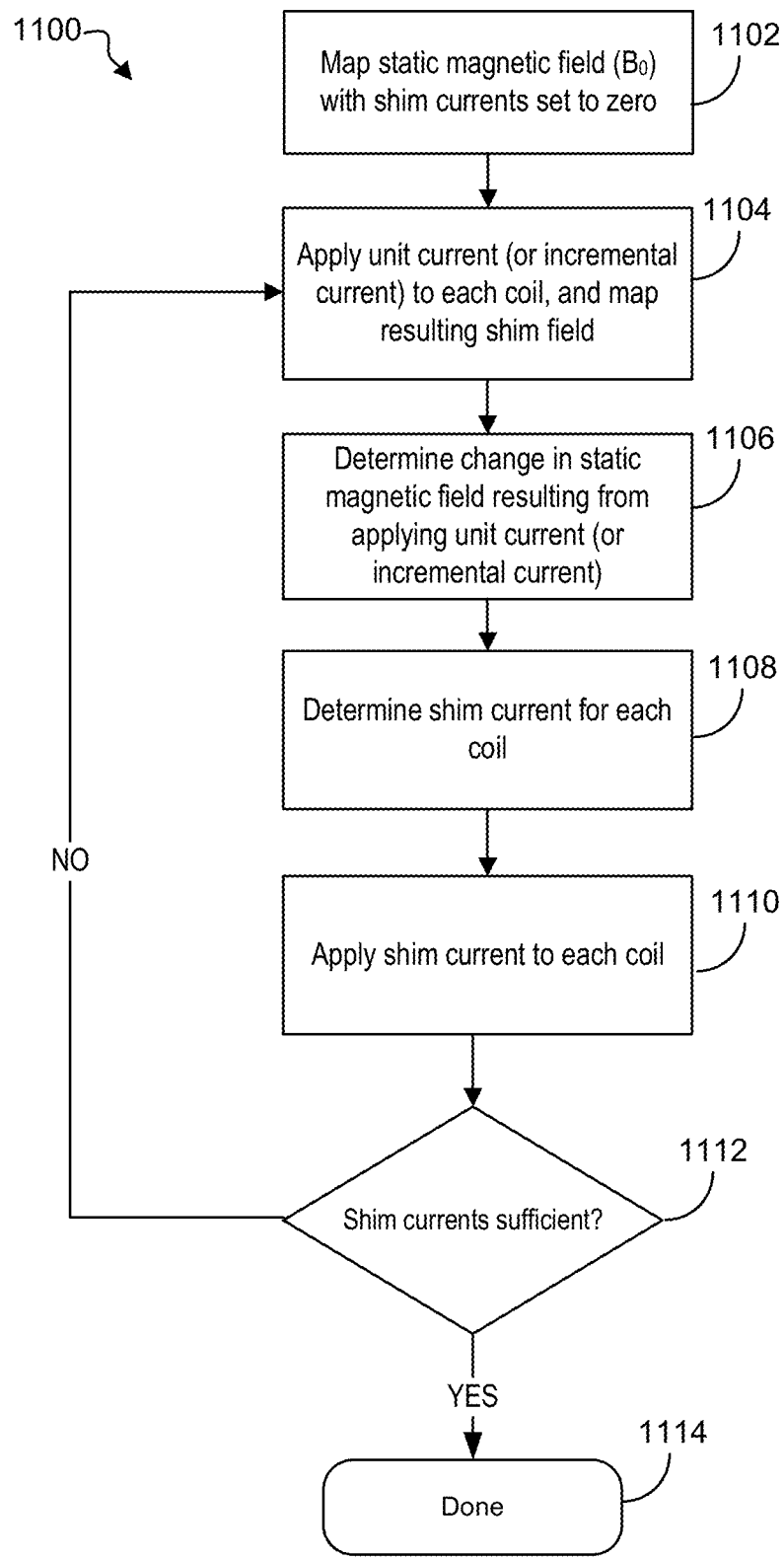
FIG. 11 is a flow chart of an example method for adjusting currents for shim coils in the shimming assembly of FIG. 8D to correct for static magnetic field ($B_0$) non-uniformity in the bore of an axisymmetric magnetic.

Referring now to FIG. 11, there is shown an example process flow for a method 1100 for calculating currents for each shim coil in shimming assembly 800D to correct for static magnetic field ($B_0$) non-uniformity in an axisymmetric magnetic design (e.g., magnet design 700F in FIG. 7F).

At act 1102, the static magnetic field ($B_0$) is mapped while all shim currents are set to zero A field map of the uncompensated static magnetic field ($B_0$), along the z-axis (e.g., FIG. 7F), is then generated by a gradient imaging technique. In various cases, the gradient imaging technique uses a linear one-dimensional gradient applied along the static field axis (e.g., the z-axis). The linear gradient can be generated, for example, using the same shimming apparatus 800D of FIG. 8D located inside of the magnet bore, or otherwise, using the coil assembly 800A of FIG. 8A oriented orthogonally to the static field axis (e.g., along the x-axis) in the magnet bore. The gradient imaging technique is generated using a test sample of uniform proton density (e.g., a water sample) located in the bore. In various cases, Discrete Fourier Transform (DFT) pairs may also be used to convert from k-space dimensions to the field sampled along the axis of the gradient. In some embodiments, the field profile can be expressed as an $P^{th}$ order polynomial as shown in Equation (37).

$$B_0(z)=B_0+\Delta B_{01}z+\Delta B_{02}z^2\ldots \Delta B_{0N}z^P \quad (37)$$

In other embodiments, the static field profile ($B_0$) along the z-axis can be expressed according to a column vector. The column vector may be an Mx1 vector, representing the non-compensated static field along the z-axis ($B_0(z)$), wherein M is the number of equally spaced apart points sampled along the z-axis. The static field non-uniformity error ($\Delta B_0(z)$) may then be determined according to Equation (38).

$$\Delta B_0(z)=B_0(z)-B_0(0) \quad (38)$$

wherein $B_0(0)$ is the vector for a uniform, compensated static field along the z-axis.

At act 1104, a unit current is separately applied to each coil in coil assembly 800D, and the resulting magnetic field for each coil is separately mapped. In subsequent iterations of method 1100, as explained in further detail herein, an incremental current can be applied to each shim coil which is additional to the shim current values determined at act 1108 in a previous iteration of method 1100. Similar to shimming assembly 800A, the currents applied to the concentric loops may be applied by the current shimming control unit 422 of FIGS. 4A and 4B. To this end, the shimming control unit 422 may include a plurality of current generators (not shown) and a plurality of digital-to-analog (DAC) converters, wherein each DAC is coupled to one of the current generators and one of the concentric loops to provide a unique current thereto.

At act 1106, the static magnetic field ($B_0$) profile determined at act 1102 is subtracted from each magnetic field determined at act 1104 for each coil. In the first iteration of method 1100, this allows determination of the static magnetic field generated from applying a unit current to each coil. In particular, for the $j^{th}$ coil, the magnetic field profile along the z-axis (e.g., the static field axis) may be expressed according to an Mx1 dimension column vector ($S_j$). In subsequent iterations of method 1100, act 1106 allows for the determination of the static filed generated from applying an incremental current, which is additional to the shim current values determined in the previous iteration of method 1100.

At act 1108, the shim currents required for each coil to generate a uniform static field in the magnet bore is determined.

In particular, thee static bore magnetic field, resulting from the combination of coil fields determined at act 1106, can be assumed to be a linear superposition of the magnetic field generated by each shim coil. Accordingly, the currents required to shim the spatial non-uniformity in the static magnetic field ($B_0$) can be determined according to the followed linear system expressed by Equation (39).

$$\begin{pmatrix} -\Delta B_{01} \\ \vdots \\ -\Delta B_{0M} \end{pmatrix} = \begin{pmatrix} S_{11} & \ldots & S_{1N} \\ \vdots & S_{ij} & \vdots \\ S_{M1} & \ldots & S_{MN} \end{pmatrix} \begin{pmatrix} I_1 \\ \vdots \\ I_N \end{pmatrix} \quad (39)$$

The shim matrix S is rectangular because the number of points (M) sampled along the z-axis is greater than the number of shim coils (N).

The shim currents required to generate a uniform static field in the magnet bore can be determined by solving the linear system expressed in Equation (39). This can be done by inverting the product of the shim matrix with its transpose as shown in Equation (40).

$$I=(S^TS)^{-1}S^T(-\Delta B_0) \quad (40)$$

At 1110, the currents determined for each shim coil in Equation (40) may then be applied to the shimming assembly 800D in order to correct for non-uniformity in the static field ($B_0$) inside the magnet bore. For example, as explained previously, this can be done using the shimming control unit 422 which includes a plurality of current generators (not shown) and a plurality of digital-to-analog (DAC) converters, wherein each DAC is coupled to one of the current generators and one of the concentric loops to provide a unique current thereto.

In various cases, method 1110 may require several iterations to resolve the shim currents which result in a uniform static field ($B_0$). These iterations result from the non-linearity in the permanent magnet B(H) characteristic, which violates the assumption of linear superposition in Equation (39). In particular, the middle ring magnet (e.g., 706 in FIG. 7A, or 706' in FIG. 7F) often operates with a high reverse coercive field in its non-linear B(H) region. Accordingly, at 1112, it can be determined if the shim currents applied at 1110 are sufficient to provide a threshold uniformity for the static field (e.g., less than 0.1 ppm). This determination can be made, for example, by mapping the static field generated by the shim assembly in a manner similar to that described at act 1102. However, contrary to act 1102, the static field is not profiled by setting the shim currents to zero, but rather, by applying the shim currents determined at act 1108.

In cases where the shim currents are not determined to be sufficient at act 1112, method 1100 can return to act 1104, and re-iterate. As explained previously, in subsequent iteration of method 1100, an incremental current (e.g., incremental to the current determined at act 1108 in the previous iteration) is applied to each coil.

In other cases, where the shim currents are determined to be sufficient at act 1112, method 1100 may be otherwise determined to be complete at act 1114.

As the permanent magnet assembly 700A and/or 700F generates a more spatially uniform static magnetic field ($B_0$) than traditional Halbach magnet arrays, the shimming assembly 800D will generally require less current (I) in order to provide sufficient field correction to achieve field uniformity of less than 0.1 ppm. In at least some cases, the required current may be provided by a small portable power source (e.g. a Li-Ion battery) which may be easily disposed within the frame 718 of the portable NMR device 104. This is in contrast to current compact permanent magnet designs which require large magnetomotive forces measured in hundreds or thousands of ampere-turns to correct the static field non-uniformity. The power source required to supply these levels of currents is incompatible with a small portable NMR device.

Figure 8E:
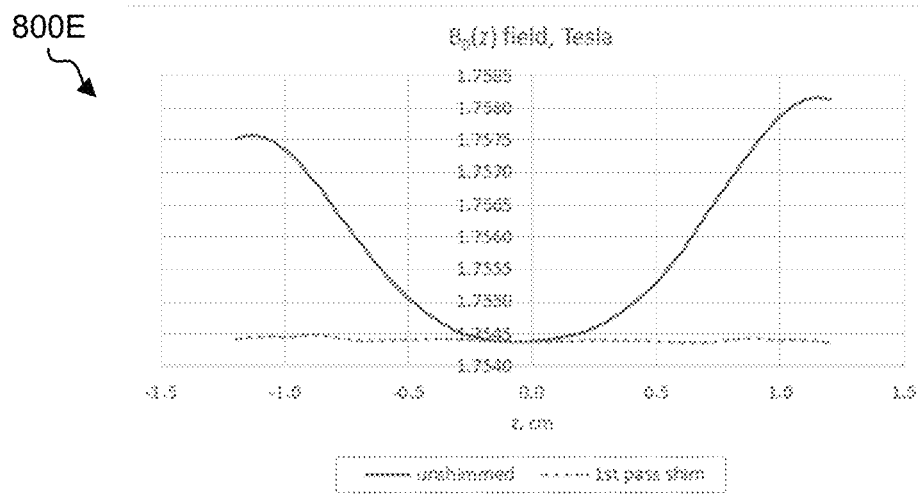
FIG. 8E shows an example plot of simulation results which compare the profile of a static magnetic field ($B_0$) inside of a bore of an axisymmetric magnet array, before applying shim currents to the shim assembly of FIG. 8D, and after applying a first iteration of a method for adjusting currents in each shim coil to compensate for static field non-uniformity.

Referring now to FIG. 8E, there is shown an example plot 800E of simulation results comparing the profile of the uncompensated static magnetic field ($B_0$), along the field axis in the bore of an axisymmetric magnet (e.g., the z-axis in the bore of magnet 700F of FIG. 7F), before applying shim currents to the shim assembly 800D, and after a first iteration of method 1100. The simulation results of FIG. 8E assume that each of the first and second coil sets 801A and 801B, of coil assembly 800D, include eight coils. As shown, a single iteration of method 1100 is able to generate substantially greater static field ($B_0$) uniformity in the magnet bore along the field axis.

Figure 8F:
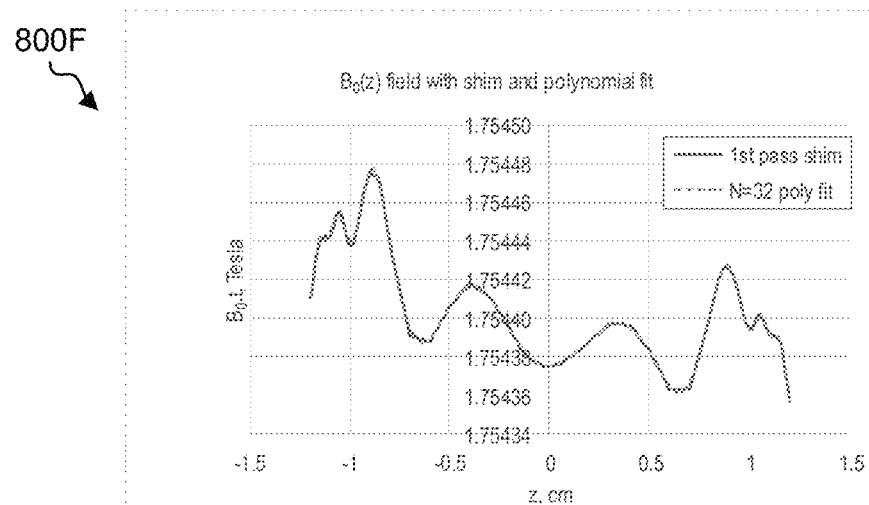
FIG. 8F shows an example plot of an expanded scale view of the first iteration shim result of FIG. 8E, overlaid by a high order polynomial fit.

Referring now to FIG. 8F, there is shown an example plot 800F showing an expanded scale view of the first pass shim result of FIG. 8E, and overlaid by a high order (32-order) polynominal fit. The first pass shim result has an RMS error of 15 ppm. It will be appreciated that with further iterations of method 1100, the RMS error may be reduced.

Figure 8G:
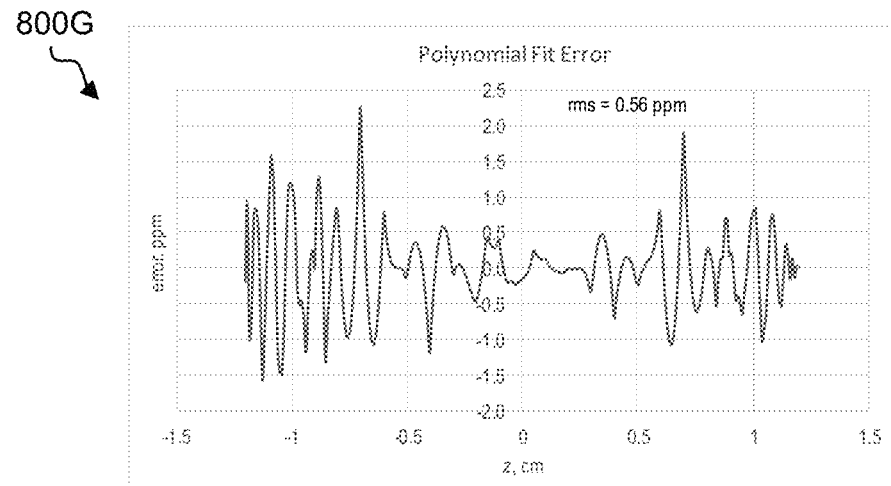
FIG. 8G shows a plot of the polynomial fit error resulting from the polynomial fit of FIG. 8F.

Referring now to FIG. 8G, there is shown a plot 800G of the residual error using the high order polynomial fit of FIG. 8F. As shown, the high order polynomial fit reduces the RMS error of the field to 0.56 ppm. As stated previously, the RMS error can be reduced by further iterations of method 1100.

Figure 8H:
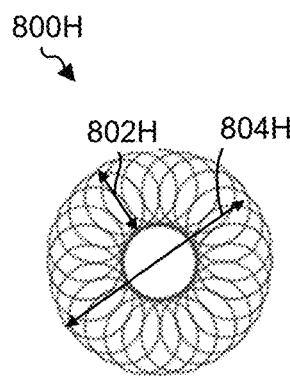
FIG. 8H shows an example configuration for the shimming assembly of FIG. 8D according to at least one embodiment in accordance with the teachings herein.
Figure 8I:
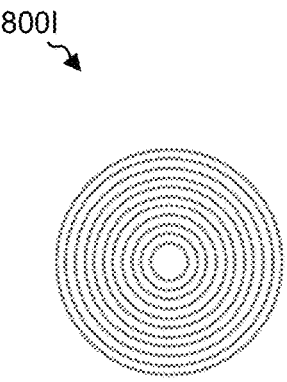
FIG. 8I shows another example configuration for the shimming assembly of FIG. 8D according to at least another embodiment in accordance with the teachings herein.
Figure 8J:
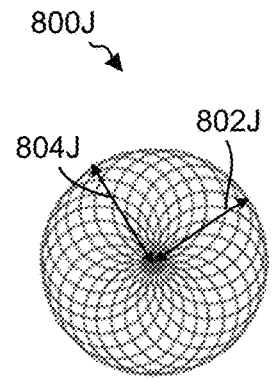
FIG. 8J shows still another example configuration for the shimming assembly of FIG. 8D according to still another embodiment in accordance with the teachings herein.

Referring now to FIGS. 8H 8J, there are shown different variations for shim coil configurations. In particular, the coil configuration shown in FIGS. 8H and 8J can be used to correct for azimuthal variation resulting from spatial variation in the magnetization strength and/or magnetization direction of a permanent magnet. Correcting for azimuthal variations may allow the method 1100 to be more effective in homogenizing the field in "r" (radial) and "theta" directions.

FIG. 8I shows a coil configuration 800I which is a similar configuration to the coil assembly 800D of FIG. 8D. In particular, this configuration includes nested concentric coils designed to correct field in the "theta" and "r" (radial) dimensions.

FIG. 8H shows an alternative example configuration 800H where twenty four shim coils are provided at 15 degree offsets, and whereby the coil diameter 802H is equal to one-third of the diameter 804H of the disk configuration formed by the combined coil set. The current feeds and returns are at right angles to the plane of the coils. In various cases, the configuration 800H can be used to correct for azimuthal variation of the field. In other cases, the shim coils may be offset at angles lower than 15 degrees to provide more resolution for field correction. In other cases, higher angular offsets may also be used to simplify manufacturing. In some cases, the offset angle can be in a range of 10 degrees to 45 degrees. Further, more or less than twenty four coils can be included in each coil set 801A and 801B, and the coils may have a coil diameter 802H which is less than or equal to the disk diameter 804H.

FIG. 8J shows a further example configuration 800J where twenty four shim coils are positioned at 15 degree offsets and the coil diameter 802J is equal to the disk radius 804J. In various cases, the configuration 800J can also be used to correct for azimuthal variation of the field.

In particular, in each of configurations 800H and 800J, the correction to the field in the azimuthal direction is a result of the center of each coil being positioned at a unique angular coordinate ($\varphi$). Accordingly, when the current in each coil is different, then the z-directed static field ($B_0$) will have a dependence on the azimuthal coordinate ($\varphi$). It will also be appreciated that while the coil configurations 800H and 800J are designed to produce field corrections that vary with azimuthal angle, these configurations also produce field dependency in the radial and polar coordinates. In contrast, the coil configuration 800I generates fields that do not have azimuthal dependence given their symmetry. Accordingly, in cases where shimming is performed using coil configurations 800H and 800J, the coils are used first to compensate non-uniformity in the azimuthal direction, then a 1D gradient shim along the static field axis (e.g., the z-axis) using the coil configuration 800I can complete the process.

Figure 9:
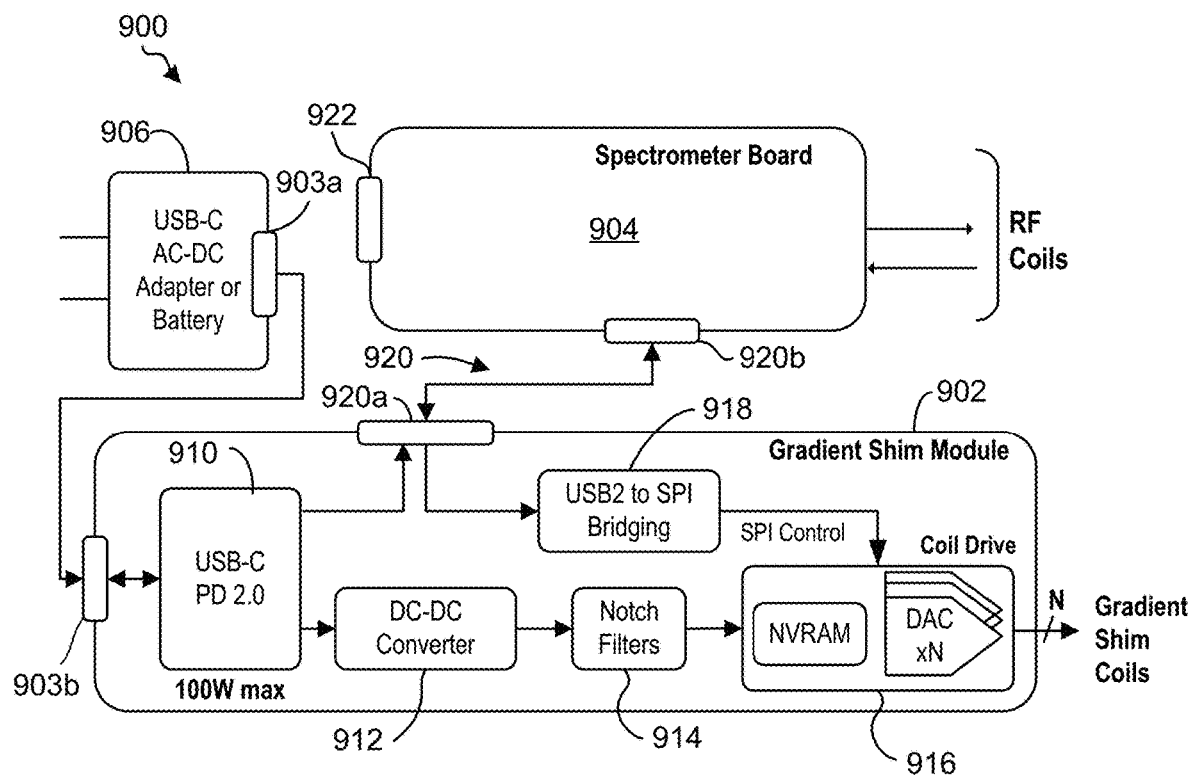
FIG. 9 shows an example block diagram of a power and control system for a portable NMR device.

Referring now to FIG. 9, there is shown an example block diagram for a power and control system 900 for a portable NMR device.

As shown, the power and control system 900 includes a gradient shim module (GSM) 902 and a spectrometer board 904. The gradient shim module 902 can be used for powering the gradient shim coils (e.g., shim coils 424 of FIG. 4B, or shim coils 800a of FIG. 8A or 800D of FIG. 8D). The spectrometer board 904 can be used for powering the spectrometer (e.g., spectrometer transmitting unit 416 and spectrometer receiving unit 420 of FIG. 4B). In various cases, each of the GSM 902 and spectrometer board 904 may comprise a circuit board, such as a printed-circuit board (PCB).

The GSM 902 may receive power from a power module 906. Power module 906 may be analogous to power module 412 of FIG. 4A. For example, as explained previously, power module 906 may be a compact battery that is configured to be received within the portable NMR device 104 (e.g., a lithium-ion (Li-Ion) battery), or may be an AC-DC power adapter to receive power from an external AC source. In various cases, power may be delivered from the power module 906 to the GSM 902 via a USB-C interface. For instance, the power module 906 may include a USB port 903a which may be in communication with a USB port 903b of the GSM 902 via a USB cable 903. In at least some cases, the USB cable 903 can be a USB-C cable such that power is delivered from the power source 906 to the GSM 902 via USB-C interfaces. Accordingly, the GSM 902 can include a USB-C Power Delivery protocol compliant port 910. In particular, a USB-C port may allow the system to negotiate a power contract with a USB-C compliant AC power adapter or battery pack for just the power required. Generally, a power contract occurs when both sides of a USB Type-C cable agree upon the power level to be transferred from the power source 906 to the power-receiving device (e.g., GSM 902). In various cases, this may allow conservation of power by avoiding dissipation of power that otherwise may be required for a design accommodating the worst-case magnet non-uniformity and associated shim current.

In at least some cases, the GSM 902 may also include a DC-DC converter 912 for supplying power to the shim coils. As the shim field magnitude is proportional to current, rather than power, the use of a DC-DC converter 912 may allow conversion of the USB-C maximum power delivery of 100 W (20V, 5A) to a lower voltage with higher current capacity (for example 5V, 20A). In various cases, as the DC-DC converter 912 may generate switching noise which may degrade the shim, the GSM 902 may also include a notch filters 914 for noise reduction. The output of the DC-DC converter 912 is coupled to the input of the notch filters 914. The output of the notch filters 914 may then be used for powering the coil drive 916, which may include a non-volatile memory random-access (NVRAM) memory, as well as DACs coupled to the shim coils of the shim assembly. The NVRAM may store shim current values (e.g., determined using method 1100) for each shim coil after the NMR system has been shut-down. Accordingly, this prevents the need to re-determine appropriate shim values each time the system is powered-on. In various cases, the number of DACs may be equal to the number of shim coils. Alternatively, a multi-channel DAC may be used that has D channels where D is the number of shim coils.

In at least some embodiments, the connection between the GSM 902 and the spectrometer board 904 may occur through a USB interface 920 (e.g., a USB-C interface) that provides power from the GSM 902 to the Spectrometer 904, and also transmits control data from the spectrometer board 904 to the GSM 902. In some cases, control and data information may be transmitted using a USB 2.0 serial bus which is embedded in a USB-C interface. The GSM 902 may also include a USB2 to Serial Peripheral Interface (SPI) bridge 918 for relaying control signals received from the spectrometer board 904, via the USB interface 920, to the coil drive 916. In various cases, the partitioning between the GSM 902 and the Spectrometer board 904 facilitates system integration and packaging, and accommodates different design rules and regulatory requirements for the high-power DC and sensitive RF functions.

In at least some cases, the Spectrometer board 904 may also include a USB port 922 (e.g., a USB-C port) which may be used to connect the Spectrometer board 904 to an external computer for receiving control data, or transmitting data collected.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] J. C. Boyd and D. E. Bruns, "Quality Specifications for Glucose Meters: Assessment by Simulation Modeling of Errors in," *Clinical Chemistry*, vol. 47, no. 2, pp. 209-214, 2001.
[2] R. A. d. Graaf, in vivo NMR Spectroscopy, John Wiley & Sons Ltd., 2007.
[3] W. R. Smythe, "Static and Dynamic Electricity", 2nd edition, p. 275, McGraw Hill.

The invention claimed is:

1. A portable spectrometer for use in performing nuclear magnetic resonance (NMR) spectroscopy on a sample, the portable spectrometer comprising:
a radiofrequency (RF) source configured to generate a pulsed RF signal;
a transmitting unit being configured to receive the pulsed RF signal and generate a pulsed RF stimulus field ($B_1$);
a receiving unit configured to receive a resonance signal generated by the sample in response to the pulsed RF stimulus field ($B_1$), the receiving unit comprising:
a first receiving pathway having a first receiving bandpass filter with at least one first receiving inductor coil which receives an in-phase component of the resonance signal; and
a second receiving pathway having a second receiving bandpass filter with at least one second receiving inductor coil which receives a quadrature component of the resonance signal,
wherein the first and second receiving band pass filter each include an outbound receiving probe inductor coil, and a return receiving probe inductor coil; and
a processor unit that is coupled to the RF source, the transmitting unit, and the receiving unit, the processor unit being configured to control the operation of the portable spectrometer by sending a control signal to the RF source to generate the pulsed RF signal and send the pulsed RF signal to the transmitting unit for generating the pulsed RF stimulus field ($B_1$), and the processor unit being further configured to receive the in-phase and quadrature components of the resonance signal from the receiving unit.

2. The portable spectrometer of claim 1, wherein the first and second receiving band pass filters, are each differential band pass filters synthesized from a tee topology low pass filter.

3. The portable spectrometer of claim 1, wherein the at least one first receiving inductor coil of the first receiving band pass filter, and the at least one second receiving inductor coil of the second receiving band pass filter, are one of surface coils and volume coils.

4. The portable spectrometer of claim 1, wherein the receiving band pass filters are at least $3^{rd}$ order band pass filters.

5. The portable spectrometer of claim 1, wherein the at least one first receiving inductor coil of the first receiving band pass filter, and the at least one second receiving inductor coil of the second receiving band pass filter, are each canted cosine coils which are positioned co-axially with respect to each other and with respect to a common axis, and generate an RF stimulus field ($B_1$) which is at least one of circularly and elliptically polarized.

6. The portable spectrometer of claim 5, wherein the common axis is orthogonal to an axis of a magnetic static field ($B_0$).

7. The portable spectrometer of claim 5, wherein the resonance signal is a free induction decay (FID) signal generated by a decay of a magnetization in a transverse plane, and the receiving unit uses a sum and a difference of the FID signals received by the two canted cosine coils to discriminate a projection of the magnetization onto two transverse spatial axes.

8. The portable spectrometer of claim 1, wherein the resonance signal is a free induction decay (FID) signal generated by a decay of a magnetization in a transverse plane.

9. The portable spectrometer of claim 1, wherein the first and second receiving pathways each comprise:
a transformer comprising a primary winding coupled to an output of the receiving band pass filter, wherein the transformer is configured to provide galvanic isolation, impedance matching, and common-mode noise rejection;
a low noise amplifier (LNA) coupled to a first node of a secondary winding of the transformer, wherein the LNA is configured to achieve a low noise figure in the filtered resonance signal and provide a uniform spectral noise distribution;
a variable gain amplifier (VGA) coupled to an output of the low noise amplifier, wherein the VGA is configured to boost the filtered resonance signal and minimize the overall receiver noise;
a local oscillator (LO) coupled to an output of the variable gain amplifier, wherein the LO is configured to generate an intermediate frequency; and
an analog to digital converter (ADC) coupled to the output of the LO.

10. The portable spectrometer of claim 9, wherein a second node of the secondary winding of the transformer is center-tapped for local ground referencing, and wherein the turn ratio of the transformer is selected for optimal impedance matching.

11. The portable spectrometer of claim 9, wherein the transformer comprises a wideband transformer balun.

12. The portable spectrometer of claim 9, wherein the LNA is formed of GaAs E-pHEMT technology and is configured to provide a noise figure below 1 dB.

13. The portable spectrometer of claim 9, wherein the VGA includes an automatic gain controller (AGC) which is configured to automatically reduce a gain of the VGA to prevent overload.

14. The portable spectrometer of claim 9, wherein the local oscillator is configured for a frequency offset of at least 100 kHz.

15. The portable spectrometer of claim 1, wherein noise generated by the receiving unit is less than 1.1 nV/√Hz as referred to input (RTI).

16. The portable spectrometer of claim 1, wherein the processor unit comprises at least one of a digital signal processor (DSP) and a field-programmable gate array (FPGA).

17. The portable spectrometer of claim 1, wherein the first and second receiving band pass filters are configured to pass a second passband range of frequencies which include at least one isotope Larmor frequency.

18. The portable spectrometer of claim 1, wherein the transmitting unit comprises one or more bandpass filters and one or more embedded coils.

19. The portable spectrometer of claim 18, wherein the RF signal has an in-phase component and a quadrature component and the transmitting unit comprises:
a first transmission pathway having a first transmitting bandpass filter with at least one first transmitting inductor coil which receives the in-phase component of the RF signal and generates the in-phase component of the RF stimulus field; and
a second transmission pathway having a second transmitting bandpass filter with at least one second transmitting inductor coil which receives the quadrature component of the RF signal and generates the quadrature component of the RF stimulus field.

20. The portable spectrometer of claim 19, wherein,
the first and second transmitting band pass filters are each differential band pass filters synthesized from a tee topology low pass filter,
the at least one first transmitting inductor coil of the first transmitting band pass filter and the at least one second transmitting inductor coil of the second transmitting band pass filter, are one of surface coils and volume.

21. The portable spectrometer of claim 20, wherein the first and second transmitting band pass filters are configured to pass a first passband range of frequencies which include at least one isotope Larmor frequency.

22. The portable spectrometer of claim 21, wherein the first passband range of frequencies includes two isotope Larmor frequencies, and the transmitting band pass filter is configured to support heteronuclear measurements.

23. The portable spectrometer of claim 22, wherein the two isotope Larmor frequencies are in respect of the Larmor frequencies of fluorine ($^{19}F$) and hydrogen ($^{1}H$).

24. The portable spectrometer of claim 21, wherein the first passband range of frequencies is between 60 MHz and 80 MHz.

25. The portable spectrometer of claim 19, wherein the at least one first transmitting inductor coil of the first transmitting band pass filter, and the at least one second transmitting inductor coil of the second transmitting band pass filter, are each canted cosine coils which are positioned co-axially with respect to each other and with respect to a common axis, and generate an RF stimulus field ($B_1$) which is at least one of circularly and elliptically polarized.

26. The portable spectrometer of claim 1, wherein the processor is further configured to perform at least one of: (a) storing the in-phase and quadrature components of the resonance signal in a memory unit of the processor unit for post-analysis; and (b) conducting an analysis on the in-phase and quadrature components of the resonance signal to determine the concentration of a metabolite in the sample.

27. A method for performing nuclear magnetic resonance (NMR) spectroscopy on a sample using a portable spectrometer, the method comprising:
applying a static magnetic field ($B_0$) to the sample;
generating, using a radiofrequency (RF) source, a pulsed RF signal;
generating, using a transmitting unit, a pulsed RF stimulus field ($B_1$) from the pulsed RF signal;
applying the pulsed RF stimulus field ($B_1$) to the sample;
receiving an in-phase component of a resonance signal generated by the sample using at least one first receiving inductor coil of a first receiving band pass filter of a receiving unit;
receiving a quadrature component of the resonance signal generated by the sample using at least one second receiving inductor coil of a second receiving band pass filter of the receiving unit, wherein the first and second receiving band pass filters have a second pass band range that includes the at least one Larmor frequency of the metabolite to be measured; and
passing the in-phase component of the resonance signal through the first receiving band pass filter to generate a filtered in-phase component of the resonance signal, and passing the quadrature component of the resonance signal through the second receiving band pass filter to generate a filtered quadrature component of the resonance signal,
wherein the first and second receiving band pass filter each include an outbound receiving probe inductor coil and a return receiving probe inductor coil.

28. The method of claim 27, wherein the resonance signal is a free induction decay (FID) signal generated by a decay of a magnetization in a transverse plane.

29. The method of claim 27, further comprising:
passing each of the in-phase component and the quadrature component of the resonance signal through a low noise amplifier, a variable gain amplifier, a local oscillator, and an analog to digital converter (ADC).

30. The method of claim 27, wherein the pulsed RF signal has an in-phase component and a quadrature component, and the method further comprising:
sending the in-phase component of the pulsed RF signal to a first transmitting band pass filter of the transmitting unit to generate a filtered in-phase RF component;
sending the quadrature component of the pulsed RF signal through a second transmitting band pass filter of the transmitting unit to generate a filtered quadrature RF component, wherein the first and second transmitting band pass filters have a first band pass range that includes at least one Larmor frequency of a metabolite to be measured; and
generating the pulsed RF stimulus field ($B_1$) by applying the filtered in-phase RF component to at least one first transmitting inductor coil of the first transmitting band pass filter, and applying the filtered quadrature RF component to at least one second transmitting inductor coil of the second transmitting band pass filter.

* * * * *